US010422760B2

(12) United States Patent
Sakashita et al.

(10) Patent No.: US 10,422,760 B2
(45) Date of Patent: Sep. 24, 2019

(54) METHOD FOR ANALYZING HONEYCOMB STRUCTURE, AND PROGRAM AND ANALYSIS DEVICE FOR THE SAME

(71) Applicant: NGK INSULATORS, LTD., Nagoya (JP)

(72) Inventors: Satoshi Sakashita, Yokkaichi (JP); Shingo Sokawa, Anjyo (JP); Rishun Kin, Handa (JP); Norihisa Fujie, Kasugai (JP)

(73) Assignee: NGK Insulators, Ltd., Nagoya (JP)

( * ) Notice: Subject to any disclaimer, the term of this patent is extended or adjusted under 35 U.S.C. 154(b) by 643 days.

(21) Appl. No.: 15/082,227

(22) Filed: Mar. 28, 2016

(65) Prior Publication Data

US 2016/0290943 A1 Oct. 6, 2016

(30) Foreign Application Priority Data

Mar. 31, 2015 (JP) .................... 2015-070757
Mar. 23, 2016 (JP) .................... 2016-058968

(51) Int. Cl.
*G01N 25/18* (2006.01)
*G06F 17/50* (2006.01)

(52) U.S. Cl.
CPC ......... *G01N 25/18* (2013.01); *G06F 17/5018* (2013.01); *G06F 2217/16* (2013.01); *G06F 2217/80* (2013.01)

(58) Field of Classification Search
CPC . G01N 25/18; G06F 17/5018; G06F 2217/80; G06F 2217/16
See application file for complete search history.

(56) References Cited

U.S. PATENT DOCUMENTS

2005/0191615 A1* 9/2005 Itou .................... G06F 17/5018
                                                                       435/4
2012/0248090 A1  10/2012 Furukawa et al.
(Continued)

FOREIGN PATENT DOCUMENTS

JP  2003-323467 A  11/2003
JP  2005-241448 A   9/2005
(Continued)

OTHER PUBLICATIONS

Young et al. "Mathematical Models of the Monolith Catalytic Converter: Part II. Application to Automobile Exhaust" AIChE Journal, vol. 22, No. 2, pp. 343-353 [retrieved on Sep. 19, 2018]. Retrieved from <https://onlinelibrary.wiley.com/doi/epdf/10.1002/aic.690220217> (Year: 1976).*

(Continued)

*Primary Examiner* — Aniss Chad
*Assistant Examiner* — Alfred H B Wechselberger
(74) *Attorney, Agent, or Firm* — Burr & Brown, PLLC

(57) ABSTRACT

Object information representing a honeycomb structure with a plurality of meshes is obtained, and an inner-wall-surface heat transfer coefficient $h_s$, i.e., a heat transfer coefficient between an inner wall surface of a cell and a fluid, is derived as follows. First, one of the meshes as a target for derivation of the inner-wall-surface heat transfer coefficient $h_s$ is set (S200), and a dimensionless coordinate $X^*$ is derived on the basis of position information (X-coordinate) of the set mesh and fluid state information (S210). An inner-wall-surface dimensionless heat transfer coefficient $Nu_s$ corresponding to the derived dimensionless coordinate $X^*$ is then derived on the basis of the inner-wall-surface dimensionless correspondence information (S220 to S250). The inner-wall-surface heat transfer coefficient $h_s$ in the mesh set as the derivation (Continued)

target is then derived on the basis of the derived inner-wall-surface dimensionless heat transfer coefficient $Nu_s$ (S260).

14 Claims, 24 Drawing Sheets

(56) References Cited

U.S. PATENT DOCUMENTS

| | | | |
|---|---|---|---|
| 2013/0060541 A1 | 3/2013 | Mangat et al. | |
| 2014/0020877 A1* | 1/2014 | Suzuki | F01N 3/2828 165/181 |

FOREIGN PATENT DOCUMENTS

| | | |
|---|---|---|
| JP | 2005-242679 A | 9/2005 |
| JP | 2012-214364 A | 11/2012 |
| WO | 2013/095494 A1 | 6/2013 |

OTHER PUBLICATIONS

Wanker et al. "A fully distributed model for the simulation of a catalytic combuster" Chemical Engineering Science, vol. 55, pp. 4709-4718 [retrieved on Sep. 19, 2018]. Retrieved from <https://www.sciencedirect.com/science/article/pii/S0009250900000609> (Year: 2000).*

Chen et al. "A Three-Dimensional Model for the Analysis of Transient Thermal and Conversion Characteristics of Monolithic Catalytic Converters" Society of Automotive Engineers, No. 880282 [retrieved on Sep. 21, 2018]. Retrieved from STIC. (Year: 1988).*

Martinez et al. "Modeling the vibrations in a catalytic converter for diesel engine" 2011 SIMULIA Customer Conference [retrieved on Sep. 18, 2018]. Retrieved from <https://docplayer.net/33916076-Modeling-the-vibrations-in-a-catalytic-converter-for-diesel-engine.htnnl > (Year: 2011).*

Nair, N. "A Computationally Efficient Model for the Simulation of Catalytic Monolith Reactors with Detailed Chemistry" [retrieved on Sep. 18, 2018]. Retrieved from <https://etd.ohiolink.edu/rws_etd/document/get/osu1374005338/inline> (Year: 2013).*

Rohsenow "Handbook of Heat Transfer" Chap. 5, Third Edition: McGraw-Hill, ISBN 0-07-053555-8 [retrieved on Sep. 18, 2018]. Retrieved from <https://www.researchgate.net/publication/206201081_Handbook_of_Heat_Transfer> (Year: 1998).*

Tsinoglou et al. "Transient modelling of flow distribution in automotive catalytic converters" Applied Mathematical Modeling, vol. 28, pp. 775-794 [retrieved on Sep. 18, 2018]. Retrieved from <https://www.sciencedirect.com/science/article/pii/S0307904X04000162> (Year: 2004).*

Santacreu et al. "Thermomechanical Fatigue Behavior of Stainless Steel Grades for Automotive Exhaust Manifold Applications" STP1428-EB: ASTM International [retrieved on Sep. 18, 2018]. Retrieved from <https://www.astm.org/Digital_Library/STP/PAGES/STP11437S.htm> (Year: 2003).*

Hong et al. "Simulation of Catalytic Combustion of Methane in a Monolith Honeycomb Reactor" Chinese J. Chem. Eng., vol. 14, No. 1, pp. 56-64 [retrieved on Sep. 21, 2018]. Retrieved from <https://www.sciencedirect.com/science/article/pii/S1004954106600384> (Year: 2006).*

Young et al. "Mathematical Models of the Monolith Catalytic Converter: Part I. Development of Model and Application of Orthogonal Collocation" AIChE Journal, vol. 22, No. 2, pp. 331-343 [retreived on Sep. 19, 2018]. Retrieved from <https://onlinelibrary.wiley.com/doi/abs/10.1002/aic.690220216> (Year: 1976).*

Phan et al. "Determination of the Nusselt versus Graetz Correlation for Heat Transfer in Channels of Sinusoidal Cross-Section" Korean J. Chem. Eng., vol. 20, No. 6, pp. 1012-1016 [retrieved on Sep. 19, 2018]. Retrieved from <https://link.springer.com/article/10.1007/BF02706929> (Year: 2003).*

Ciuffini et al. "Multiscale Computational Fluid Dynamics Methodology for Predicting Thermal Performance . . ." Journ of Heat Trnsf, Apr. 5, 2016, vol. 138, Issue 7 [retrieved on May 9, 2019]. Retrieved from <https://heattransfer.asmedigitalcollection.asme.org/article.aspx?articleid=2503832>(Year: 2016).*

Aly, W. "Numerical study on turbulent heat transfer and pressure drop of nanofluid in coiled lube-in-tube heat exchangers" Energy Conversion and Management, vol. 79, pp. 304-316 [retrieved on May 9, 2019]. Retrieved from <https://www.sciencedirect.com/science/article/pii/S0196890413008078>(Year: 2014).*

"*Heat Transmission Engineering,*" The Japan Society of Mechanical Engineers, Apr. 2005, p. 184 (with partial translation).

Extended European Search Report (Application No. 16163149.4) dated Nov. 29, 2016, 10 pages.

Margaritis Kostoglou et al.: "Improved Transfer Coefficients for Wall-Flow Monolithic Catalytic Reactors: Energy and Momentum Transport", Industrial & Engineering Chemistry Research, vol. 51, No. 40, Oct. 10, 2012, pp. 13062-13072.

David Schlereth et al.: "Comparison of a Pseudocontinuous, Heterogeneous 2D Conductive Monolith Reactor Model to a 3D Computational Fluid Dynamics Model", Industrial & Engineering Chemistry Research, vol. 53, No. 28, Jul. 16, 2014, pp. 11550-11556.

* cited by examiner

FIG. 4

| Coordinate | | | Honeycomb Mesh | | | | | | | | | | | |
|---|---|---|---|---|---|---|---|---|---|---|---|---|---|---|
| | | | Wall Mesh | | | | | | | Cell Mesh | | | | |
| | | | Structural Information | | | Physical Property Values | | | | Structural Information | | | Shape Information | |
| | | | | | | | Wall Thermal Conductivity $\lambda_r$ | | | | | | Weight for Each of Shape Elements | |
| X | Y | Z | Cell Pitch P | Wall Thickness Wt | End-Surface Heat Transmission Area $A_e$ | Wall Density $\rho_r$ | Wall Specific Heat $Cp_r$ | Cross-Sectional Direction $\lambda_{r1}$ | Flow-Path Direction $\lambda_{r2}$ | Position Type Information | Hydraulic Diameter $d_h$ | Inner-Wall-Surface Heat Transmission Area $A_s$ | Cell Shape | Weight K1 for Flat Portion | Weight K2 for Corner Portion |
| ... | ... | ... | *** | *** | *** | ** | ** | ** | ** | Front End | ... | ... | Rectangular | 0.7 | 0.3 |
| ... | ... | ... | ... | ... | ... | ** | ** | ** | ** | ... | ... | ... | Rectangular | 0.7 | 0.3 |
| ... | ... | ... | — | — | — | ** | ** | ** | ** | Intermediate | ... | ... | ... | ... | ... |
| ... | ... | ... | — | — | — | ** | ** | ** | ** | Intermediate | ... | ... | ... | ... | ... |
| ... | ... | ... | ... | ... | ... | ** | ** | ** | ** | ... | ... | ... | ... | ... | ... |
| ... | ... | ... | *** | *** | *** | ** | ** | ** | ** | Rear End | ... | ... | ... | ... | ... |

~20

Up (Z Direction)
Rear (X Direction)
Left
Right (Y Direction)
Front
Down

Wall Temperature Tr    Fluid Temperature Tg

| Cell Shape | Cell Shape | Rear-end-surface [$Nu_{er} = Dr \cdot exp(Er \cdot OFA)$] | |
|---|---|---|---|
| | | Dr | Er |
| Rectangle | Flat Portion | $Dr_{11}(=2.8)$ | $Er_{11}(=0.3)$ |
| | Corner Portion | $Dr_{12}(=11)$ | $Er_{12}(=-3.5)$ |
| Hexagon | Flat Portion | $Dr_{21}(=3.0)$ | $Er_{21}(=0.3)$ |
| | Corner Portion | $Dr_{22}(=1.1)$ | $Er_{22}(=0.7)$ |

| Coordinate | | | Thermocouple Mesh | | | | Position Type |
|---|---|---|---|---|---|---|---|
| | | | Structural Information | Physical Property Values | | | |
| X | Y | Z | Diameter R | Thermocouple Density $\rho_t$ | Thermocouple Specific Heat $Cp_t$ | Thermocouple Thermal Conductivity $\lambda_t$ | |
| ... | ... | ... | *** | ** | ** | ** | End Surface |
| ... | ... | ... | *** | ** | ** | ** | — |
| ... | ... | ... | *** | ** | ** | ** | — |
| ... | ... | ... | *** | ** | ** | ** | — |
| ... | ... | ... | *** | ** | ** | ** | — |
| ... | ... | ... | *** | ** | ** | ** | — |

METHOD FOR ANALYZING HONEYCOMB STRUCTURE, AND PROGRAM AND ANALYSIS DEVICE FOR THE SAME

BACKGROUND OF THE INVENTION

1. Field of the Invention

The present invention relates to a method for analyzing a honeycomb structure, and a program and an analysis device for the same.

2. Description of the Related Art

There is so far known a honeycomb structure including walls that form a plurality of cells serving as flow paths for a fluid. Such a honeycomb structure is utilized, for example, in a catalyst carrier for carrying a catalyst that purifies exhaust gas from automobile engines (see, e.g., Patent Literature (PTL) 1).

Because the honeycomb structure is exposed to a high-temperature fluid such as the exhaust gas, the honeycomb structure preferably has high thermal shock resistance. Analyzing a temperature distribution inside the honeycomb structure when exposed to the fluid is often demanded to evaluate the thermal shock resistance. In general, as a method of analyzing a temperature distribution inside an object, it is known to perform a heat transfer analysis in accordance with, e.g., the finite element method or the finite volume method (see, e.g., PTL 2). It is further known that a heat transfer coefficient between an object and a fluid is usually approximated by a constant value (see, e.g., Non Patent Literature (NPL) 1).

CITATION LIST

Patent Literature

[PTL 1] Japanese Unexamined Patent Application Publication No. 2012-214364
[PTL 2] Japanese Unexamined Patent Application Publication No. 2003-323467

Non Patent Literature

[NPL 1] "Heat Transmission Engineering", The Japan Society of Mechanical Engineers, April 2005, p. 184

SUMMARY OF THE INVENTION

In the case of analyzing, with the heat transfer analysis, the temperature distribution inside the honeycomb structure exposed to the fluid, however, when the heat transfer analysis is performed on condition of approximating the heat transfer coefficient by a constant value, accuracy in the analysis of the temperature distribution is not sufficient in some cases. On the other hand, when the heat transfer coefficient is not approximated by a constant value, the heat transfer coefficient varies depending on the state of a fluid. However, there is not yet known an effective method of deriving the heat transfer coefficient that reflects the state of the fluid in contact with the honeycomb structure.

The present invention has been accomplished with intent to solve the problems described above, and a main object of the present invention is to more accurately analyze the state of a honeycomb structure when the honeycomb structure is exposed to a fluid.

To achieve the above main object, the present invention is constituted as follows.

The method for analyzing a honeycomb structure according to the present invention includes:

a method for analyzing, on a honeycomb structure including walls forming a plurality of cells that serve as flow paths for a fluid, a state of the honeycomb structure after lapse of a predetermined time from an analysis start time when the honeycomb structure is exposed to the fluid, the method comprising:

an object information obtaining step of obtaining object information that simulates the honeycomb structure with a plurality of meshes involving wall meshes representing the walls and cell meshes representing the cells, the object information containing position information for each of the meshes;

an inner-wall-surface dimensionless correspondence information obtaining step of obtaining inner-wall-surface dimensionless correspondence information that is information regarding a correspondence relation between a dimensionless coordinate, which is a dimensionless value indicating a position of the mesh, and an inner-wall-surface dimensionless heat transfer coefficient, which is a dimensionless value of an inner-wall-surface heat transfer coefficient representing a heat transfer coefficient between an inner wall surface of the cell and the fluid;

an inner-wall-surface heat transfer coefficient deriving step of executing, at an arbitrary time from the analysis start time until lapse of the predetermined time, a process of setting, from among the plurality of meshes, the wall mesh and the cell mesh as a derivation target for which the inner-wall-surface heat transfer coefficient is to be derived, deriving the dimensionless coordinate on basis of both the position information of the set mesh and fluid state information regarding a state of the fluid in the set cell mesh at the relevant time, deriving the inner-wall-surface dimensionless heat transfer coefficient corresponding to the derived dimensionless coordinate on basis of the inner-wall-surface dimensionless correspondence information, and deriving the inner-wall-surface heat transfer coefficient between the set wall mesh and the set cell mesh on basis of the derived inner-wall-surface dimensionless heat transfer coefficient, and further executing the aforesaid process for the plural wall meshes and the plural cell meshes while the derivation target is changed from one to another;

a heat transfer analysis step of executing, at an arbitrary time from the analysis start time until the lapse of the predetermined time, a heat transfer analysis including a process of deriving a heat transfer amount between the wall mesh and the cell mesh on basis of the inner-wall-surface heat transfer coefficient derived in the inner-wall-surface heat transfer coefficient deriving step, and deriving temperatures of the plural wall meshes and temperatures of the fluids in the plural cell meshes after lapse of a short time from the relevant time; and a temperature distribution deriving step of repeatedly executing the inner-wall-surface heat transfer coefficient deriving step and the heat transfer analysis step, and deriving respective temperatures of the plural wall meshes after the lapse of the predetermined time.

According to the analysis method described above, the inner-wall-surface heat transfer coefficient, i.e., the heat transfer coefficient between the inner wall surface of the cell and the fluid, at an arbitrary time is derived as follows. First, the wall mesh and the cell mesh as the target for derivation of the inner-wall-surface heat transfer coefficient are set, and the dimensionless coordinate is derived on the basis of the position information of the set mesh and the fluid state information regarding the state of the fluid in the set cell mesh at the relevant time. Then, the inner-wall-surface dimensionless heat transfer coefficient corresponding to the derived dimensionless coordinate is derived on the basis of the inner-wall-surface dimensionless correspondence information. Then, the inner-wall-surface heat transfer coefficient between the set wall mesh and the set cell mesh is derived on the basis of the derived inner-wall-surface dimensionless heat transfer coefficient. The above-mentioned processes are further executed on the plural wall meshes and the plural cell meshes while the derivation target is changed from one to another. Here, the relation between the dimensionless coordinate and the inner-wall-surface dimensionless heat transfer coefficient can be expressed by the same correspondence relation regardless of the fluid state. Therefore, by deriving the dimensionless coordinate on the basis of the fluid state information at an arbitrary time, it is possible to derive the inner-wall-surface dimensionless heat transfer coefficient by employing the same correspondence relation, and to appropriately derive the inner-wall-surface heat transfer coefficient reflecting the fluid state information in arbitrary one of the meshes at an arbitrary time. Thus, by executing the heat transfer analysis including the derivation of the heat transfer amounts with the use of the inner-wall-surface heat transfer coefficients that have been derived for the plural meshes, the temperatures of the plural wall meshes and the fluid temperatures in the plural cell meshes after the lapse of a short time from an arbitrary time can be derived with higher accuracy than that when the heat transfer coefficient is approximated by a constant value. In other words, the heat transfer analysis process can be performed with higher accuracy. By repeatedly executing the above inner-wall-surface heat transfer coefficient deriving step and the above heat transfer analysis step, the heat transfer analysis can be accurately performed over a period from the analysis start time until the lapse of the predetermined time, and the respective wall temperatures of the plural wall meshes after the lapse of the predetermined time can be accurately derived. As a result, the state of the honeycomb structure when the honeycomb structure is exposed to the fluid can be analyzed with higher accuracy.

Here, the expression "when the honeycomb structure is exposed to the fluid" includes, for example, the case where the fluid flows into the cells of the honeycomb structure from the outside, and the case where the fluid in the cell causes natural convection. Furthermore, the "fluid state information" is information that represents a state of the fluid, and that may contain at least a flow velocity of the fluid, or at least either the flow velocity or one or more physical property values of the fluid. The physical property value(s) of the fluid may be one or more of a specific heat, a density, and a thermal conductivity, for example. A value of one or more items of the fluid state information for each cell mesh at each time may be set in advance. In such a case, one or more items of the fluid state information may be values not variable depending on time, or may be the same value among the plural cell meshes representing parts of the same cell. One or more items of the fluid state information may be derived on the basis of the temperature of the fluid for each cell mesh at each time. When the fluid state information contains the flow velocity of the fluid, the flow velocity of the fluid may be derived on the basis of a flow rate of the fluid, which has been set in advance. The "position information of the set mesh" may be position information of at least one of the wall mesh and the cell mesh, which have been set as the derivation target, or may be position information derived from two data of position information of both the meshes. The derivation of the dimensionless coordinate may be performed on the basis of information contained in the position information of the mesh set as the derivation target, the information representing a coordinate in a predetermined direction along a flowing direction of the fluid in the cell. The derivation of the dimensionless coordinate may be performed on the basis of the position information of the mesh set as the derivation target, the fluid state information, and a typical cell length (hydraulic diameter) represented by the cell mesh set as the derivation target. The derivation of the inner-wall-surface heat transfer coefficient may be performed on the basis of the inner-wall-surface dimensionless heat transfer coefficient, the thermal conductivity of the fluid in the cell mesh set as the derivation target, and the typical cell length (hydraulic diameter) represented by the cell mesh set as the derivation target. The thermal conductivity of the fluid may be a value derived on the basis of the temperature of the fluid in the cell mesh set as the derivation target. The object information may be information simulating the honeycomb structure in which a cross-section of at least one of the plural cells has a polygonal shape. The polygonal shape may include, e.g., a rectangular shape and a hexagonal shape. In the object information, the wall mesh and the cell mesh may be arranged such that they at least partly contact with each other, or such that they at least partly overlap with each other. In the inner-wall-surface heat transfer coefficient deriving step, a combination of the wall mesh and the cell mesh, which at least partly contacts or at least partly overlap with the relevant wall mesh, may be set as the derivation target. The fluid includes gas and a liquid.

In the method for analyzing a honeycomb structure according to the present invention, in the object information, one or more of the plural wall meshes each may represent a region of the honeycomb structure, the region involving at least a part of the walls and at least a part of the cells together, in a homogenized state. With that feature, the number of meshes can be reduced in comparison with the case of, for example, representing the entire structural configuration (shape) of the walls with the plural wall meshes. Hence a time (computing time) needed to execute processing in, e.g., the inner-wall-surface heat transfer coefficient deriving step and the heat transfer analysis step, can be shortened. In this connection, in the object information, one of the wall mesh and the cell mesh may involve the other. In such a case, one mesh (i.e., the mesh involving the other) may double as the other mesh (i.e., the involved mesh). Moreover, in the object information, the wall mesh and the cell mesh may be arranged such that their sizes and positions are matched with each other. In such a case, one of both the meshes may double as the other. When one of the wall mesh and the cell mesh doubles as the other, a process of setting one mesh as the derivation target in the inner-wall-surface heat transfer coefficient deriving step corresponds to the process of setting the wall mesh and the cell mesh as the derivation target.

In the method for analyzing a honeycomb structure according to the present invention, the object information may contain, in correspondence to at least one of the wall mesh and the cell mesh, shape information regarding a shape of the inner wall surface of the cell, and the inner-wall-surface dimensionless correspondence information may contain the correspondence relation between the dimensionless coordinate and the inner-wall-surface dimensionless heat transfer coefficient, the relevant correspondence relation being different for each shape of the inner wall surface. In the inner-wall-surface heat transfer coefficient deriving step, the derivation of the inner-wall-surface dimensionless heat transfer coefficient on the basis of the dimensionless coordinate may be executed by employing the correspondence relation between the dimensionless coordinate and the inner-wall-surface dimensionless heat transfer coefficient, the relevant correspondence relation being specified on the basis of the shape information in correspondence to the mesh set as a target for the derivation. With those features, the inner-wall-surface heat transfer coefficient can be derived with higher accuracy in consideration of the shape of the inner wall surface.

In the method for analyzing a honeycomb structure according to the present invention, the object information may contain, in correspondence to at least one of the wall mesh and the cell mesh, shape information that is information representing a shape of the inner wall surface of the cell as a combination of plural shape elements, and the inner-wall-surface dimensionless correspondence information may contain the correspondence relation between the dimensionless coordinate and the inner-wall-surface dimensionless heat transfer coefficient, the relevant correspondence relation being different for each of the shape elements. In the inner-wall-surface heat transfer coefficient deriving step, the derivation of the inner-wall-surface dimensionless heat transfer coefficient corresponding to each of the shape elements may be executed by employing the correspondence relation between the dimensionless coordinate and the inner-wall-surface dimensionless heat transfer coefficient, the relevant correspondence relation being specified on the basis of each of the shape elements contained in the shape information in correspondence to the mesh set as a target for the derivation. With those features, since the shape of the inner wall surface is represented by the combination of the shape elements, the inner-wall-surface heat transfer coefficient can be derived with higher accuracy in consideration of the shape of the inner wall surface. In the above case, the inner-wall-surface heat transfer coefficient deriving step may be executed to derive one heat transfer coefficient on the basis of respective dimensionless heat transfer coefficients corresponding to the shape elements, or to derive the respective heat transfer coefficients corresponding to the shape elements individually. Furthermore, the shape information may be information representing the shape of the inner wall surface in a combination of plural shape elements and respective weights assigned to the plural shape elements. In such a case, when the inner-wall-surface dimensionless heat transfer coefficient corresponding to each of the shape elements is derived in the inner-wall-surface heat transfer coefficient deriving step, the inner-wall-surface dimensionless heat transfer coefficient weighted with the weight corresponding to each shape element may be derived. As an alternative, the use of the weight may be avoided at the time of deriving the inner-wall-surface dimensionless heat transfer coefficient in the inner-wall-surface heat transfer coefficient deriving step, and at the time of deriving the heat transfer amount using the heat transfer coefficient corresponding to each of the shape elements, the heat transfer amount weighted with the weight corresponding to each of the shape elements may be derived. The above-mentioned weight may be given as a value depending on a ratio of an area of each shape element to an area of the inner wall surface.

In the method for analyzing a honeycomb structure according to the present invention, the object information may be information simulating the honeycomb structure in which the inner wall surface of at least one of the plural cells has a polygonal cross-section, and the shape information may contain, as the plural shape elements, a corner portion and a flat portion of an inner wall surface of the polygonal cross-section. With those features, since the inner wall surface having the polygonal cross-section is represented by the shape elements including the corner portion and the flat portion, the inner-wall-surface heat transfer coefficient can be derived with higher accuracy in consideration of the shape of the inner wall surface. It is to be noted that the "corner portion" includes a corner in shape having a curved surface.

In the method for analyzing a honeycomb structure according to the present invention, the inner-wall-surface dimensionless correspondence information may contain, as the correspondence relation between the dimensionless coordinate and the inner-wall-surface dimensionless heat transfer coefficient in a fluid entrance region of the cell, information regarding a correspondence relation expressed by the following equation (1), and in the inner-wall-surface heat transfer coefficient deriving step, the inner-wall-surface dimensionless heat transfer coefficient may be derived on the basis of the information regarding the correspondence relation expressed by the equation (1) when the derived dimensionless coordinate is positioned in the fluid entrance region. With those features, the inner-wall-surface heat transfer coefficient in the entrance region can be derived with higher accuracy by employing the correspondence relation expressed by the equation (1).

$$Nu_s = A \times (X^*)^B \qquad \text{Eq. (1)}$$

(where $Nu_s$: inner-wall-surface dimensionless heat transfer coefficient, $X^*$: dimensionless coordinate, and A, B: coefficients)

In the method for analyzing a honeycomb structure according to the present invention, the inner-wall-surface dimensionless correspondence information may contain, as the correspondence relation between the dimensionless coordinate and the inner-wall-surface dimensionless heat transfer coefficient in a fluid developed region of the cell, information regarding a correspondence relation expressed by the following equation (2), and in the inner-wall-surface heat transfer coefficient deriving step, the inner-wall-surface dimensionless heat transfer coefficient may be derived on the basis of the information regarding the correspondence relation expressed by the equation (2) when the derived dimensionless coordinate is positioned in the fluid developed region. With those features, the inner-wall-surface heat transfer coefficient in the developed region can be derived with higher accuracy by employing the correspondence relation expressed by the equation (2).

$$Nu_s = C \qquad \text{Eq. (2)}$$

(where $Nu_s$: inner-wall-surface dimensionless heat transfer coefficient and C: coefficient)

The method for analyzing a honeycomb structure according to the present invention may further include an end-surface heat transfer coefficient deriving step of executing, at an arbitrary time from the analysis start time until the lapse of the predetermined time, a process of setting, from among a plurality of end wall meshes belonging to the wall meshes and representing the walls that involve open end surfaces of the cells in the honeycomb structure, one end wall mesh as a target for derivation of an end-surface heat transfer coefficient representing a heat transfer coefficient between the open end surface of the relevant end wall mesh and the fluid, obtaining an end-surface dimensionless heat transfer coefficient that is a dimensionless value of the end-surface heat transfer coefficient in the set end wall mesh, and deriving the end-surface heat transfer coefficient in the set end wall mesh on the basis of the derived end-surface dimensionless heat transfer coefficient, and further executing the aforesaid process for the plural end wall meshes while the derivation target is changed from one to another, wherein, in the heat transfer analysis step, the heat transfer analysis may be executed at an arbitrary time from the analysis start time until the lapse of the predetermined time in consideration of a heat transfer amount between the end wall mesh and the fluid, the heat transfer amount being derived on the basis of the derived end-surface heat transfer coefficient, and the inner-wall-surface heat transfer coefficient deriving step, the end-surface heat transfer coefficient deriving step, and the heat transfer analysis step may be repeatedly executed in the temperature distribution deriving step to derive respective temperatures of the plural wall meshes after the lapse of the predetermined time. With those features, the end-surface heat transfer coefficient can be appropriately derived by employing the end-surface dimensionless heat transfer coefficient. Moreover, since the end-surface heat transfer coefficient is taken into consideration, the heat transfer analysis can be performed with higher accuracy. In the above case, the end-surface heat transfer coefficient may be derived in the end-surface heat transfer coefficient deriving step at an arbitrary time from the analysis start time until the lapse of the predetermined time on the basis of the derived end-surface dimensionless heat transfer coefficient, the thermal conductivity of the fluid contacting the open end surface of the set end wall mesh, and the hydraulic diameter of the cell. The thermal conductivity of the fluid may be set to a constant value not depending on time, or to a value variable depending on time. The thermal conductivity of the fluid may be a value derived on the basis of a temperature of the fluid contacting the open end surface at the above arbitrary time.

In the method for analyzing a honeycomb structure according to the present invention, the object information may contain, in correspondence to the end wall mesh, information regarding an opening rate that is a value representing a rate of an opening of the cell in the open end surface, and in the end-surface heat transfer coefficient deriving step, the end-surface dimensionless heat transfer coefficient may be derived and obtained on the basis of the opening rate of the end wall mesh set as the derivation target. With those features, the end-surface dimensionless heat transfer coefficient can be derived with higher accuracy on the basis of the opening rate, and hence the end-surface heat transfer coefficient can be derived with higher accuracy. Here, the "information regarding the opening rate" contains not only the opening rate itself, but also information from which the opening rate can be derived. The information from which the opening rate can be derived may be information of, e.g., a cell pitch and a wall thickness.

In the method for analyzing a honeycomb structure according to the present invention, in the end-surface heat transfer coefficient deriving step, the end-surface dimensionless heat transfer coefficient may be derived from a relation of the following equation (3). With that feature, the end-surface heat transfer coefficient can be derived with higher accuracy by employing the relation of the equation (3).

$$Nu_e = D \times \exp(E \times OFA) \qquad \text{Eq. (3)}$$

(where $Nu_e$: end-surface dimensionless heat transfer coefficient, D, E: coefficients, and OFA: opening rate)

In the above case, the opening rate OFA may be derived from a relation of the following equation (4).

$$OFA = (P - Wt)^2 / P^2 \qquad \text{Eq. (4)}$$

(where P: cell pitch, and Wt: wall thickness)

In the method for analyzing a honeycomb structure according to the present invention, the object information may be information simulating the honeycomb structure, which is in a state including a thermocouple inserted in the cell, with a plurality of meshes involving the wall meshes, the cell meshes, and a plurality of thermocouple meshes representing the thermocouple. The analysis method may further include a thermocouple outer-peripheral-surface dimensionless correspondence information obtaining step of obtaining thermocouple outer-peripheral-surface dimensionless correspondence information that is information regarding a correspondence relation between a dimensionless coordinate, which is a dimensionless value indicating a position of the mesh, and a thermocouple outer-peripheral-surface dimensionless heat transfer coefficient, which is a dimensionless value of a thermocouple outer-peripheral-surface heat transfer coefficient representing a heat transfer coefficient between an outer peripheral surface of the thermocouple and the fluid; and a thermocouple outer-peripheral-surface heat transfer coefficient deriving step of executing, at an arbitrary time from the analysis start time until the lapse of the predetermined time, a process of setting, from among the plurality of meshes, the thermocouple mesh and the cell mesh as a derivation target for which the thermocouple outer-peripheral-surface heat transfer coefficient is to be derived, deriving the dimensionless coordinate on the basis of both the position information of the set mesh and the fluid state information regarding the fluid in the set cell mesh at the relevant time, deriving the thermocouple outer-peripheral-surface dimensionless heat transfer coefficient corresponding to the derived dimensionless coordinate on the basis of the thermocouple outer-peripheral-surface dimensionless correspondence information, and deriving the thermocouple outer-peripheral-surface heat transfer coefficient between the set thermocouple mesh and the set cell mesh on the basis of the derived thermocouple outer-peripheral-surface dimensionless heat transfer coefficient, and further executing the aforesaid process for the plural thermocouple meshes and the plural cell meshes while the derivation target is changed from one to another. Moreover, in the heat transfer analysis step, the heat transfer analysis may be executed at an arbitrary time from the analysis start time until the lapse of the predetermined time in consideration of a heat transfer amount between the thermocouple mesh and the cell mesh, the heat transfer amount being derived on the basis of the derived thermocouple outer-peripheral-surface heat transfer coefficient, thus deriving a temperature of the thermocouple mesh after the lapse of a short time from the relevant time, and the inner-wall-surface heat transfer coefficient deriving step, the thermocouple outer-peripheral-surface heat transfer coefficient deriving step, and the heat transfer analysis step may be repeatedly executed in the temperature distribution deriving step to derive respective temperatures of the plural wall meshes and respective temperatures of the thermocouple meshes after the lapse of the predetermined time. With those features, the honeycomb structure in the state including the thermocouple inserted in the cell can be analyzed. In addition, not only the wall temperature, but also the thermocouple temperature can be analyzed.

The method for analyzing a honeycomb structure according to the present invention may further include a stress analysis step of analyzing a distribution of stress, which is generated inside the honeycomb structure, on the basis of the respective temperatures of the wall meshes derived in the temperature distribution deriving step. With that feature, since the stress distribution is analyzed on the basis of the respective temperatures of the plural wall meshes, which have been accurately derived, the stress analysis can be accurately performed. The stress analysis step may be executed by employing the meshes that have been used in the temperature distribution deriving step, or by setting other meshes different from those used meshes.

A program according to the present invention causes one or more computers to operate and execute the steps of the method for analyzing a honeycomb structure described above. The program may be recorded in a computer-readable recording medium (e.g., a hard disk, ROM, FD, CD or DVD), or may be distributed from one computer to another computer via a transmission medium (communication network such as the Internet or LAN). Alternatively, the program may be transferred in any of other practicable manners. By running the program on one computer or on a plurality of computers in a way of sharing the various processes, the individual steps of the above-described method for analyzing a honeycomb structure are executed, and similar advantageous effects to those in the above-described method can be obtained.

The analysis device for analyzing a honeycomb structure according to the present invention includes:

an analysis device for analyzing a honeycomb structure that analyzes, on a honeycomb structure including walls forming a plurality of cells that serve as flow paths for a fluid, a state of the honeycomb structure after lapse of a predetermined time from an analysis start time when the honeycomb structure is exposed to the fluid, the analysis device comprising:

an object information obtaining module for obtaining object information that simulates the honeycomb structure with a plurality of meshes involving wall meshes representing the walls and cell meshes representing the cells, the object information containing position information for each of the meshes;

an inner-wall-surface dimensionless correspondence information obtaining module for obtaining inner-wall-surface dimensionless correspondence information that is information regarding a correspondence relation between a dimensionless coordinate, which is a dimensionless value indicating a position of the mesh, and an inner-wall-surface dimensionless heat transfer coefficient, which is a dimensionless value of an inner-wall-surface heat transfer coefficient representing a heat transfer coefficient between an inner wall surface of the cell and the fluid;

an inner-wall-surface heat transfer coefficient deriving module for executing an inner-wall-surface heat transfer coefficient deriving process, that is, executing, at an arbitrary time from the analysis start time until lapse of the predetermined time, a process of setting, from among the plurality of meshes, the wall mesh and the cell mesh as a derivation target for which the inner-wall-surface heat transfer coefficient is to be derived, deriving the dimensionless coordinate on basis of both the position information of the set mesh and fluid state information regarding a state of the fluid in the set cell mesh at the relevant time, deriving the inner-wall-surface dimensionless heat transfer coefficient corresponding to the derived dimensionless coordinate on basis of the inner-wall-surface dimensionless correspondence information, and deriving the inner-wall-surface heat transfer coefficient between the set wall mesh and the set cell mesh on basis of the derived inner-wall-surface dimensionless heat transfer coefficient, and further executing the aforesaid process for the plural wall meshes and the plural cell meshes while the derivation target is changed from one to another;

a heat transfer analysis module for executing a heat transfer analysis process, that is, executing, at an arbitrary time from the analysis start time until the lapse of the predetermined time, a heat transfer analysis including a process of deriving a heat transfer amount between the wall mesh and the cell mesh on basis of the inner-wall-surface heat transfer coefficient derived in the inner-wall-surface heat transfer coefficient deriving process, and deriving temperatures of the plural wall meshes and temperatures of the fluids in the plural cell meshes after lapse of a short time from the relevant time; and a temperature distribution deriving module for repeatedly executing the inner-wall-surface heat transfer coefficient deriving process and the heat transfer analysis process by the inner-wall-surface heat transfer coefficient deriving module and the heat transfer analysis module, and deriving respective temperatures of the plural wall meshes after the lapse of the predetermined time.

With the above analysis device, respective temperatures of the plural wall meshes after the lapse of the predetermined time can be accurately derived as with the above-described analysis method. Therefore, the state of the honeycomb structure when the honeycomb structure is exposed to the fluid can be analyzed with higher accuracy. It is to be noted that the honeycomb structure analysis device may employ suitable one(s) of the various features of the above-described method for analyzing a honeycomb structure, or may be added with one or more components to realize suitable one(s) of the various features of the above-described method for analyzing a honeycomb structure.

BRIEF DESCRIPTION OF THE DRAWINGS

FIG. 4 is a conceptual view representing one example of the object information 20.

FIG. 19 is a conceptual view illustrating one example of part of the object information 120, the part regarding a thermocouple mesh 45.

DETAILED DESCRIPTION OF THE INVENTION

First Embodiment

Figure 1:
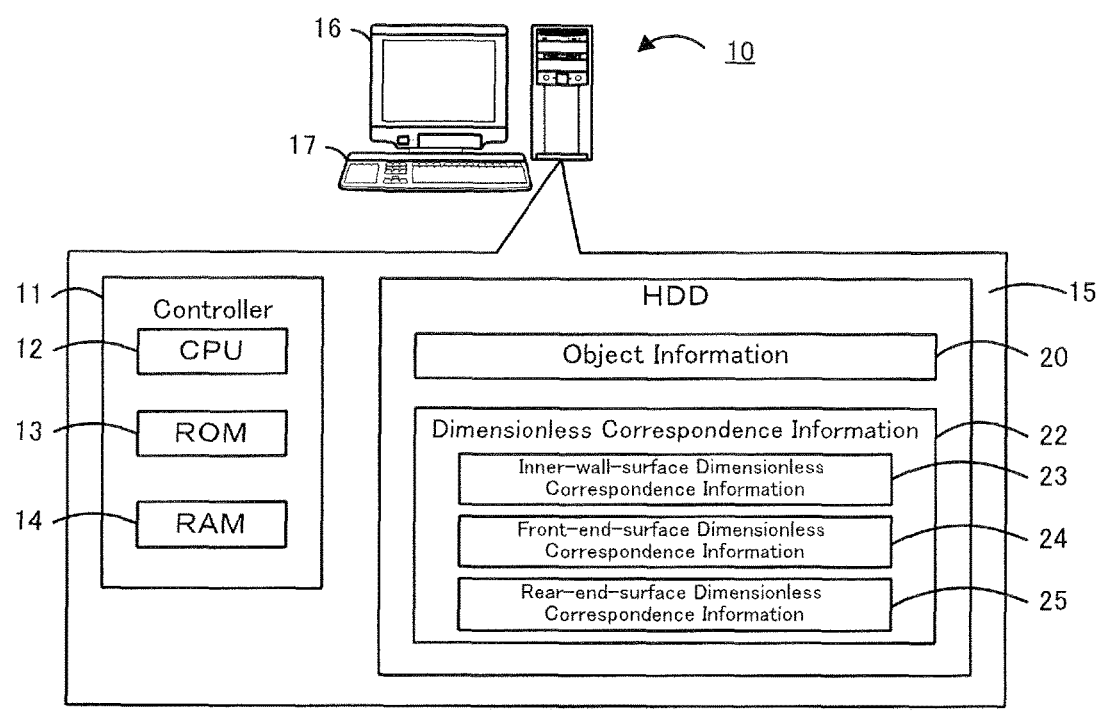
FIG. 1 is a block diagram schematically illustrating an analysis device 10 according to a first embodiment of the present invention.

Embodiments of the present invention will be described below with reference to the drawings. FIG. 1 is a block diagram schematically illustrating an analysis device 10 according to a first embodiment of the present invention. The analysis device 10 is constituted as a computer, e.g., a personal computer. The analysis device 10 includes a controller 11 including, e.g., a CPU 12 that executes various kinds of processing, a ROM 13 that stores various kinds of processing programs, etc., and a RAM 14 that temporarily stores data, and a HDD 15, i.e., a large-capacity memory, which stores various kinds of processing programs, such as an analysis processing program, and various kinds of data used in an analysis process. In addition, the analysis device 10 includes a display 16 that displays various kinds of information on a screen, and an input device 17, such as a mouse or a keyboard, through which a user enters various kinds of commands. Though described in detail later, the HDD 15 stores, e.g., object information 20 that is information simulating an object to be analyzed, fluid information 21 that is information of a fluid used in an analysis, and dimensionless correspondence information 22 that is used to derive a heat transfer coefficient in the analysis. The dimensionless correspondence information 22 contains inner-wall-surface dimensionless correspondence information 23, front-end-surface dimensionless correspondence information 24, and rear-end-surface dimensionless correspondence information 25. In accordance with the object information 20, the fluid information 21, the dimensionless correspondence information 22, etc. stored in the HDD 15, the analysis device 10 is able to perform the analysis when the object simulated with the object information 20 is exposed to a fluid.

Figure 2:
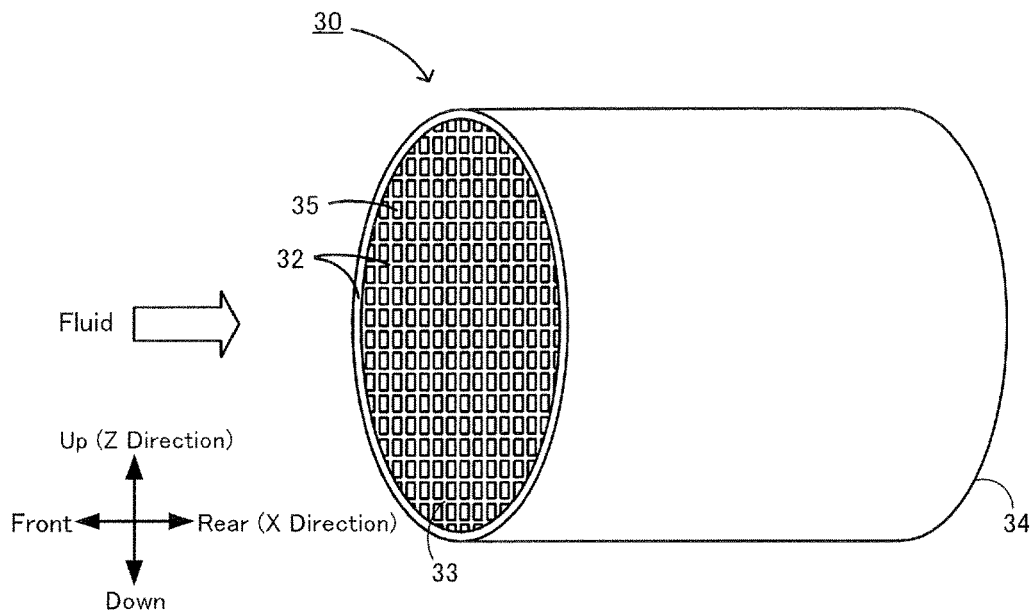
FIG. 2 is a schematic explanatory view illustrating one example of a honeycomb structure 30.
Figure 3:
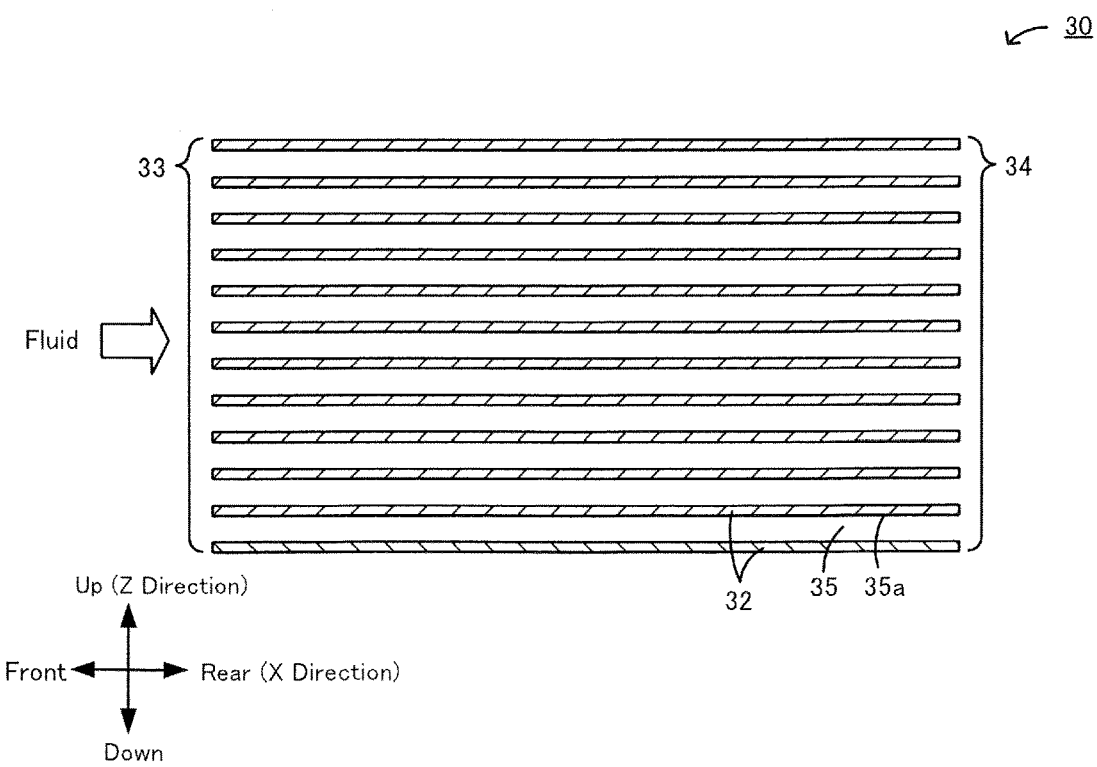
FIG. 3 is a sectional view of the honeycomb structure 30.

The object to be analyzed by the analysis device 10 is described here. FIG. 2 is a schematic explanatory view illustrating one example of a honeycomb structure 30 that is an example of the analysis object. FIG. 3 is a sectional view of the honeycomb structure 30 sectioned in a front-rear direction, i.e., a gas flowing direction within cells 35. It is to be noted that, in this embodiment, an up-down direction and the front-rear direction are defined as per denoted in FIGS. 2 and 3. A direction perpendicular to the up-down direction and the front-rear direction is defined as a right-left direction (see FIG. 5 described later). Moreover, a rearward direction is defined as an X-direction (positive direction of an X-axis), a rightward direction is defined as a Y-direction (positive direction of a Y-axis), and an upward direction is defined as a Z-direction (positive direction of a Z-axis). The honeycomb structure 30 is, for example, a member disposed in an engine exhaust pipe as a catalyst carrier for carrying a catalyst that purifies exhaust gas from an automobile engine. As illustrated in FIG. 2, the honeycomb structure 30 includes walls 32 (also called partition walls) that form the plurality of cells 35 serving as flow paths for the fluid. The honeycomb structure 30 is structured such that both ends of each cell 35 are through (opened) at a front end surface 33 and a rear end surface 34. An external shape of the honeycomb structure 30 is not limited to particular one, and it may be, e.g., circular cylindrical, quadrangular cylindrical, elliptic cylindrical, or hexagonal cylindrical. A cross-section of the cell 35 may have a polygonal shape, such as a triangular, rectangular, hexagonal, or octagonal shape, a circular shape, or an elliptic shape. This embodiment is described mainly in connection with the case where the external shape of the honeycomb structure 30 is circular cylindrical and the cell 35 has a rectangular sectional shape. Furthermore, the following description is made mainly in connection with the case where a fluid (e.g., engine exhaust gas) flows into the front end surface 33 of the honeycomb structure 30 from the front, passes through the cell 35, and flows out from the rear end surface 34 rearwards.

Figure 5:
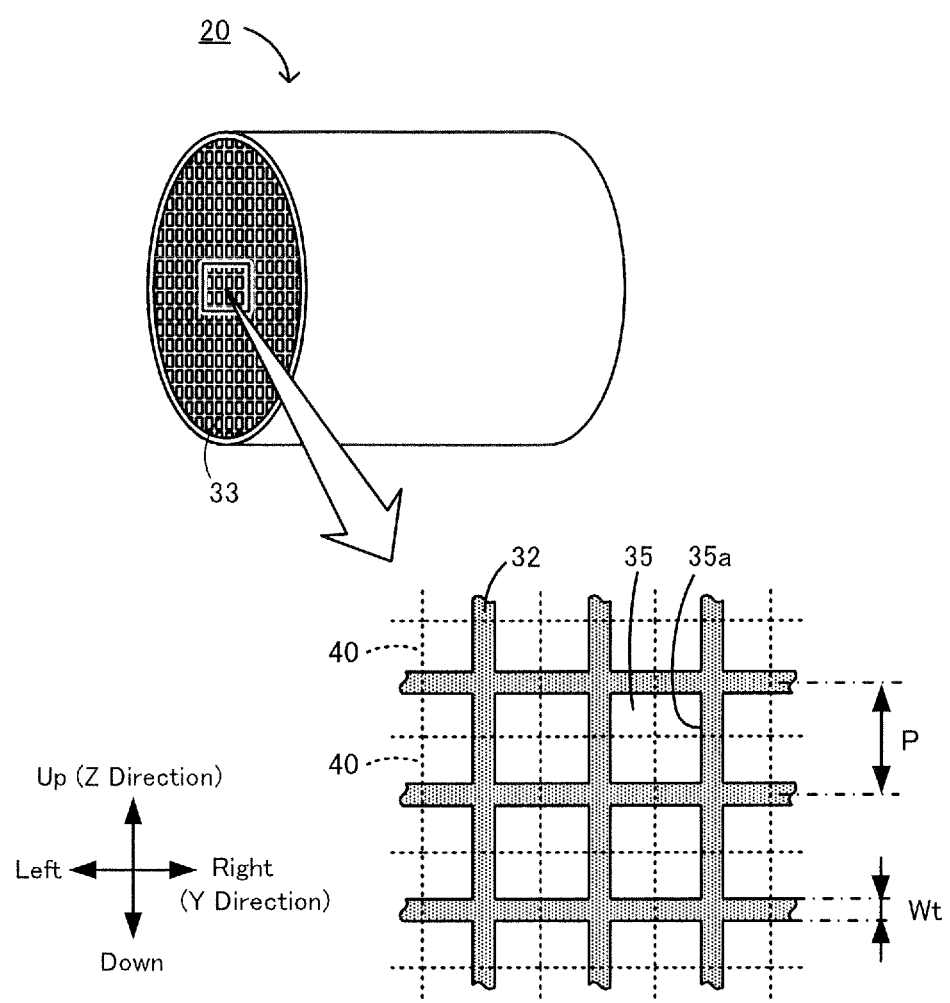
FIG. 5 is an explanatory view of the plurality of honeycomb meshes 40 arrayed in the YZ-directions.
Figure 6:
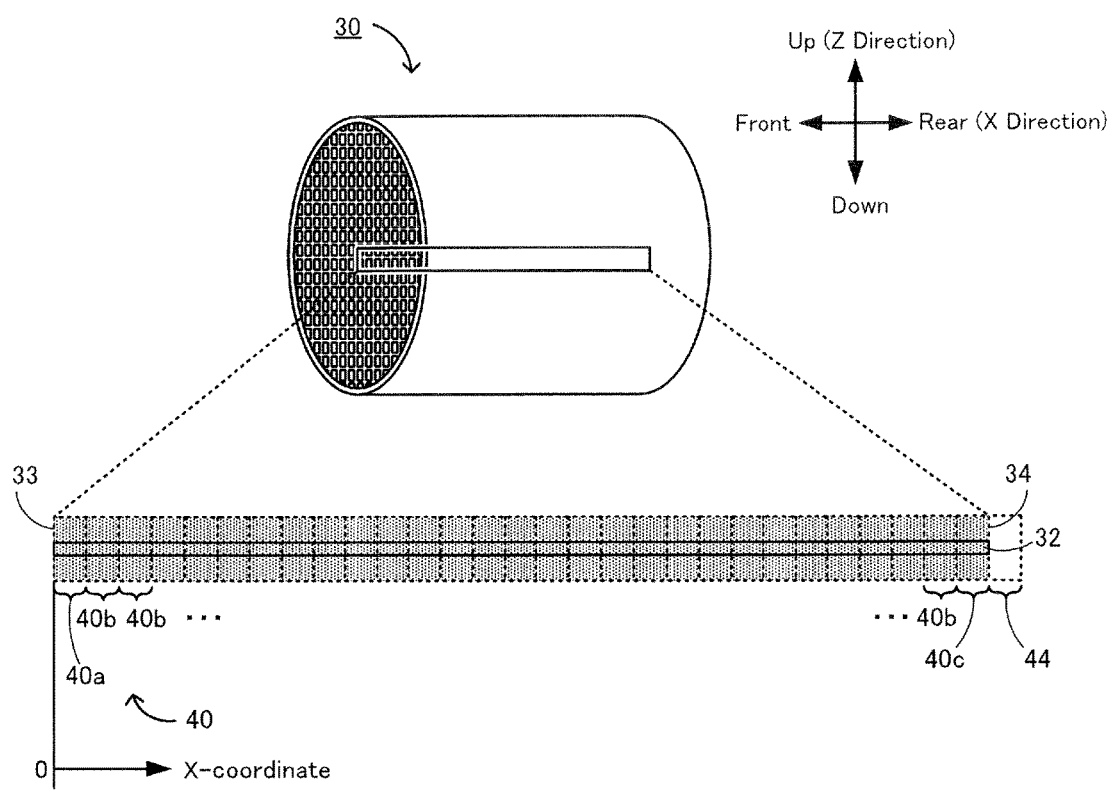
FIG. 6 is an explanatory view of the plurality of honeycomb meshes 40 arrayed in the X-direction.
Figure 7:
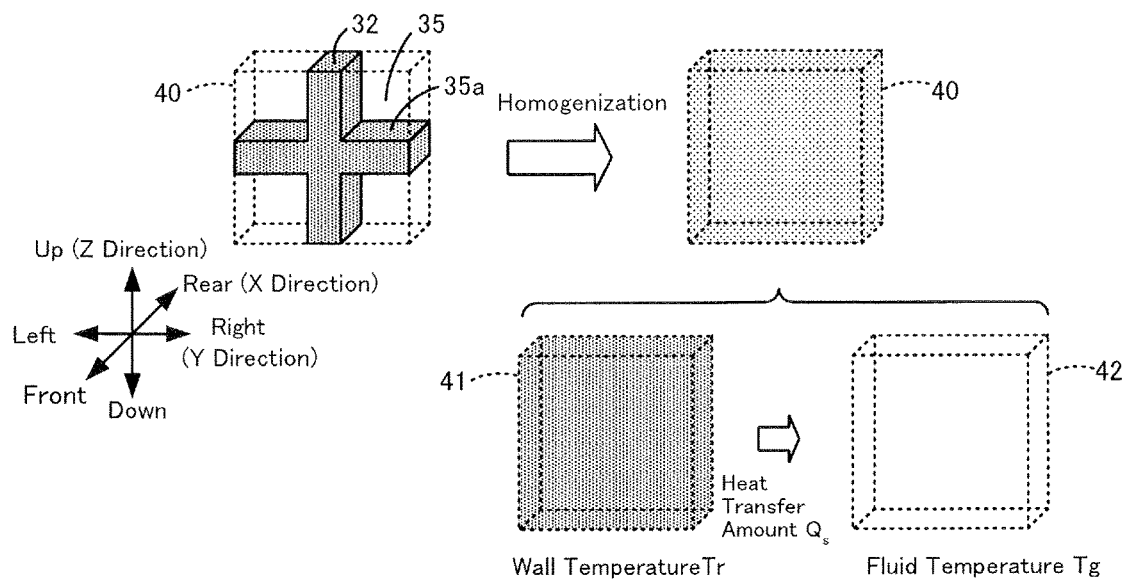
FIG. 7 is a conceptual view of the honeycomb meshes 40, the wall meshes 41, and the cell meshes 42.

The object information 20 stored in the HDD 15 of the analysis device 10 is information obtained by simulating the honeycomb structure 30, illustrated in FIGS. 2 and 3, with a plurality of honeycomb meshes 40 containing wall meshes 41 that represent the walls 32, and cell meshes 42 that represent the cells 35. FIG. 4 is a conceptual view representing one example of the object information 20. FIG. 5 is an explanatory view of the plurality of honeycomb meshes 40 arrayed in the YZ-directions. FIG. 6 is an explanatory view of the plurality of honeycomb meshes 40 arrayed in the X-direction. FIG. 7 is a conceptual view of the honeycomb meshes 40, the wall meshes 41, and the cell meshes 42.

The object information 20 contains information regarding the plurality of the honeycomb meshes 40. As illustrated in FIG. 4, various items of information regarding the honeycomb meshes 40 are set in correspondence to position information representing respective positions (XYZ-coordinates) of the honeycomb meshes 40. As illustrated in FIGS. 5 and 6, the honeycomb meshes 40 are arranged plural in each of the X-, Y- and Z-directions so as to simulate the honeycomb structure 30. FIG. 5 illustrates a manner of simulating a part of the front end surface 33 with the plurality of the honeycomb meshes 40, which are arranged in the YZ-directions as examples of the honeycomb meshes 40. Similarly, FIG. 6 illustrates a manner of simulating the cells 35 with the plurality of the honeycomb meshes 40, which are arranged in the X-direction (i.e., the fluid flowing direction within the cells 35). In this embodiment, the plurality of honeycomb meshes 40 are arranged in the YZ-directions such that, as illustrated in FIG. 5 and on the left side in FIG. 7, one honeycomb mesh 40 contains respective ¼ parts of four cells 35 adjacent to each other in the up-down direction and in the right-left direction, though not being particularly limited thereto. Thus, the honeycomb meshes 40 are each arranged such that one honeycomb mesh contains a region of one cell 35 (i.e., a region of ¼×four cells 35). Therefore, an up-down length and a right-left length of one honeycomb mesh 40 are equal to a cell pitch P of the cells 35 in the honeycomb structure 30. Moreover, respective lengths of the plural honeycomb meshes 40 in the front-rear direction are the same (e.g., ¹⁄₁₀₀ of a length of the cell 35 in the front-rear direction). Arranging the plurality of honeycomb meshes 40 as described above is preferable in that the meshes as many as possible among the plurality of honeycomb meshes 40 contained in the object information 20 are constituted so as to simulate the same structural configuration in the honeycomb structure 30. In this embodiment, as illustrated in FIGS. 5 and 6, the plurality of honeycomb meshes 40 except for the honeycomb meshes 40 simulating regions, which contain an outer peripheral surface of the honeycomb structure 30, are given as meshes simulating the same structural configuration as that of the honeycomb meshes 40 illustrated in FIGS. 5 and 6.

As illustrated in FIG. 6, the plurality of honeycomb meshes 40 arranged in the X-direction involve front end meshes 40a representing regions that contain the front end surface 33 of the honeycomb structure 30, rear end meshes 40c representing regions that contain the rear end surface 34, and intermediate meshes 40b representing the other regions. Information indicating to which one of the front end mesh 40a, the intermediate mesh 40b, and the rear end mesh 40c each honeycomb mesh 40 belongs is contained, as position type information, in the object information 20 in correspondence to each of the honeycomb meshes 40 (wall meshes 41), as indicated in FIG. 4.

Figure 8:
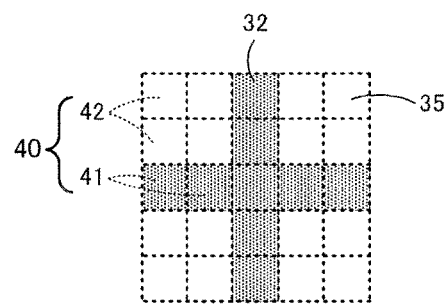
FIG. 8 is an explanatory view when using the wall meshes 41 that are not homogenized.

Furthermore, the plurality of honeycomb meshes 40 each serves as the wall mesh 41 representing the wall 32 and as the cell mesh 42 representing the cell 35 (space within the cell 35). In other words, one of the wall meshes 41 and the cell mesh 42 doubles as the other. More specifically, the plurality of honeycomb meshes 40 are not arranged such that the wall meshes 41 represent only the walls 32 and the cell meshes 42 represent only the cells 35 as illustrated in FIG. 8, by way of example. Instead, as illustrated on the left side in FIG. 7, the plurality of honeycomb meshes 40 are arranged such that each honeycomb mesh 40 involves at least a part of the walls 32 of the honeycomb structure 30 and at least a part of the cells 35 thereof. Moreover, a region of the honeycomb structure 30, the region being involved in each of the plural honeycomb meshes 40, does not simulate a detailed structural configuration of the walls 32 or the cells 35 as illustrated in FIG. 8, and it simulates a state that the walls 32 in the relevant region are homogenized as illustrated on the right side in FIG. 7. As a result, the number of the honeycomb meshes 40 is reduced. Thus, since the honeycomb mesh 40 simulates the homogenized state of the walls 32 and serves as the wall mesh 41 and the cell mesh 42, a wall temperature Tr [° C.] at each time as information of the wall mesh 41 and a fluid temperature Tg [° C.] at each time as information of the fluid in the cell mesh 42 can be made correspondent to each of the honeycomb meshes 40 in an analysis process described later (see a lower right area in FIG. 7). Furthermore, as seen from FIGS. 5 and 6, the regions of each cell 35, which are contained in one honeycomb mesh 40, are not directly contacted with the walls 32 of the other honeycomb meshes 40, and heat transfer does not occur therebetween. Accordingly, for heat transmission through heat transfer between the wall mesh 41 and the cell mesh 42, it is just required to consider a heat transfer amount $Q_s$ [W] (see a lower right area in FIG. 7) between the wall mesh 41 and the cell mesh 42 within the same honeycomb mesh 40.

As described above, each honeycomb mesh 40 simulates the homogenized state, and it does not simulate a detailed structural configuration of the wall 32 or the cell 35 as illustrated in FIG. 8. Instead, structural information, i.e., information regarding structural configuration of the wall 32 or the cell 35, is stored as the object information 20 in correspondence to each honeycomb mesh 40. In this embodiment, as indicated in FIG. 4, a cell pitch P [m], a wall thickness Wt [m] (see FIG. 5), and an end-surface heat transmission area $A_e$ [m²] are stored as the structural information in correspondence to each of the plural wall meshes 41, and a hydraulic diameter $d_h$ [m] and an inner-wall-surface heat transmission area $A_s$ [m²] of the cell 35 are stored as the structural information in correspondence to each of the plural cell meshes 42.

The end-surface heat transmission area $A_e$ is a total area of end surfaces of regions of the walls 32, which are contained in one wall mesh 41. The end-surface heat transmission area $A_e$ is assigned with a value in correspondence to the wall mesh 41 representing any of the front end mesh 40a and the rear end mesh 40c, and is not assigned with a value for the wall mesh 41 representing the intermediate mesh 40b that does not have the end surface. A sign "-" in FIG. 4 means that no value is assigned in correspondence. In this embodiment, the end-surface heat transmission areas $A_e$ of the front end mesh 40a and the rear end mesh 40c are each set to an area of the front surfaces (=area of the rear surfaces) of the walls 32 illustrated in FIG. 7. From the viewpoint of increasing the analysis accuracy, however, the end-surface heat transmission areas $A_e$ of the front end mesh 40a and the rear end mesh 40c, which are positioned at locations including the outer peripheral surface of the honeycomb structure 30, are each preferably set to a different value from the above set value depending on shapes of the end surfaces of the walls 32 contained in each wall mesh 41. Like the end-surface heat transmission area $A_e$, the cell pitch P and the wall thickness Wt are also given with values in correspondence to only each of the wall meshes 41 representing the front end mesh 40a and the rear end mesh 40c, which have the end surfaces. Alternatively, the cell pitch P and the wall thickness wt may be given with values in correspondence to each of the wall meshes 41 representing the intermediate meshes 40b. In this embodiment, values of the cell pitch P and the wall thickness Wt are set respectively to the same values for all the wall meshes 41. However, the cell pitch P and the wall thickness Wt corresponding to the wall meshes 41, which are positioned at locations including the outer peripheral surface of the honeycomb structure 30, may be each set to a different value from that set for the other wall meshes depending on the shapes of the end surfaces of the walls 32 contained in each wall mesh 41. For example, the cell pitch P may be set to a smaller value than that for the other wall meshes.

The hydraulic diameter $d_h$ is a typical length of the cell 35, and it is a value derived from 4×(cross-sectional area of the cell 35)/(peripheral edge length of the cell 35). The inner-wall-surface heat transmission area $A_s$ is a total area of inner wall surfaces of the cells 35 (=boundary surfaces between the cells 35 and the walls 32) in a region involved in one cell mesh 42. In this embodiment, the hydraulic diameter $d_h$ and the inner-wall-surface heat transmission area $A_s$ are set to their respective values that are the same for all the cell meshes 42. Furthermore, since one cell mesh 42 has a size involving one cell 35 as illustrated in FIGS. 5 and 7, the inner-wall-surface heat transmission area $A_s$=(peripheral edge length of one cell 35)×(length of one cell mesh 42 in the X-direction). From the viewpoint of increasing the analysis accuracy, however, the hydraulic diameter $d_h$ and the inner-wall-surface heat transmission area $A_s$ of each of the cell meshes 42, which are positioned at locations including the outer peripheral surface of the honeycomb structure 30, are each preferably set to a different value from that set for the other cell meshes depending on shapes of the inner wall surfaces of the cells 35 in the region involved in each cell mesh 42.

Furthermore, the object information 20 contains physical property values of the walls 32 in correspondence to each of the plural wall meshes 41. In this embodiment, as illustrated in FIG. 4, a wall density $\rho_r$[kg/m³], a wall specific heat $Cp_r$ [J/(kg·K)], and a wall thermal conductivity $\lambda_r$ [W/(m·K)], which are respectively a density, a specific heat, and a thermal conductivity of the walls 32, are set in correspondence to each of the plural wall meshes 41 as the physical property values of the walls 32 in the region involved in the relevant wall mesh 41. Moreover, in this embodiment, since the walls are homogenized, a wall thermal conductivity $\lambda_{r1}$ in a cross-sectional direction (YZ-direction) of the cell 35 and a wall thermal conductivity $\lambda_{r2}$ in the flow-path direction (X-direction) of the cell 35 are separately defined as the wall thermal conductivity $\lambda_r$. It is to be noted that, in this embodiment, the wall mesh 41 represents the state that the walls 32 are homogenized. For example, as illustrated in FIG. 7, the wall mesh 41 is set on an assumption that the cells 35 surrounded by the walls 32 are also parts of the walls (namely, a rectangular parallelepiped of the wall mesh 41 is entirely assumed to be a homogenous wall). Accordingly, among the physical property values of the walls 32, the wall density $\rho_r$ and the wall thermal conductivity $\lambda_r$ (including the wall thermal conductivity $\lambda_{r1}$ and the wall thermal conductivity $\lambda_{r2}$) are given as values obtained by modifying the actual physical property values of the walls 32 corresponding to the homogenization. More specifically, the wall density $\rho_r$=(actual density of the walls 32)×(volume of a portion of the actual walls 32, the portion being involved in one wall mesh 41)/(volume of one wall mesh 41) is used. The wall thermal conductivity $\lambda_{r1}$ in the cross-sectional direction is given as the wall thermal conductivity $\lambda_{r1}$=(actual thermal conductivity of the walls 32)×(wall thickness Wt)/(cell pitch P). The wall thermal conductivity $\lambda_{r2}$ in the flow-path direction is given as the wall thermal conductivity $\lambda_{r2}$=(cross-sectional area of a portion of the actual walls 32 in a YZ-plane, the portion being involved in one wall mesh 41)/(cross-sectional area of one wall mesh 41 in the YZ-plane). Here, the "cross-sectional area of a portion of the actual walls 32 in a YZ-plane, the portion being involved in one wall mesh 41" corresponds to a value obtained by subtracting a cross-sectional area of the cell 35 in the YZ-plane from the "cross-sectional area of one wall mesh 41 in the YZ-plane". In this embodiment, the wall density $\rho_r$, the wall specific heat $Cp_r$, and the wall thermal conductivities $\lambda_{r1}$ and $\lambda_{r2}$ are set to their respective values that are the same for all the wall meshes 41. From the viewpoint of increasing the analysis accuracy, however, the wall density $\rho_r$, the wall specific heat $Cp_r$, and the wall thermal conductivities $\lambda_{r1}$ and $\lambda_{r2}$ of each of the wall meshes 41, which are positioned at locations including the outer peripheral surface of the honeycomb structure 30, are each preferably set to a different value from that set for the other wall meshes depending on shapes and materials of the walls 32 in the region involved in each wall mesh 41.

Figure 9:
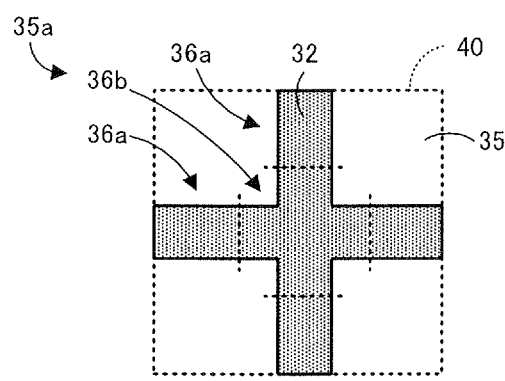
FIG. 9 is an explanatory view of flat portions 36a and corner portions 36b in one honeycomb mesh 40.

The object information 20 further contains shape information regarding shapes of inner wall surfaces 35a of the cells 35 in correspondence to each of the plural cell meshes 42. In this embodiment, as illustrated in FIG. 4, cell shape information representing cross-sectional shapes of the inner wall surfaces 35a of the cells 35, and information regarding weights of plural shape elements representing the inner wall surfaces 35a of the cells 35 are set as the shape information in correspondence to each of the cell meshes 42. The cell shape information is information regarding an entire cross-sectional shape of the cells 35 represented by each cell mesh 42. In this embodiment, the cell shape information is given as information indicating whether the cross-sectional shape is rectangular or hexagonal. Because the cells 35 are all assumed to be rectangular in this embodiment, the cell shape information corresponding to each cell mesh 42 is information representing that the cell shape is rectangular. The shape element provides information representing a part of the shapes of the inner wall surfaces 35a of the cells 35 indicated by each cell mesh 42. In this embodiment, the shape of each inner wall surface 35a is represented by a combination of two shape elements, i.e., a flat portion and a corner portion, and respective weights K1 and K2 of the two shape elements. FIG. 9 is an explanatory view of flat portions 36a and corner portions 36b in one honeycomb mesh 40 (cell mesh 42). By defining a portion of the inner wall surface 35a of the cell 35 near a corner as the corner portion 36b and the other portion of the inner wall surface 35a as the flat portion 36a, as illustrated in FIG. 9, the inner wall surface 35a can be expressed by a combination of the flat portion 36a and the corner portion 36b. The weight K1 of the flat portion 36a and the weight K2 of the corner portion 36b can also be said as values regarding proportions at which the flat portion 36a and the corner portion 36b occupy in the inner-wall-surface heat transmission area $A_s$. The weight K1 of the flat portion 36a and the weight K2 of the corner portion 36b can be set with experiments, for example, in order to increase the analysis accuracy described later. In this embodiment, the weight K1 of the flat portion 36a is set to a value 0.3, and the weight K2 of the corner portion 36b is set to a value 0.7, though not being particularly limited thereto, as illustrated in FIG. 4. It is to be noted that the corner portion 36b may be a corner having a curved surface.

In FIG. 4 and the above description, the structural information (i.e., the cell pitch P, the wall thickness Wt, and the end-surface heat transmission area $A_e$), the physical property values, and the position types are set in correspondence to each wall mesh 41 of the honeycomb meshes 40, whereas the structural information (i.e., the hydraulic diameter $d_h$ and the inner-wall-surface heat transmission area $A_s$) and the shape information are set in correspondence to each cell mesh 42. In this embodiment, however, the honeycomb mesh 40 serves as the wall mesh 41 and the cell mesh 42, and the wall mesh 41 and the cell mesh 42 correspond to each other in a one-to-one relation. Therefore, the information set in correspondence to one of the wall mesh 41 and the cell mesh 42 can be regarded as the information set in correspondence to the other. While the structural information and the shape information in correspondence to the cell mesh 42 have been described above as being separated from each other, the shape information may be handled as part of the structural information.

The object information 20 may contain other information than that illustrated in FIG. 4. The object information 20 in this embodiment contains information (such as position information) of space meshes 44 (see FIG. 6) representing spaces that are in contact with respective rear surfaces of the plural rear end meshes 40c. The information of the space meshes 44 is used in the analysis process, described below, to derive a heat transfer amount between the rear end surface of the rear end mesh 40c (i.e., a region corresponding to a part of the rear end surface 34) and the fluid. The object information 20 in this embodiment further contains information regarding respective sizes (dimensions in the XYZ-directions) of the plural honeycomb meshes 40 and the plural space meshes 44. The object information 20 may contain information regarding a diameter of the entire honeycomb structure 30 and a length thereof in the front-back direction.

Figure 10:
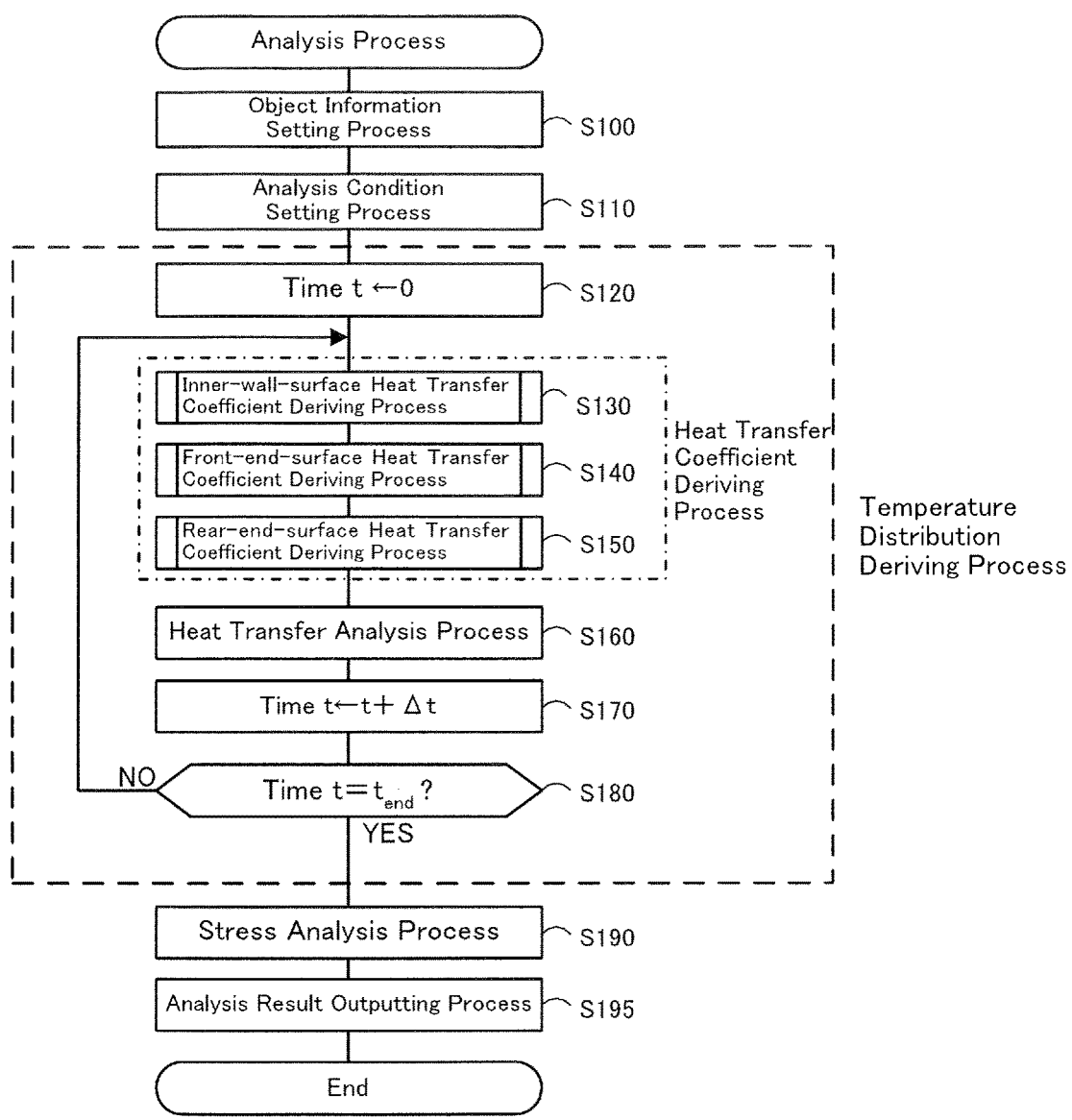
FIG. 10 is a flowchart illustrating one example of an analysis process routine.

The analysis process executed by the analysis device 10 will be described below. The analysis process is to analyze the state of the honeycomb structure 30 after the lapse of a predetermined time from an analysis start time when the honeycomb structure 30 is exposed to the fluid. FIG. 10 is a flowchart illustrating one example of an analysis process routine. When a user instructs the start of the analysis process through the input device 17, the analysis process routine is started by the CPU 12 executing the analysis processing program that is stored in the HDD 15.

When the analysis processing routine is executed, the CPU 12 first executes an object information setting process for setting information of an object to be analyzed in the analysis process (step S100). In this process, the CPU 12 receives an instruction of analyzing the object information 20 from the user through the input device 17, and sets the object information 20 as the object of the analysis process in accordance with the received instruction. Alternatively, other sets of object information may be stored in the HDD 15 in addition to the object information 20, and the CPU 12 may receive a select instruction indicating which object information is to be analyzed, from the user through the input device 17. While the object information 20 is previously stored in the HDD 15 in this embodiment, the CPU 12 may obtain the object information 20 from, e.g., an external storage medium readable by the analysis device 10, or from another computer, may store the obtained object information 20 in the HDD 15, and may set the stored object information 20 as the analysis object. Furthermore, the CPU 12 may receive an instruction of changing data, which is contained in the object information 20 stored in the HDD 15, from the user through the input device 17, and may change the data of the object information 20 in accordance with the received instruction. The following description is made while referring to FIG. 4 in connection with the case where the above-described object information 20 is set as the object of the analysis process.

After step S100, the CPU 12 executes an analysis condition setting process for setting analysis conditions (step S110). For example, the CPU 12 sets, as the analysis conditions, information previously stored in the HDD 15, or information received from the user through the input device 17. In this embodiment, fluid inflow conditions, conditions for fluid physical property values, initial conditions, boundary conditions, etc. are set as the analysis conditions. The fluid inflow conditions are set as information regarding a temperature (fluid temperature Tg) and a flow rate V [m$^3$/s] of the fluid flowing into the honeycomb structure 30 at each time from an analysis start time (time t=0) to an analysis end time (time t=$t_{end}$) after the lapse of a predetermined time. It is here assumed that the fluid flows into the front end surface 33 of the honeycomb structure 30 perpendicularly from the front side of the front end surface 33, and that the temperature and the flow rate V of the inflow fluid (i.e., the fluid incoming from the front side of the front end surface 33 of the honeycomb structure 30) vary with the lapse of time from the analysis start time. The fluid inflow conditions may contain not only the information regarding changes of the temperature and the flow rate V depending on time, but also information regarding changes of the temperature and the flow rate V depending on positions in the YZ-plane. For example, the temperature and the flow rate V of the inflow fluid may be each different between a central region of the front end surface 33 and a peripheral region near its outer peripheral surface even at the same time.

The conditions for the fluid physical property values are set as information regarding conditions for the values of the fluid physical properties, such as a fluid density $\rho_g$ [kg/m$^3$], a fluid specific heat $Cp_g$ [J/(kg·K)], and a fluid thermal conductivity $\lambda_g$ [W/(m·K)], which are respectively a density, a specific heat, and a thermal conductivity of the fluid. In this embodiment, the fluid density $\rho_g$, the fluid specific heat $Cp_g$, and the fluid thermal conductivity $\lambda_g$ are each given as a value that varies depending on the fluid temperature Tg. Accordingly, in step S110, the CPU 12 uses, as the conditions for the fluid physical property values, information (e.g., relational equations or maps) that enables the fluid density $\rho_g$, the fluid specific heat $Cp_g$, and the fluid thermal conductivity $\lambda_g$ to be derived on the basis of the fluid temperature Tg.

The initial conditions are provided as information representing the state of the honeycomb structure 30 at the analysis start time. In this embodiment, the initial conditions are provided as a value of the wall temperature Tr of each honeycomb mesh 40 in the object information 20 at the analysis start time, and as a value of the fluid temperature Tg for each of the fluid in the cell mesh 42 and the fluid in the space mesh 44 at the analysis start time.

The boundary conditions are, for example, a heat transmission boundary condition at each of the front end surface 33 and the rear end surface 34 of the honeycomb structure 30, and a heat transmission boundary condition at the outer peripheral surface of the honeycomb structure 30. In this embodiment, conditions regarding radiations from the front end surface 33 and the rear end surface 34, and a condition regarding the heat transfer coefficient or the heat transfer amount from the outer peripheral surface of the honeycomb structure 30 to engine piping are used as the boundary conditions.

Figure 11:
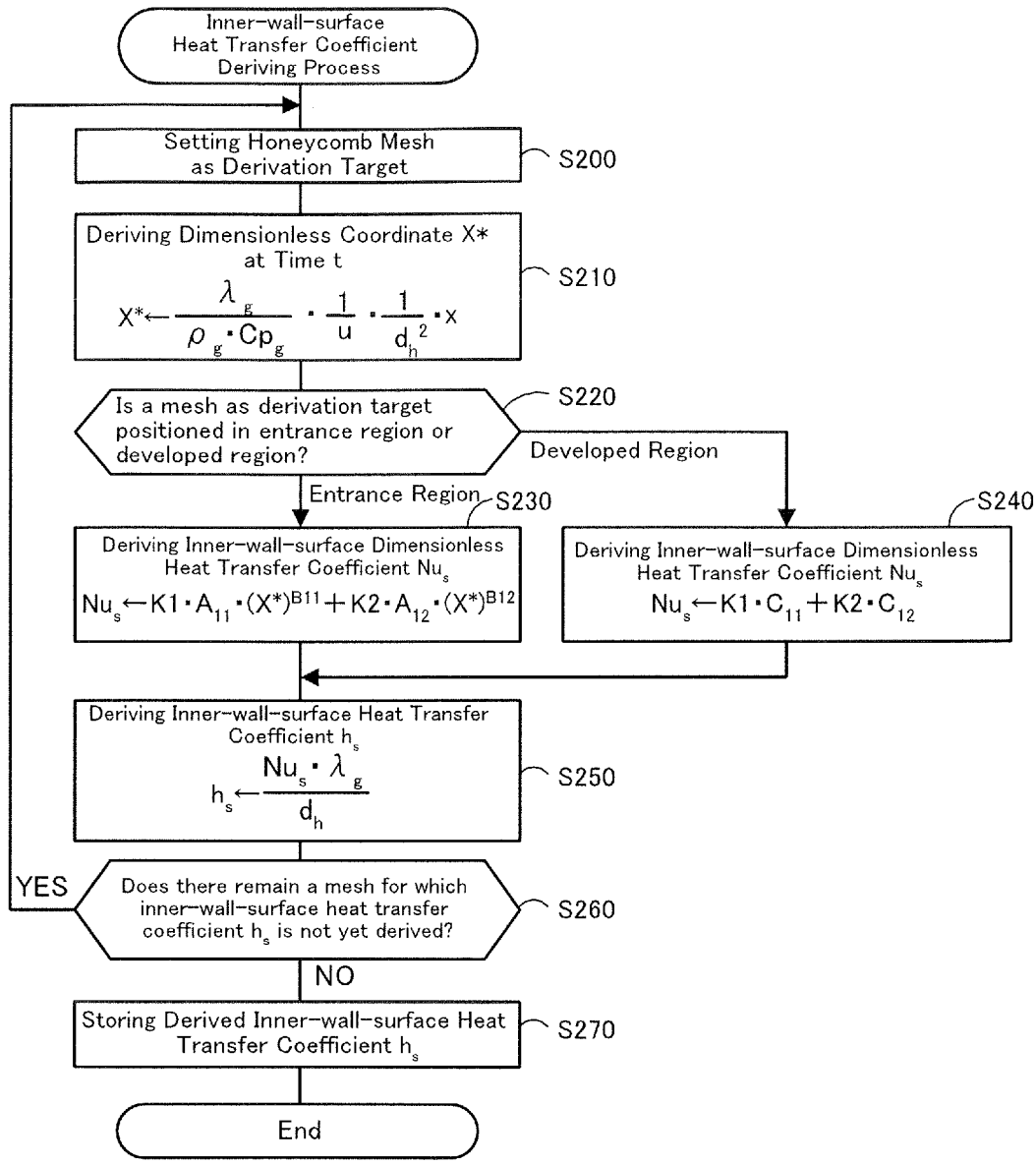
FIG. 11 is a flowchart illustrating one example of the inner-wall-surface heat transfer coefficient deriving process.

After step S110, the CPU 12 executes processing (temperature distribution deriving process) of steps S120 to S180. The CPU 12 executes the temperature distribution deriving process while, as required, reading and obtaining (referring to) the object information 20 stored in the HDD 15. A process of obtaining the object information 20 in the temperature distribution deriving process corresponds to an object information obtaining process in the present invention. Upon the start of the temperature distribution deriving process, the CPU 12 first sets a current time t to the analysis start time (value 0) (step S120). Then, the CPU 12 executes processing (heat transfer coefficient deriving process) of steps S130 to S150 to derive various heat transfer coefficients between the walls 32 of the honeycomb meshes 40 and the fluid. In the heat transfer coefficient deriving process, the CPU 12 first executes an inner-wall-surface heat transfer coefficient deriving process for deriving an inner-wall-surface heat transfer coefficient $h_s$ that is a heat transfer coefficient between the wall mesh 41 and the cell mesh 42, and that is a heat transfer coefficient between the wall 32 and the fluid inside the cell 35 through the inner wall surface 35a (step S130). FIG. 11 is a flowchart illustrating one example of the inner-wall-surface heat transfer coefficient deriving process.

Upon the start of the inner-wall-surface heat transfer coefficient deriving process, the CPU 12 first sets, from among the plural meshes, the wall mesh 41 and the cell mesh 42 as a derivation target for which the inner-wall-surface heat transfer coefficient is to be derived (step S200). From among combinations of the wall meshes 41 and the cell meshes 42 causing heat transfer therebetween through the inner wall surface 35a, the CPU 12 selects and sets one combination of both the meshes as the target for derivation of the inner-wall-surface heat transfer coefficient. In this embodiment, since the honeycomb mesh 40 serves as the wall mesh 41 and the cell mesh 42 as described above, heat transfer between the wall mesh 41 and the cell mesh 42 is generated only between the wall mesh 41 and the cell mesh 42 in the same honeycomb mesh 40. Accordingly, in this embodiment, the wall mesh 41 and the cell mesh 42 as the target for the derivation are set by setting one of the plural honeycomb meshes 40 as the derivation target.

Then, on the basis of position information of the honeycomb mesh 40 set as the derivation target in step S200 and fluid state information regarding the state of the fluid in the cell mesh 42 set as the derivation target at the time t, the CPU 12 derives a dimensionless coordinate X* of the honeycomb mesh 40 as the derivation target at the time t (step S210). In this embodiment, the dimensionless coordinate X* is derived from a relation of the following equation (5) on the basis of an X-coordinate value x [m] as the position information of the honeycomb mesh 40, and the fluid state information, i.e., the flow velocity u [m/s], the fluid density $\rho_g$ [kg/m$^3$], the fluid specific heat $Cp_g$ [J/(kg·K)], and the fluid thermal conductivity $\lambda_g$ [W/(m·K)] of the fluid, at the time t, and the hydraulic diameter $d_h$ [m] set in the object information 20 in correspondence to the honeycomb mesh 40 set as the derivation target. The dimensionless coordinate X* expressed by the equation (5) is also called the Graetz number.

$$X^* = (\lambda_g/(\rho_g \times Cp_g)) \times (1/u) \times (1/d_h^2) \times x \qquad \text{Eq. (5)}$$

Because the fluid density $\rho_g$, the fluid specific heat $Cp_g$, and the fluid thermal conductivity $\lambda_g$ are values varying depending on the fluid temperature Tg as described above, respective values derived depending on the fluid temperature Tg at the time t are used. At the time t=0, a value contained in the above-described initial conditions is used as the value of the fluid temperature Tg. In the case except for the time t=0, a value derived in a heat transfer analysis process of step S160 described later is used as the value of the fluid temperature Tg. The flow velocity u is derived from the flow rate V of the fluid at the time t, the flow rate V being contained in the fluid inflow conditions set in step S100. More specifically, the flow rate V of the fluid corresponding to the YZ-coordinates of the cell mesh 42 as the derivation target at the time t, i.e., the flow rate V indicating a flow rate of the fluid flowing into an inlet (front end surface 33) of the cell 35 represented by the cell mesh 42 as the derivation target, is obtained on the basis of the set fluid inflow conditions. Then, from a relation of the flow velocity u=V/S, the flow velocity u is derived on the basis of the obtained flow rate V and a cross-sectional area S (cross-sectional area of a section parallel to the YZ-plane, i.e., cross-sectional area of a section perpendicular to the fluid flowing direction) of the cell 35 represented by the cell mesh 42 as the derivation target. In this embodiment, it is assumed that a value of the cross-sectional area S of the cell 35 is the same for all the cells 35 and is previously contained in the object information 20. The cross-sectional area S may be set in the object information 20 in correspondence to each cell mesh 42 as one item of the structural information. In such a case, the plural cell meshes 42 may include the cell meshes 42 having different cross-sectional areas S assigned in correspondence thereto. For example, the cell meshes 42 representing the cells 35 at the outermost periphery of the honeycomb structure 30 may be each assigned in correspondence with a different value of the cross-sectional area S from that assigned to the other cell meshes 42.

In this embodiment, the fluid density $\rho_g$, the fluid specific heat $Cp_g$, the fluid thermal conductivity $\lambda_g$, and the flow velocity u in the equation (5) are all values varying depending on the time t. In other words, the CPU 12 derives the dimensionless coordinate X* as a value in consideration of the state of the fluid in the cell mesh 42, the state varying depending on a value of the current time t.

After deriving the dimensionless coordinate X*, the CPU 12 executes processing of steps S220 to S240 and derives an inner-wall-surface dimensionless heat transfer coefficient $Nu_s$, i.e., a dimensionless value of the inner-wall-surface heat transfer coefficient $h_s$ that is the heat transfer coefficient between the inner wall surface 35a of the cell 35 in the honeycomb mesh 40 as the derivation target and the fluid. A dimensionless heat transfer coefficient (inner-wall-surface dimensionless heat transfer coefficient $Nu_s$ here) is also called the Nusselt number. The CPU 12 executes the processing of steps S220 to S240 while reading and obtaining (referring to) the inner-wall-surface dimensionless correspondence information 23 stored in the HDD 15. A process of obtaining the inner-wall-surface dimensionless correspondence information 23 in steps S220 to S240 corresponds to an inner-wall-surface dimensionless correspondence information obtaining process in the present invention.

Figure 12:
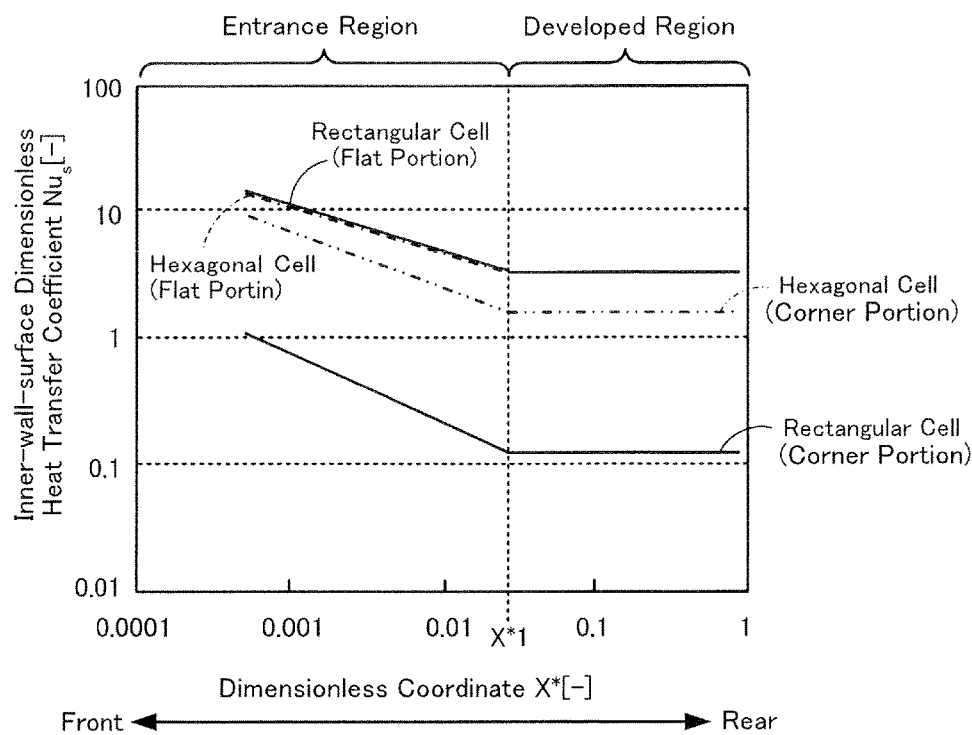
FIG. 12 is a conceptual view of the inner-wall-surface dimensionless correspondence information 23.

The inner-wall-surface dimensionless correspondence information 23 is described here. FIG. 12 is a conceptual view of the inner-wall-surface dimensionless correspondence information 23 stored in the HDD 15. The inner-wall-surface dimensionless correspondence information 23 is information regarding a correspondence relation between the dimensionless coordinate X* and the inner-wall-surface dimensionless heat transfer coefficient $Nu_s$. An upper column in FIG. 12 denotes the correspondence relation in the form of a graph (map), and a lower column denotes the correspondence relation by equations. As illustrated in FIG. 12, the correspondence relation, contained in the inner-wall-surface dimensionless correspondence information 23, between the dimensionless coordinate X* and the inner-wall-surface dimensionless heat transfer coefficient $Nu_s$ contains information regarding the correspondence relation that is different depending on whether the dimensionless coordinate X* is positioned in a fluid entrance region or a fluid developed region. More specifically, the inner-wall-surface dimensionless correspondence information 23 contains, as the correspondence relation between the dimensionless coordinate X* and the inner-wall-surface dimensionless heat transfer coefficient $Nu_s$ in the entrance region, information regarding the correspondence relation expressed by the following equation (1). The inner-wall-surface dimensionless correspondence information 23 further contains, as the correspondence relation between the dimensionless coordinate X* and the inner-wall-surface dimensionless heat transfer coefficient $Nu_s$ in the developed region, information regarding the correspondence relation expressed by the following equation (2). As seen from FIG. 12, when the dimensionless coordinate X* is positioned in the entrance region, the inner-wall-surface dimensionless heat transfer coefficient $Nu_s$ tends to decrease as the dimensionless coordinate X* increases. When the dimensionless coordinate X* is positioned in the developed region, the inner-wall-surface dimensionless heat transfer coefficient $Nu_s$ corresponding to any value of the dimensionless coordinate X* is a constant value. Assuming the dimensionless coordinate X* at a boundary between the entrance region and the developed region to be a dimensionless coordinate X*1, the dimensionless coordinate X*1=0.031 is given in this embodiment.

$$Nu_s = A \times (X^*)B \qquad \text{Eq. (1)}$$

(where $Nu_s$: inner-wall-surface dimensionless heat transfer coefficient, X*: dimensionless coordinate, and A, B: coefficients)

$$Nu_s = C \qquad \text{Eq. (2)}$$

(where $Nu_s$: inner-wall-surface dimensionless heat transfer coefficient, and C: coefficient)

The inner-wall-surface dimensionless correspondence information 23 further contains the correspondence relation that is different for each shape and each shape element of the inner wall surface 35a of the cell 35 in the honeycomb mesh 40 as the derivation target. Thus, as indicated in the lower column in FIG. 12, the coefficients A to C in the above equations (1) and (2) are set for each shape and each shape element of the inner wall surface 35a. More specifically, assuming that the coefficients A to C in the case of the cell shape information being rectangular and the shape element being the flat portion are denoted by coefficients $A_{11}$, $B_{11}$ and $C_{11}$, respectively, the coefficient $A_{11}=0.9$, the coefficient $B_{11}=-0.4$, and the coefficient $C_{11}=3.2$ are set. Assuming that the coefficients A to C in the case of the cell shape information being rectangular and the shape element being the corner portion are denoted by coefficients $A_{12}$, $B_{12}$ and $C_{12}$, respectively, the coefficient $A_{12}=0.01$, the coefficient $B_{12}=-0.6$, and the coefficient $C_{12}=0.1$ are set. Assuming that the coefficients A to C in the case of the cell shape information being hexagonal and the shape element being the flat portion are denoted by coefficients $A_{21}$, $B_{21}$ and $C_{21}$, respectively, the coefficient $A_{21}=0.7$, the coefficient $B_{21}=-0.4$, and the coefficient $C_{21}=3.2$ are set. Assuming that the coefficients A to C in the case of the cell shape information being hexagonal and the shape element being the corner portion are denoted by coefficients $A_{22}$, $B_{22}$ and $C_{22}$, respectively, the coefficient $A_{22}=0.2$, the coefficient $B_{22}=-0.5$, and the coefficient $C_{22}=1.6$ are set. As seen from FIG. 12, in this embodiment, the coefficients C ($C_{11}$, $C_{21}$) corresponding to the flat portion in the developed region are set to the same value regardless whether the cell shape is rectangular or hexagonal. This is attributable to the fact that the shape of the inner wall surface 35a is grouped into the shape elements representing the corner portion and the flat portion, and that the heat transfer near the flat portion is not affected by the cell shape.

The correspondence relation between the dimensionless coordinate X* and the inner-wall-surface dimensionless heat transfer coefficient $Nu_s$, illustrated in FIG. 12, can be obtained, for example, as follows. First, an object constituted only by one cell and walls around the cell is prepared as a test target, and a relation between an X-coordinate and a heat transfer coefficient is determined with experiments or simulations. More specifically, the relation therebetween is determined, for example, as follows. First, thermal hydraulic calculations are executed on the above test target to determine a temperature distribution of the fluid, a temperature distribution of the wall, and a distribution of heat flux between the fluid and the wall. The relation between the X-coordinate and the heat transfer coefficient is determined by calculating the heat transfer coefficient corresponding to each X-coordinate from a relation of the heat flux q [W/m$^2$]=heat transfer coefficient [W/(m$^2$·K)]×(fluid temperature [° C.]–wall temperature [° C.]). In the case of separately determining the relations between the X-coordinate and the heat transfer coefficients for the flat portion and the corner portion, those relations can be determined by respectively employing a relation of (heat flux q [W/m$^2$] passing through the flat portion)=(heat transfer coefficient [W/(m$^2$·K)] in the flat portion)×(fluid temperature [° C.]–wall temperature [° C.] of the flat portion) and a relation of (heat flux q [W/m$^2$] passing through the corner portion)= (heat transfer coefficient [W/(m$^2$·K)] in the corner portion× (fluid temperature [° C.]–wall temperature [° C.] of the corner portion). The fluid temperature in the above is preferably given as a temperature at the center of the cell or an average temperature in the cross-section of the cell. Which region of the inner wall surface of the cell as the test target is regarded as the flat portion or the corner portion (namely, a position where a boundary between the flat portion and the corner portion is to be set) can be determined optionally. Proportions of the flat portion and the corner portion determined in the above can be directly used as the above-mentioned weight K1 of the flat portion and the above-mentioned weight K2 of the corner portion. The correspondence relation between the dimensionless coordinate X* and the inner-wall-surface dimensionless heat transfer coefficient $Nu_s$ is obtained by converting the X-coordinate and the heat transfer coefficient, which are obtained as described above, to dimensionless values (note that a relation between a heat transfer coefficient and a dimensionless heat transfer coefficient will be described later).

Values of the coefficients A to C are not limited to the above-mentioned values. For example, though not being particularly limited to the following, the coefficient $A_{11}$ may be set to a value within the range of 0.8 to 1.0, the coefficient $B_{11}$ may be set to a value within the range of –0.45 to –0.35, and the coefficient $C_{11}$ may be set to a value within the range of 3.0 to 3.4. The coefficient $A_{12}$ may be set to a value within the range of 0.01 to 0.02, the coefficient $B_{12}$ may be set to a value within the range of –0.65 to –0.55, and the coefficient $C_{12}$ may be set to a value within the range of 0.09 to 0.14. The coefficient $A_{21}$ may be set to a value within the range of 0.5 to 0.9, the coefficient $B_{21}$ may be set to a value within the range of –0.45 to –0.35, and the coefficient $C_{21}$ may be set to a value within the range of 3.0 to 3.4. The coefficient $A_{22}$ may be set to a value within the range of 0.2 to 0.3, the coefficient $B_{22}$ may be set to a value within the range of –0.55 to –0.45, and the coefficient $C_{22}$ may be set to a value within the range of 1.5 to 1.7. A value of the dimensionless coordinate X*1 at the boundary between the entrance region and the developed region is also not limited to the above-mentioned value, and it may be set to a value within the range of 0.01 to 0.04, for example. In addition, the inner-wall-surface dimensionless correspondence information 23 may be information representing the correspondence relation in the form of the graph (map) as denoted in the upper column in FIG. 12, or information representing the correspondence relation by the equations and the coefficients as denoted in the lower column in FIG. 12. The following description is made in connection with the case where the correspondence relation is expressed by the equations and the coefficients.

After deriving the dimensionless coordinate X* in step S210, the CPU 12 determines, on the basis of the derived dimensionless coordinate X* and the inner-wall-surface dimensionless correspondence information 23, whether the honeycomb mesh 40 as the derivation target is positioned in the entrance region or the developed region (step S220). If the CPU 12 determines that the relevant honeycomb mesh 40 is positioned in the entrance region, the CPU 12 derives the inner-wall-surface dimensionless heat transfer coefficient $Nu_s$ of the honeycomb mesh 40 as the derivation target by employing the correspondence relation in the entrance region, which is contained in the inner-wall-surface dimensionless correspondence information 23 (step S230). More specifically, the CPU 12 first derives the inner-wall-surface dimensionless heat transfer coefficient corresponding to each of the shape elements by employing the correspondence relation between the dimensionless coordinate X* and the inner-wall-surface dimensionless heat transfer coefficient $Nu_s$ in the entrance region, the relevant correspondence relation being specified on the basis of each cell shape and each shape element both contained in the shape information stored in correspondence to the honeycomb mesh 40 set as the derivation target. For example, the inner-wall-surface dimensionless heat transfer coefficient corresponding to the flat portion of the rectangular cell is derived as $A_{11} \times (X^*)^{B11}$ from the equation (1). The inner-wall-surface dimensionless heat transfer coefficient corresponding to the corner portion of the rectangular cell is derived as $A_{12} \times (X^*)^{B12}$ from the equation (1). Then, the CPU 12 weights the inner-wall-surface dimensionless heat transfer coefficient corresponding to each of the shape elements with the weight (i.e., the weight K1 for the flat portion or the weight K2 for the corner portion), which is set in the object information 20 in correspondence to the honeycomb mesh 40 as the derivation target, and derives the weighted sum of the individual inner-wall-surface dimensionless heat transfer coefficients after the weighting as the inner-wall-surface dimensionless heat transfer coefficient $Nu_s$ of the honeycomb mesh 40 as the derivation target. Thus, in step S230, the inner-wall-surface dimensionless heat transfer coefficient $Nu_s$ is derived from the following equation (6).

$$Nu_s = K1 \times A_{11} \times (X^*)^{B11} + K2 \times A_{12} \times (X^*)^{B12} \qquad \text{Eq. (6)}$$

On the other hand, if the CPU 12 determines from the dimensionless coordinate X* in step S220 that the honeycomb mesh 40 is positioned in the developed region, the CPU 12 derives the inner-wall-surface dimensionless heat transfer coefficient $Nu_s$ of the honeycomb mesh 40 as the derivation target by employing the correspondence relation in the developed region, which is contained in the inner-wall-surface dimensionless correspondence information 23 (step S240). In this process, the CPU 12 derives the weighted sum of individual inner-wall-surface dimensionless heat transfer coefficients after the weighting, as the inner-wall-surface dimensionless heat transfer coefficient $Nu_s$ in a similar manner to that in step S230 except for using the equation (2) instead of the equation (1). Thus, in step S240, the inner-wall-surface dimensionless heat transfer coefficient $Nu_s$ is derived from the following equation (7).

$$Nu_s = K1 \times C_{11} + K2 \times C_{12} \qquad \text{Eq. (7)}$$

After step S230 or S240, the CPU 12 derives, on the basis of the inner-wall-surface dimensionless heat transfer coefficient $Nu_s$ having been derived above, the inner-wall-surface heat transfer coefficient $h_s$ between the wall mesh 41 as the derivation target and the cell mesh 42 (step S250). In this embodiment, the inner-wall-surface heat transfer coefficient $h_s$ [W/(m²·K)] is derived from a relation of the following equation (8) on the basis of the inner-wall-surface dimensionless heat transfer coefficient $Nu_s$, the fluid thermal conductivity $\lambda_g$ [W/(m·K)] of the fluid in the cell mesh 42 as the derivation target, and the hydraulic diameter $d_h$ [m] set in the object information 20 in correspondence to the cell mesh 42 as the derivation target. The fluid thermal conductivity $\lambda_g$ and the hydraulic diameter $d_h$ may be given as their respective values that are the same as those used in step S210.

$$h_s = (Nu_s \times \lambda_g)/d_h \qquad \text{Eq. (8)}$$

After, as described above, executing steps S210 to S250 and deriving the inner-wall-surface heat transfer coefficient $h_s$ corresponding to the honeycomb mesh 40 as the derivation target, the CPU 12 determines whether there still remains the honeycomb mesh 40 for which the inner-wall-surface heat transfer coefficient $h_s$ is not yet derived (step S260). If there still remains the honeycomb mesh 40 for which the inner-wall-surface heat transfer coefficient $h_s$ is not yet derived, the CPU 12 executes the processing of step S200 to set the relevant honeycomb mesh 40 as the derivation target, and executes the processing subsequent to step S210. If the CPU 12 determines in step S260 that there remains no honeycomb mesh 40 for which the inner-wall-surface heat transfer coefficient $h_s$ is not yet derived, the CPU 12 stores the respective inner-wall-surface heat transfer coefficients $h_s$, which have been derived for the plural honeycomb meshes 40, in the HDD 15 in correspondence to the individual honeycomb meshes 40 (step S270), and brings the inner-wall-surface heat transfer coefficient deriving process to an end.

Thus, in this embodiment, the inner-wall-surface dimensionless correspondence information 23 is previously stored in the HDD 15, and the inner-wall-surface heat transfer coefficient $h_s$ of each honeycomb mesh 40 at an arbitrary time t is derived by employing the inner-wall-surface dimensionless correspondence information 23. Here, as illustrated in FIG. 12, the relation between the dimensionless coordinate X* and the inner-wall-surface dimensionless heat transfer coefficient $Nu_s$ can be expressed by the same correspondence relation regardless of the fluid state that varies over time. Accordingly, in this embodiment, the inner-wall-surface heat transfer coefficient $h_s$ (of which value is variable depending on the time t) reflecting the fluid state information at the time t is appropriately derived by utilizing the feature that the inner-wall-surface dimensionless heat transfer coefficient $Nu_s$ can be derived using the same correspondence relation by deriving the dimensionless coordinate on the basis of the fluid state information varying over time. Furthermore, in this embodiment, the inner-wall-surface heat transfer coefficient $h_s$ is derived with higher accuracy in consideration of the shape of the inner wall surface 35a by employing the correspondence relation depending on each cell shape and each shape element of the inner wall surface 35a.

While, in step S220, whether the honeycomb mesh 40 as the derivation target is positioned in the entrance region or the developed region is determined on the basis of the dimensionless coordinate X*, such determination is not needed when the inner-wall-surface dimensionless correspondence information 23 is given as information representing the correspondence relation in the form of the graph (map) as denoted in the upper column in FIG. 12. More specifically, the inner-wall-surface dimensionless heat transfer coefficient corresponding to each of the shape elements may be derived directly on the basis of the dimensionless coordinate X*, which has been derived in step S210, without specifically discriminating the dimensionless coordinate X* between the entrance region and the developed region, and the weighted sum of the individual inner-wall-surface dimensionless heat transfer coefficients after the weighting is derived as the inner-wall-surface dimensionless heat transfer coefficient $Nu_s$.

Figure 13:
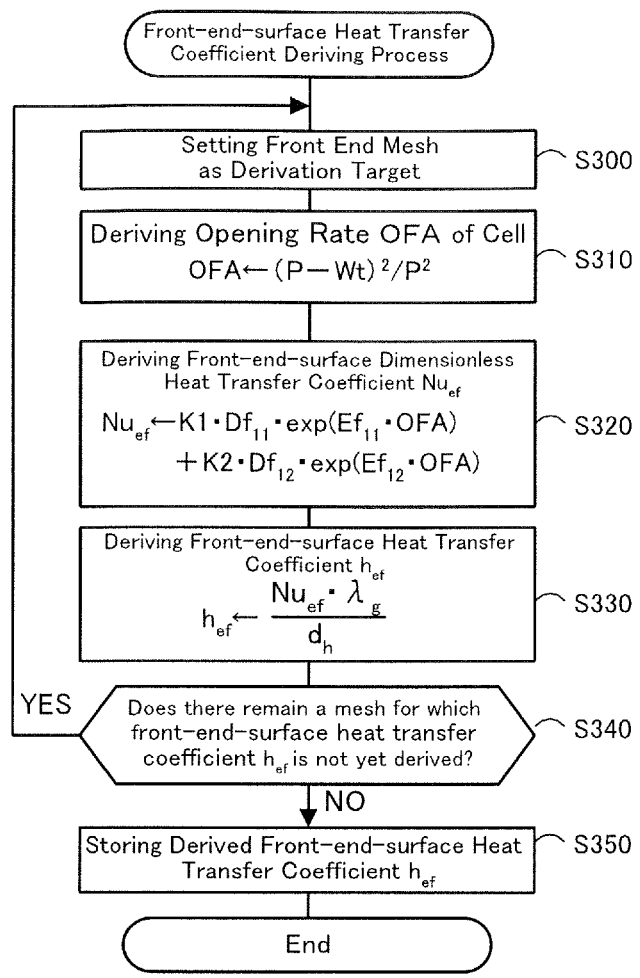
FIG. 13 is a flowchart illustrating one example of the front-end-surface heat transfer coefficient deriving process.

After executing the inner-wall-surface heat transfer coefficient deriving process of step S130 in FIG. 10 as described above, the CPU 12 executes a front-end-surface heat transfer coefficient deriving process for deriving a front-end-surface heat transfer coefficient $h_{ef}$ that is a heat transfer coefficient between the open end surface of the front end mesh 40a and the fluid (i.e., a heat transfer coefficient between a portion of the front end surface 33, the portion being involved in the front end mesh 40a, and the fluid) (step S140). FIG. 13 is a flowchart illustrating one example of the front-end-surface heat transfer coefficient deriving process.

Upon the start of the front-end-surface heat transfer coefficient deriving process, the CPU 12 first sets, from among the plural front end meshes 40a, one front end mesh 40a as a target for derivation of the front-end-surface heat transfer coefficient $h_{ef}$ (step S300). It is to be noted that the front end mesh 40a (particularly the wall mesh 41 thereof) corresponds to an end wall mesh in the present invention. Then, the CPU 12 derives, for the cell 35 represented by the front end mesh 40a as the derivation target, an opening rate OFA, i.e., a rate of an opening of the cell 35 in the front end surface 33 (step S310). In this embodiment, the CPU 12 derives the opening rate OFA from a relation of the following equation (4) by employing the cell pitch P [m] and the wall thickness Wt [m] (see FIGS. 4 and 5), which are set in the object information 20 in correspondence to the front end mesh 40a as the derivation target.

$$OFA=(P-Wt)^2/P^2 \qquad \text{Eq. (4)}$$

(where P: cell pitch, and Wt: wall thickness)

Figure 14:
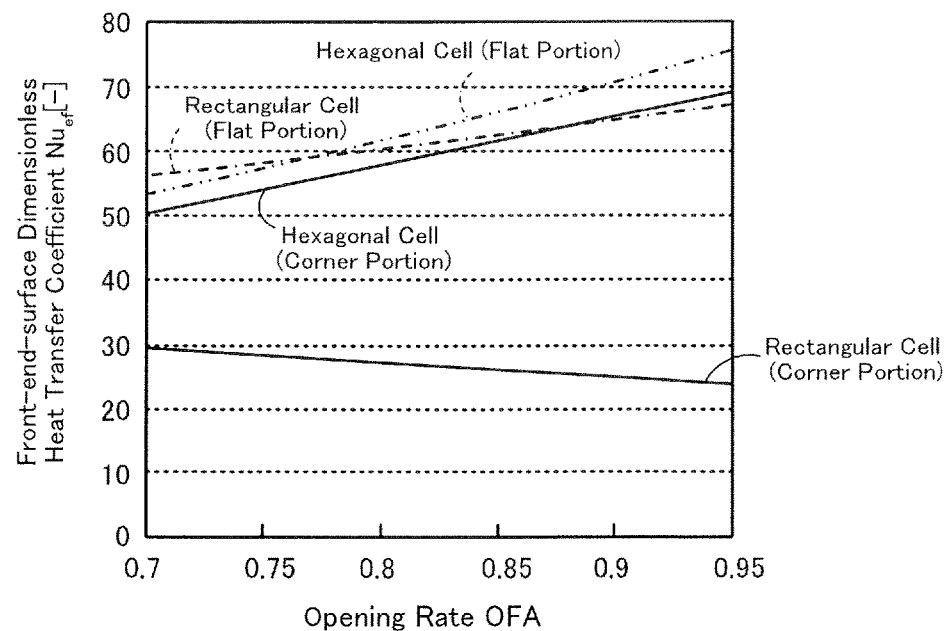
FIG. 14 is a conceptual view of the front-end-surface dimensionless correspondence information 24.

After deriving the opening rate OFA, the CPU 12 reads and obtains (refers to) the front-end-surface dimensionless correspondence information 24 stored in the HDD 15, and derives a front-end-surface dimensionless heat transfer coefficient $Nu_{ef}$ of the front end mesh 40a as the derivation target on the basis of a correspondence relation contained in the front-end-surface dimensionless correspondence information 24 (step S320). The front-end-surface dimensionless correspondence information 24 is described here. FIG. 14 is a conceptual view of the front-end-surface dimensionless correspondence information 24 stored in the HDD 15. The front-end-surface dimensionless correspondence information 24 is information regarding the correspondence relation between the opening rate OFA and the front-end-surface dimensionless heat transfer coefficient $Nu_{ef}$ that is a dimensionless value of the front-end-surface heat transfer coefficient $h_{ef}$. An upper column in FIG. 14 denotes the correspondence relation in the form of a graph (map), and a lower column denotes the correspondence relation by equations. As seen from FIG. 14, the front-end-surface dimensionless correspondence information 24 contains, as the correspondence relation between the opening rate OFA and the front-end-surface dimensionless heat transfer coefficient $Nu_{ef}$, information regarding the correspondence relation expressed by the following equation (9).

$$Nu_{ef}=Df \times \exp(Ef \times OFA) \qquad \text{Eq. (9)}$$

(where $Nu_{ef}$: front-end-surface dimensionless heat transfer coefficient, Df and Ef: coefficients, and OFA: opening rate)

The front-end-surface dimensionless correspondence information 24 further contains the correspondence relation that is different for each shape and each shape element of the inner wall surface 35a of the cell 35 in the front end mesh 40a as the derivation target. Thus, as indicated in the lower column in FIG. 14, the coefficients Df and Ef in the above equation (9) are set for each shape and each shape element of the inner wall surface 35a. More specifically, assuming that the coefficients Df and Ef in the case of the cell shape information being rectangular and the shape element being the flat portion are denoted by coefficients $Df_{11}$ and $Ef_{11}$, respectively, the coefficient $Df_{11}=34$ and the coefficient $Ef_{11}=0.7$ are set. Assuming that the coefficients Df and Ef in the case of the cell shape information being rectangular and the shape element being the corner portion are denoted by coefficients $Df_{12}$ and $Ef_{12}$, respectively, the coefficient $Df_{12}=52$ and the coefficient $Ef_{12}=-0.8$ are set. Assuming that the coefficients Df and Ef in the case of the cell shape information being hexagonal and the shape element being the flat portion are denoted by coefficients $Df_{21}$ and $Ef_{21}$, respectively, the coefficient $Df_{21}=20$ and the coefficient $Ef_{21}=1.4$ are set. Assuming that the coefficients Df and Ef in the case of the cell shape information being hexagonal and the shape element being the corner portion are denoted by coefficients $Df_{22}$ and $Ef_{22}$, respectively, the coefficient $Df_{22}=22$ and the coefficient $Ef_{22}=1.2$ are set. As seen from FIG. 14, when the cell shape is rectangular and the shape element is the corner portion, the front-end-surface dimensionless heat transfer coefficient $Nu_{ef}$ tends to decrease as the opening rate OFA increases. In the other cases, the front-end-surface dimensionless heat transfer coefficient $Nu_{ef}$ tends to increase as the opening rate OFA increases.

The correspondence relation between the opening rate OFA and the front-end-surface dimensionless heat transfer coefficient $Nu_{ef}$, illustrated in FIG. 14, can be obtained with experiments or simulations in which the opening rate OFA is changed to various values, similarly to the above-described correspondence relation set as the inner-wall-surface dimensionless correspondence information 23. Values of the coefficients Df and Ef are not limited to the above-mentioned values. For example, though not being particularly limited to the following, the coefficient $Df_{11}$ may be set to a value within the range of 30 to 40, and the coefficient $Ef_{11}$ may be set to a value within the range of 0.5 to 1.0. The coefficient $Df_{12}$ may be set to a value within the range of 50 to 55, and the coefficient $Ef_{12}$ may be set to a value within the range of $-1.0$ to $-0.5$. The coefficient $Df_{21}$ may be set to a value within the range of 18 to 22, and the coefficient $Ef_{21}$ may be set to a value within the range of 1.0 to 1.8. The coefficient $Df_{22}$ may be set to a value within the range of 20 to 24, and the coefficient $Ef_{22}$ may be set to a value within the range of 0.8 to 1.6. In addition, the front-end-surface dimensionless correspondence information 24 may be information representing the correspondence relation in the form of the graph (map) as denoted in the upper column in FIG. 14, or information representing the correspondence relation by the equations and the coefficients as denoted in the lower column in FIG. 14.

The processing executed in step S320 using the above front-end-surface dimensionless correspondence information 24 will be described below. In step S320, the CPU 12 first derives the front-end-surface dimensionless heat transfer coefficient corresponding to each of the shape elements by employing the correspondence relation in the front-end-surface dimensionless correspondence information 24, the relevant correspondence relation being specified on the basis of each cell shape and each shape element both contained in the shape information stored in correspondence to the front end mesh 40a as the derivation target. For example, the front-end-surface dimensionless heat transfer coefficient corresponding to the flat portion of the rectangular cell is derived as $D_{f11} \times \exp(Ef_{11} \times OFA)$ from the equation (9). The front-end-surface dimensionless heat transfer coefficient corresponding to the corner portion of the rectangular cell is derived as $Df_{12} \times \exp(Ef_{12} \times OFA)$ from the equation (9). Then, the CPU 12 weights the front-end-surface dimensionless heat transfer coefficient corresponding to each of the shape elements with the weight (i.e., the weight K1 for the flat portion or the weight K2 for the corner portion), which is set in the object information 20 in correspondence to the front end mesh 40a as the derivation target, and derives the weighted sum of the individual front-end-surface dimensionless heat transfer coefficients after the weighting as the front-end-surface dimensionless heat transfer coefficient $Nu_{ef}$ of the front end mesh 40a as the derivation target. Thus, in step S320, the front-end-surface dimensionless heat transfer coefficient $Nu_{ef}$ is derived from the following equation (10).

$$Nu_{ef} = K1 \times D_{f11} \times \exp(Ef_{11} \times OFA) + K2 \times Df_{12} \times \exp(Ef_{12} \times OFA) \qquad \text{Eq. (10)}$$

After step S320, the CPU 12 derives, on the basis of the front-end-surface dimensionless heat transfer coefficient $Nu_{ef}$ having been derived above, the front-end-surface heat transfer coefficient $h_{ef}$ between the open end surface of the front end mesh 40a as the derivation target and the fluid (step S330). In this embodiment, the CPU 12 derives the front-end-surface heat transfer coefficient $h_{ef}$ [W/(m²·K)] from a relation of the following equation (11) on the basis of the front-end-surface dimensionless heat transfer coefficient $Nu_{ef}$, the fluid thermal conductivity $\lambda_g$ [W/(m·K)] of the fluid contacting the open end surface of the front end mesh 40a as the derivation target, and the hydraulic diameter $d_h$ [m] set in the object information 20 in correspondence to the front end mesh 40a as the derivation target. It is to be noted that the equation (11) is similar to the equation (8) used in above step S250. However, the fluid thermal conductivity $\lambda_g$ in the equation (11) is not the fluid thermal conductivity $\lambda_g$ of the fluid in the cell mesh 42 of the front end mesh 40a, and it is given as the fluid thermal conductivity $\lambda_g$ of the fluid contacting the open end surface of the front end mesh 40a. In this embodiment, because the fluid flows into the honeycomb structure 30 from the front end surface, the fluid thermal conductivity $\lambda_g$ here is derived on the basis of the fluid temperature Tg (=temperature of the fluid immediately before flowing into the cell 35 of the honeycomb structure 30) at the current time t, which is contained in the fluid inflow conditions, and the conditions for the fluid physical property values, both the conditions being set in above step S110.

$$h_{ef} = (Nu_{ef} \times \lambda_g)/d_h \qquad \text{Eq. (11)}$$

After, as described above, executing steps S310 to S330 and deriving the front-end-surface heat transfer coefficient $h_{ef}$ corresponding to the front end mesh 40a as the derivation target, the CPU 12 determines whether there still remains the front end mesh 40a for which the front-end-surface heat transfer coefficient $h_{ef}$ is not yet derived (step S340). If there still remains the front end mesh 40a for which the front-end-surface heat transfer coefficient $h_{ef}$ is not yet derived, the CPU 12 executes the processing of step S300 to set the relevant front end mesh 40a as the derivation target, and executes the processing subsequent to step S310. If the CPU 12 determines in step S340 that there remains no front end mesh 40a for which the front-end-surface heat transfer coefficient $h_{ef}$ is not yet derived, the CPU 12 stores the respective front-end-surface heat transfer coefficients $h_{ef}$, which have been derived for the plural front end meshes 40a, in the HDD 15 in correspondence to the individual front end meshes 40a (step S350), and brings the front-end-surface heat transfer coefficient deriving process to an end.

Thus, in this embodiment, the front-end-surface dimensionless correspondence information 24 is previously stored in the HDD 15, and the front-end-surface dimensionless heat transfer coefficient $Nu_{ef}$ of each front end mesh 40a at an arbitrary time t is derived by employing the front-end-surface dimensionless correspondence information 24. The front-end-surface heat transfer coefficient $h_{ef}$ based on the front-end-surface dimensionless heat transfer coefficient $Nu_{ef}$ is then derived by employing the fluid thermal conductivity $\lambda_g$ of which value is variable depending on the time t. As a result, the front-end-surface heat transfer coefficient $h_{ef}$ (of which value is variable depending on the time t) reflecting the fluid state at the time t is derived appropriately.

Figure 15:
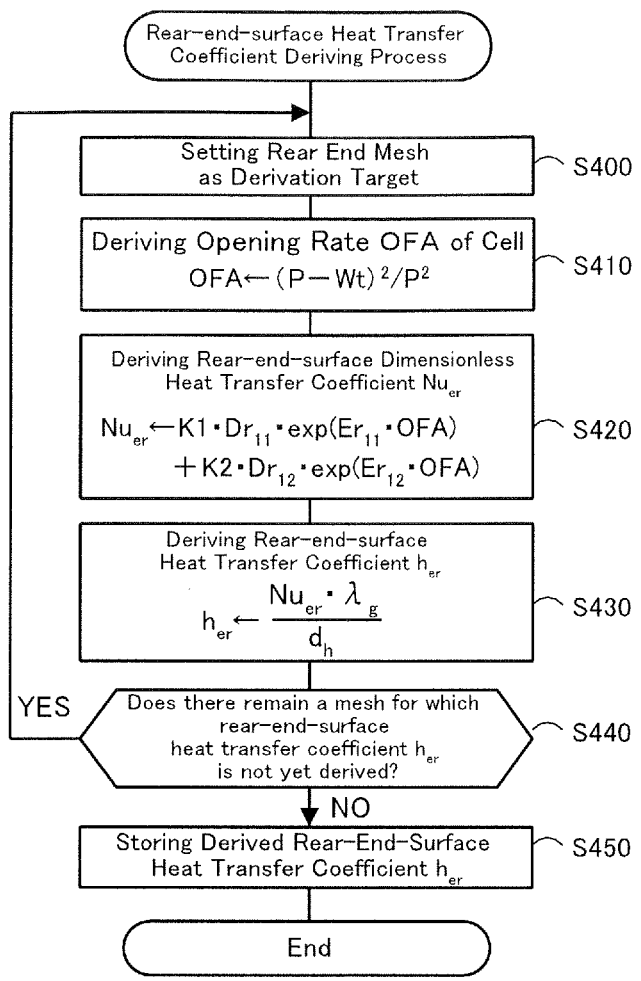
FIG. 15 is a flowchart illustrating one example of the rear-end-surface heat transfer coefficient deriving process.

After executing the front-end-surface heat transfer coefficient deriving process of step S140 in FIG. 10 as described above, the CPU 12 executes a rear-end-surface heat transfer coefficient deriving process for deriving a rear-end-surface heat transfer coefficient $h_{er}$ that is a heat transfer coefficient between the open end surface of the rear end mesh 40c and the fluid (i.e., a heat transfer coefficient between a portion of the rear end surface 34, the portion being involved in the rear end mesh 40c, and the fluid) (step S150). FIG. 15 is a flowchart illustrating one example of the rear-end-surface heat transfer coefficient deriving process. The rear-end-surface heat transfer coefficient deriving process is basically similar to the above front-end-surface heat transfer coefficient deriving process although the former is different from the latter in, for example, that the rear-end-surface dimensionless correspondence information 25 is used instead of the front-end-surface dimensionless correspondence information 24, and that the derivation target is the rear end mesh 40c instead of the front end mesh 40a.

Upon the start of the rear-end-surface heat transfer coefficient deriving process, the CPU 12 first sets, from among the plural rear end meshes 40c, one rear end mesh 40c as a target for derivation of the rear-end-surface heat transfer coefficient $h_{er}$ (step S400). It is to be noted that the rear end mesh 40c (particularly the wall mesh 41 thereof) corresponds to an end wall mesh in the present invention. Then, the CPU 12 derives, for the cell 35 represented by the rear end mesh 40c as the derivation target, an opening rate OFA, i.e., a rate of an opening of the cell 35 in the rear end surface 34 (step S410). The processing of step S410 is executed similarly to that of step S310 in the above front-end-surface heat transfer coefficient deriving process. Step S410 may be omitted in the case of employing the value derived in step S310 as it is.

Figure 16:
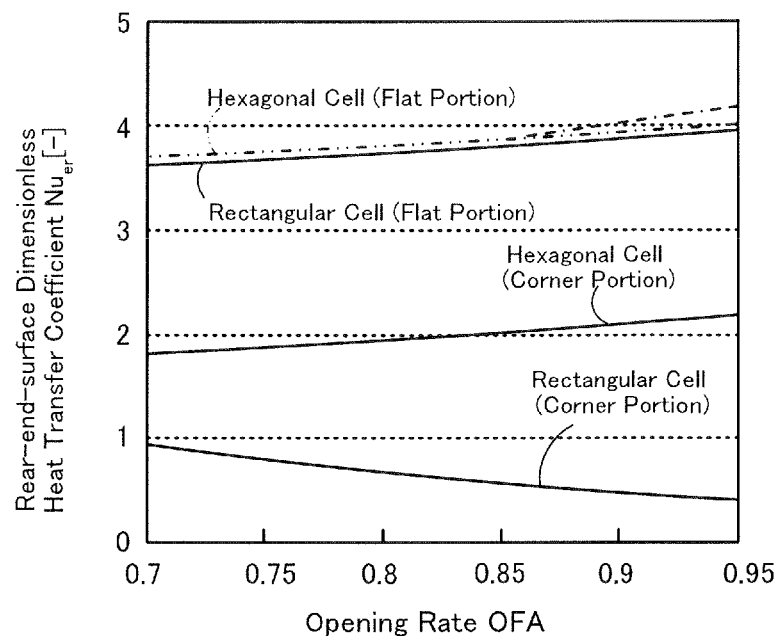
FIG. 16 is a conceptual view of the rear-end-surface dimensionless correspondence information 25.

After deriving the opening rate OFA, the CPU 12 reads and obtains (refers to) the rear-end-surface dimensionless correspondence information 25 stored in the HDD 15, and derives a rear-end-surface dimensionless heat transfer coefficient $Nu_s$ of the rear end mesh 40c as the derivation target on the basis of a correspondence relation contained in the rear-end-surface dimensionless correspondence information 25 (step S420). The rear-end-surface dimensionless correspondence information 25 is described here. FIG. 16 is a conceptual view of the rear-end-surface dimensionless correspondence information 25 stored in the HDD 15. The rear-end-surface dimensionless correspondence information 25 is information regarding the correspondence relation between the opening rate OFA and the rear-end-surface dimensionless heat transfer coefficient $Nu_{er}$ that is a dimensionless value of the rear-end-surface heat transfer coefficient $h_{er}$. An upper column in FIG. 16 denotes the correspondence relation in the form of a graph (map), and a lower column denotes the correspondence relation by equations. As seen from FIG. 16, the rear-end-surface dimensionless correspondence information 25 contains, as the correspondence relation between the opening rate OFA and the rear-end-surface dimensionless heat transfer coefficient $Nu_{er}$, information regarding the correspondence relation expressed by the following equation (12).

$$Nu_{er} = Dr \times \exp(Er \times OFA) \quad \text{Eq. (12)}$$

(where $Nu_s$: rear-end-surface dimensionless heat transfer coefficient, Dr and Er: coefficients, and OFA: opening rate)

The rear-end-surface dimensionless correspondence information 25 further contains the correspondence relation that is different for each shape and each shape element of the inner wall surface 35a of the cell 35 in the rear end mesh 40c as the derivation target. Thus, as indicated in the lower column in FIG. 16, the coefficients Dr and Er in the above equation (12) are set for each shape and each shape element of the inner wall surface 35a. More specifically, assuming that the coefficients Dr and Er in the case of the cell shape information being rectangular and the shape element being the flat portion are denoted by coefficients $Dr_{11}$ and $Er_{11}$, respectively, the coefficient $Dr_{11}=2.8$ and the coefficient $Er_{11}=0.3$ are set. Assuming that the coefficients Dr and Er in the case of the cell shape information being rectangular and the shape element being the corner portion are denoted by coefficients $Dr_{12}$ and $Er_{12}$, respectively, the coefficient $Dr_{12}=11$ and the coefficient $Er_{12}=-3.5$ are set. Assuming that the coefficients Dr and Er in the case of the cell shape information being hexagonal and the shape element being the flat portion are denoted by coefficients $Dr_{21}$ and $Er_{21}$, respectively, the coefficient $Dr_{21}=3.0$ and the coefficient $Er_{21}=0.3$ are set. Assuming that the coefficients Dr and Er in the case of the cell shape information being hexagonal and the shape element being the corner portion are denoted by coefficients $Dr_{22}$ and $Er_{22}$, respectively, the coefficient $Dr_{22}=1.1$ and the coefficient $Er_{22}=0.7$ are set. As seen from FIG. 16, when the cell shape is rectangular and the shape element is the corner portion, the rear-end-surface dimensionless heat transfer coefficient $Nu_s$ tends to decrease as the opening rate OFA increases. In other cases, the rear-end-surface dimensionless heat transfer coefficient $Nu_{er}$ tends to increase as the opening rate OFA increases.

The correspondence relation between the opening rate OFA and the rear-end-surface dimensionless heat transfer coefficient $Nu_{er}$, illustrated in FIG. 16, can be obtained with experiments or simulations in which the opening rate OFA is changed to various values, similarly to the above-described correspondence relation set as the front-end-surface dimensionless correspondence information 24. Values of the coefficients Dr and Er are not limited to the above-mentioned values. For example, though not being particularly limited to the following, the coefficient $Dr_{11}$ may be set to a value within the range of 2.4 to 3.2, and the coefficient $Er_{11}$ may be set to a value within the range of 0.2 to 0.4. The coefficient $Dr_{12}$ may be set to a value within the range of 10 to 12, and the coefficient $Er_{12}$ may be set to a value within the range of −4.0 to −3. The coefficient $Dr_{21}$ may be set to a value within the range of 2.6 to 3.4, and the coefficient $Er_{21}$ may be set to a value within the range of 0.1 to 0.5. The coefficient $Dr_{22}$ may be set to a value within the range of 0.8 to 1.4, and the coefficient $Er_{22}$ may be set to a value within the range of 0.5 to 1.0. In addition, the rear-end-surface dimensionless correspondence information 25 may be information representing the correspondence relation in the form of the graph (map) as denoted in the upper column in FIG. 16, or information representing the correspondence relation by the equations and the coefficients as denoted in the lower column in FIG. 16.

The processing executed in step S420 using the above rear-end-surface dimensionless correspondence information 25 will be described below. In step S420, the CPU 12 first derives the rear-end-surface dimensionless heat transfer coefficient corresponding to each of the shape elements by employing the correspondence relation in the rear-end-surface dimensionless correspondence information 25, the relevant correspondence relation being specified on the basis of each cell shape and each shape element both contained in the shape information stored in correspondence to the rear end mesh 40c as the derivation target. For example, the rear-end-surface dimensionless heat transfer coefficient corresponding to the flat portion of the rectangular cell is derived as $Dr_{11} \times \exp(Er_{11} \times OFA)$ from the equation (12). The rear-end-surface dimensionless heat transfer coefficient corresponding to the corner portion of the rectangular cell is derived as $Dr_{12} \times \exp(Er_{12} \times OFA)$ from the equation (12). Then, the CPU 12 weights the rear-end-surface dimensionless heat transfer coefficient corresponding to each of the shape elements with the weight (i.e., the weight K1 for the flat portion or the weight K2 for the corner portion), which is set in the object information 20 in correspondence to the rear end mesh 40c as the derivation target, and derives the weighted sum of the individual rear-end-surface dimensionless heat transfer coefficients after the weighting as the rear-end-surface dimensionless heat transfer coefficient $Nu_s$ of the rear end mesh 40c as the derivation target. Thus, in step S420, the rear-end-surface dimensionless heat transfer coefficient $Nu_{er}$ is derived from the following equation (13).

$$Nu_{er} = K1 \times Dr_{11} \times \exp(Er_{11} \times OFA) + K2 \times Dr_{12} \times \exp(Er_{12} \times OFA) \quad \text{Eq. (13)}$$

After step S420, the CPU 12 derives, on the basis of the rear-end-surface dimensionless heat transfer coefficient $Nu_{er}$ having been derived above, the rear-end-surface heat transfer coefficient $h_{er}$ between the open end surface of the rear end mesh 40c as the derivation target and the fluid (step S430). In this embodiment, the CPU 12 derives the rear-end-surface heat transfer coefficient $h_{er}$ [W/(m²·K)] from a relation of the following equation (14) on the basis of the rear-end-surface dimensionless heat transfer coefficient $Nu_s$, the fluid thermal conductivity $\lambda_g$ [W/(m·K)] of the fluid contacting the open end surface of the rear end mesh 40c as the derivation target, and the hydraulic diameter $d_h$ [m] set in the object information 20 in correspondence to the rear end mesh 40c as the derivation target. It is to be noted that the equation (14) is similar to the equation (8) used in above step S250. However, the fluid thermal conductivity $\lambda_g$ in the equation (14) is not the fluid thermal conductivity $\lambda_g$ of the fluid in the cell mesh 42 of the rear end mesh 40c, and it is given as the fluid thermal conductivity $\lambda_g$ of the fluid contacting the open end surface of the rear end mesh 40c. In this embodiment, the fluid in the space mesh 44 adjacent to the rear end mesh 40c on the rear side contacts the open end surface of the rear end mesh 40c. Therefore, the CPU 12 uses the fluid thermal conductivity $\lambda_g$ that is derived on the basis of the fluid temperature Tg in correspondence to the relevant space mesh 44 at the current time t and the conditions for the fluid physical property values, which have been set in above step S110. In the case of the time t=0, a value of the fluid temperature Tg in the space mesh 44 is given by the value set in the above-described initial conditions. In the case except for the time t=0, a value of the fluid temperature Tg in the space mesh 44 is given by a value derived in a heat transfer analysis process of step S160 described later.

$$h_{er} = (Nu_{er} \times \lambda_g)/d_h \qquad \text{Eq. (14)}$$

After, as described above, executing steps S410 to S430 and deriving the rear-end-surface heat transfer coefficient $h_{er}$ corresponding to the rear end mesh 40c as the derivation target, the CPU 12 determines whether there still remains the rear end mesh 40c for which the rear-end-surface heat transfer coefficient $h_{er}$ is not yet derived (step S440). If there still remains the rear end mesh 40c for which the rear-end-surface heat transfer coefficient $h_{er}$ is not yet derived, the CPU 12 executes the processing of step S400 to set the relevant rear end mesh 40c as the derivation target, and executes the processing subsequent to step S410. If the CPU 12 determines in step S440 that there remains no rear end mesh 40c for which the rear-end-surface heat transfer coefficient $h_{er}$ is not yet derived, the CPU 12 stores the respective rear-end-surface heat transfer coefficients $h_{er}$, which have been derived for the plural rear end meshes 40c, in the HDD 15 in correspondence to the individual rear end meshes 40c (step S450), and brings the rear-end-surface heat transfer coefficient deriving process to an end.

Thus, in this embodiment, the rear-end-surface dimensionless correspondence information 25 is previously stored in the HDD 15, and the rear-end-surface dimensionless heat transfer coefficient $Nu_s$ of each rear end mesh 40c at an arbitrary time t is derived by employing the rear-end-surface dimensionless correspondence information 25. The rear-end-surface heat transfer coefficient $h_{er}$ based on the rear-end-surface dimensionless heat transfer coefficient $Nu_{er}$ is then derived by employing the fluid thermal conductivity $\lambda_g$ of which value is variable depending on the time t. As a result, the rear-end-surface heat transfer coefficient $h_{er}$ (of which value is variable depending on the time t) reflecting the fluid state at the time t is derived appropriately.

After executing the processing (heat transfer coefficient deriving process) of steps S130 to S150 in FIG. 10 as described above, the CPU 12 executes a heat transfer analysis process for the plural honeycomb meshes 40 in accordance with the finite volume method (step S160). In the heat transfer analysis process, the wall meshes 41, the cell meshes 42, and the space meshes 44 are each regarded as a small element (also called a control volume) in the finite volume method. Heat transmission equations for individual small elements are derived by employing a state of each small element at the time t, and a solution to the equations, which is held for all the small elements, is determined. As a result, the CPU 12 derives, as values regarding the state of each small element after the lapse of a short time $\Delta t$ from the time t, the wall temperature Tr of each wall mesh 41 and the fluid temperature Tg of the fluid in each of the cell meshes 42 and the space meshes 44. Moreover, the CPU 12 stores the derived values in the HDD 15 in correspondence to the relevant time (time $t+\Delta t$) and each mesh.

On the basis of heat conduction and heat transfer between the small elements, the set boundary conditions, etc., the heat transmission equation is determined as a relational equation for which the energy conservation law is held, by employing the object information 20, the analysis conditions set in step S110, and so on. Specific examples of heat conduction are, e.g., heat conduction between a certain wall mesh 41 and the wall meshes 41 adjacent to the former in the XYZ-directions, and heat conduction through the fluid between a certain cell mesh 42 and the cell meshes 42 adjacent to the former in the front-rear direction (i.e., the gas flowing direction in the cell 35). In the case of taking into account those heat conductions, the above-described wall thermal conductivity $\lambda_r$ ($\lambda_{r1}$, $\lambda_{r2}$) the above-described fluid thermal conductivity $\lambda_g$, etc. are used. Specific examples of heat transfer are, e.g., heat transfer between the wall mesh 41 and the cell mesh 42 in the same honeycomb mesh 40, heat transfer between the front end mesh 40a and the fluid contacting the front end mesh 40a in the front end surface 33, and heat transfer between the rear end mesh 40c and the fluid contacting the rear end mesh 40c in the rear end surface 34. In the case of taking into account those heat transfers, the inner-wall-surface heat transfer coefficient $h_s$, the front-end-surface heat transfer coefficient $h_{ef}$, and the rear-end-surface heat transfer coefficient $h_{er}$ at the time t, which have been derived in the above-described heat transfer coefficient deriving process of steps S130 to S150, are used. More specifically, the CPU 12 derives a heat transfer amount $Q_s$ [W] between the wall mesh 41 and the cell mesh 42 in the same honeycomb mesh 40 from a relation of the following equation (15). Furthermore, the CPU 12 derives a heat transfer amount $Q_{ef}$[W] between the front end mesh 40a and the fluid contacting the front end mesh 40a in the front end surface 33 (i.e., the fluid incoming from the outside under the inflow conditions) from a relation of the following equation (16). Moreover, the CPU 12 derives a heat transfer amount $Q_{er}$ [W] between the rear end mesh 40c and the fluid (in the space mesh 44) contacting the rear end mesh 40c in the rear end surface 34 from a relation of the following equation (17). Then, the CPU 12 puts those heat transfer amounts $Q_s$, $Q_{ef}$ and $Q_{er}$ into the heat transmission equation. The CPU 12 derives the heat transfer amount $Q_s$ for each of the plural honeycomb meshes 40, the heat transfer amount $Q_{ef}$ for each of the plural front end meshes 40a, and the heat transfer amount $Q_{er}$ for each of the plural rear end meshes 40c. Respective values of the inner-wall-surface heat transfer coefficient $h_s$, the front-end-surface heat transfer coefficient $h_{ef}$, the rear-end-surface heat transfer coefficient $h_{er}$, the wall temperature Tr, and the fluid temperature Tg in the equations (15) to (17) are given by the values in the corresponding meshes as targets for derivation of the heat transfer amounts at the time t. The heat transmission areas $A_s$ and $A_e$ [m$^2$] in the equations (15) to (17) are given by the values set in the object information 20 in correspondence to the individual meshes as targets for derivation of the heat transfer amounts.

$$Q_s = h_s \times (Tr-Tg) \times \text{heat transmission area } A_s \qquad \text{Eq. (15)}$$

$$Q_{ef} = h_{ef} \times (Tr-Tg) \times \text{heat transmission area } A_e \qquad \text{Eq. (16)}$$

$$Q_{er} = h_{er} \times (Tr-Tg) \times \text{heat transmission area } A_e \qquad \text{Eq. (17)}$$

After executing heat transfer analysis process in step S160, the CPU 12 increments the time t by the short time $\Delta t$ (step S170), and determines whether the time t is the analysis end time $t_{end}$ (step S180). If the time t is not the analysis end time $t_{end}$, the CPU 12 executes the processing subsequent to step S130. Thus, the CPU 12 sets the wall temperature Tr and the fluid temperature Tg, which have been newly derived in the heat transfer analysis process of just preceding step S160, as the values at the current time t, and executes the heat transfer coefficient deriving process of steps S130 to S150 on the basis of those set values, thereby deriving the individual heat transfer coefficients. The CPU 12 then derives the wall temperature Tr and the fluid temperature Tg in step S160 after the lapse of another short time Δt. If the CPU 12 determines in step S180 that the time t is the analysis end time $t_{end}$, i.e., if the wall temperature Tr and the fluid temperature Tg at the $t_{end}$ analysis end time t have been derived in the heat transfer analysis process, the CPU 12 brings the temperature distribution deriving process to an end and executes the next processing. By executing the above-described temperature distribution deriving process of steps S120 to S180, the CPU 12 derives the values of the wall temperature Tr and the fluid temperature Tg for each mesh at each time from the time t=Δt to the time t=$t_{end}$, and stores the derived values in the HDD 15. Alternatively, the wall temperature Tr and the fluid temperature Tg for each mesh at the time t=0, which are given as the initial conditions, may be added, and the values of the wall temperature Tr and the fluid temperature Tg for each mesh at each time from the time t=0 to the time t=$t_{end}$ may be stored in the HDD 15.

After the temperature distribution deriving process, the CPU 12 executes, on the basis of the wall temperature Tr for each of the wall meshes 41 (i.e., the temperature distribution), which has been derived in the temperature distribution deriving process, a stress analysis process for analyzing a distribution of stress generated within the honeycomb structure 30 due to the temperature distribution (step S190). The stress analysis process can be executed in accordance with the known method, e.g., the finite element method or the finite volume method, by employing a model that represents the honeycomb structure 30 in the form of divided small elements. Manners of analyzing a distribution of stress generated due to a temperature distribution by the finite element method are disclosed in, e.g., Japanese Unexamined Patent Application Publication No. 2005-241448 and No. 2005-242679. The small elements used in step S190 may be the same as or different from the small elements (honeycomb meshes 40) used in the heat transfer analysis process of step S160. In the case of using the different small elements, the temperature of each of the small elements used in the stress analysis may be determined on the basis of the wall temperature Tr of each wall mesh 41 in consideration of differences in position and size between the wall mesh 41 and the small element used in the stress analysis. The CPU 12 derives, for example, a stress value for each of the small elements (i.e., a stress distribution) at each time as the result of the stress analysis process, and stores the derived stress distribution in the HDD 15.

After the stress analysis process, the CPU 12 executes an analysis result outputting process for outputting, as analysis result data, the results of the above temperature distribution deriving process and the above stress analysis process (step S195), thus completing this routine. The analysis result data contains, for example, the values of the wall temperature Tr and the fluid temperature Tg of each mesh at each time from the time t=0 to the time t=$t_{end}$, and the stress value in each small element at each time. The analysis result data may be output by storing the data in, e.g., the HDD 15 or an external storage, or by outputting the analysis result on the display 16 in accordance with an instruction from the user through the input device 17. Thermal shock resistance when the honeycomb structure 30 is exposed to a high-temperature fluid, for example, can be evaluated by employing the analysis result data.

Figure 17:
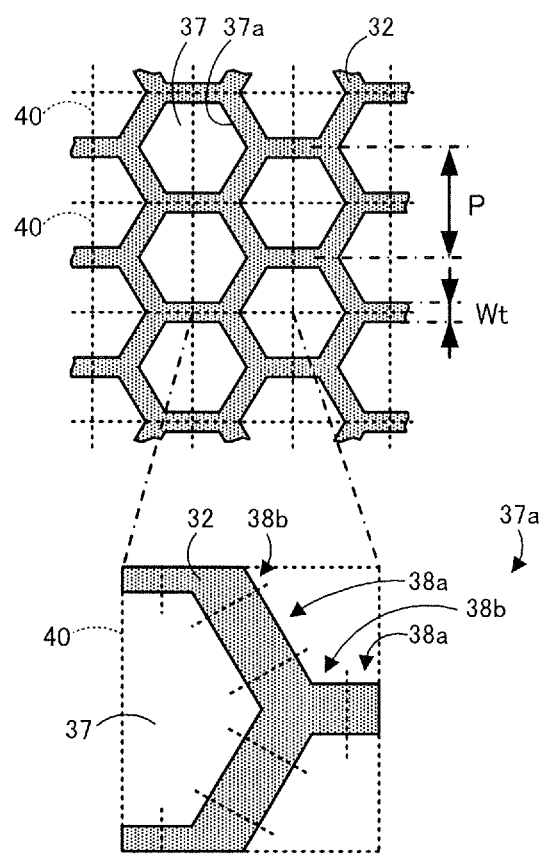
FIG. 17 is an explanatory view illustrating one example of the case where a honeycomb structure having hexagonal cells 37 simulated with the plural honeycomb meshes 40.

While the above description has been made in connection with the case where the analysis device 10 executes the analysis process on the object information 20 simulating the honeycomb structure 30 in which the cell 35 has the rectangular shape, the analysis device 10 can also similarly execute the analysis process on a honeycomb structure in which the cell has a hexagonal shape. In such a case, it is just required to use correspondence relations in the dimensionless correspondence information 22, which correspond to the hexagonal cell shape, in the heat transfer coefficient deriving process of steps S130 to S150. FIG. 17 is an explanatory view illustrating one example of the case where a honeycomb structure having hexagonal cells 37 simulated with the plural honeycomb meshes 40. A flat portion 38a and a corner portion 38b of an inner wall surface 37a of the cell 37 are also illustrated in FIG. 17.

Correspondence relations between components in this embodiment and components in the present invention are clarified here. The analysis device 10 in this embodiment corresponds to a honeycomb structure analysis device in the present invention. The CPU 12 corresponds to an object information obtaining module, an inner-wall-surface dimensionless correspondence information obtaining module, an inner-wall-surface heat transfer coefficient deriving module, a heat transfer analysis module, and temperature distribution deriving module. It is to be noted that, by explaining the operation of the analysis device 10, this embodiment is intended to further explain one example of an analysis method for the honeycomb structure and a program executing the analysis method according to the present invention.

According to the analysis device 10 of this embodiment described above in detail, while executing the process of obtaining the object information 20 and the process of obtaining the inner-wall-surface dimensionless correspondence information 23 from the HDD 15, the CPU 12 derives the inner-wall-surface heat transfer coefficient $h_s$, i.e., the heat transfer coefficient between the inner wall surface 35a of the cell 35 and the fluid, at an arbitrary time t from the analysis start time until the lapse of a predetermined time as follows. First, the CPU 12 sets the honeycomb mesh 40 (i.e., the wall mesh 41 and the cell mesh 42) as the target for derivation of the inner-wall-surface heat transfer coefficient $h_s$, and derives the dimensionless coordinate X* on the basis of the position information (X-coordinate) of the set honeycomb mesh 40 and the fluid state information regarding the state of the fluid in the set cell mesh 42 at the time t. Then, the CPU 12 derives, on the basis of the inner-wall-surface dimensionless correspondence information 23, the inner-wall-surface dimensionless heat transfer coefficient $Nu_s$ corresponding to the derived dimensionless coordinate X*. Then, the CPU 12 derives, on the basis of the derived inner-wall-surface dimensionless heat transfer coefficient $Nu_s$, the inner-wall-surface heat transfer coefficient $h_s$ between the wall mesh 41 and the cell mesh 42 that have been set as the derivation target. Thereafter, the CPU 12 executes the above-mentioned processes on the plural wall meshes 41 and the plural cell meshes 42 while the derivation target is changed from one to another. Here, the relation between the dimensionless coordinate X* and the inner-wall-surface dimensionless heat transfer coefficient $Nu_s$ can be expressed by the same correspondence relation regardless of the fluid state. Therefore, by deriving the dimensionless coordinate X* on the basis of the fluid state information at the time t, it is possible to derive the inner-wall-surface dimensionless heat transfer coefficient $Nu_s$ by employing the same correspondence relation, and to appropriately derive the inner-wall-surface heat transfer coefficient $h_s$ reflecting the fluid state information in arbitrary one of the honeycomb meshes 40 at the time t. Thus, by executing the heat transfer analysis including the derivation of the heat transfer amounts $Q_s$ with the use of the inner-wall-surface heat transfer coefficients $h_s$ that have been derived for the plural honeycomb meshes 40, the wall temperatures Tr of the plural wall meshes 41 and the fluid temperatures Tg in the plural cell meshes 42 after the lapse of the short time Δt from the time t can be derived with higher accuracy than that when the heat transfer coefficient is approximated by a constant value. In other words, the heat transfer analysis process can be performed with higher accuracy. By repeatedly executing the inner-wall-surface heat transfer coefficient deriving process and the heat transfer analysis process, the heat transfer analysis can be accurately performed over a period from the analysis start time until the lapse of a predetermined time, and the respective wall temperatures Tr of the plural wall meshes 41 after the lapse of the predetermined time can be accurately derived. As a result, a state of the honeycomb structure 30 when it is exposed to the fluid can be analyzed with higher accuracy.

In the object information 20, one or more of the plural wall meshes 41 each represent a region of the honeycomb structure 30, the region involving at least a part of the walls 32 and at least a part of the cells 35 together, in a homogenized state. Accordingly, the number of meshes can be reduced in comparison with the case of representing the entire structural configuration (shape) of the walls with the plural wall meshes 41, by way of example, as illustrated in FIG. 8. Hence a time (computing time) needed to execute the processing in, e.g., the inner-wall-surface heat transfer coefficient deriving process and the heat transfer analysis process, can be shortened. Because of the computing time being substantially proportional to the number of meshes, when the number of meshes is reduced to 1/1000, for example, the computing time is also reduced to about 1/1000. The number of meshes can be appropriately set in consideration of the required analysis accuracy and the computing time. Furthermore, because the state of the honeycomb structure 30 can be accurately analyzed by employing the dimensionless correspondence information 22, the analysis can be performed with sufficient accuracy even when the computing time is reduced by setting the size of one honeycomb mesh 40 to be as large as including a region of one cell 35 like this embodiment.

Moreover, the object information 20 contains the shape information regarding the shape of the inner wall surface 35a of the cell 35 (i.e., the cell shape) in correspondence to at least one of the wall mesh 41 and the cell mesh 42, and the inner-wall-surface dimensionless correspondence information 23 contains the correspondence relation that is different for each cell shape of the inner wall surface 35a. In the inner-wall-surface heat transfer coefficient deriving process, the CPU 12 derives the inner-wall-surface dimensionless heat transfer coefficient $Nu_s$ based on the dimensionless coordinate X* by employing the correspondence relation between the dimensionless coordinate X* and the inner-wall-surface dimensionless heat transfer coefficient $Nu_s$, the relevant correspondence relation being specified on the basis of the shape information in correspondence to the honeycomb mesh 40 set as the derivation target. Accordingly, the inner-wall-surface heat transfer coefficient $h_s$ can be derived with higher accuracy in consideration of the shape of the inner wall surface 35a.

In addition, the object information 20 contains the shape information, i.e., information representing the shape of the inner wall surface 35a of the cell 35 as a combination of the plural shape elements, in correspondence to at least one of the wall mesh 41 and the cell mesh 42, and the inner-wall-surface dimensionless correspondence information 23 contains the correspondence relation that is different for each shape element. In the inner-wall-surface heat transfer coefficient deriving process, the CPU 12 derives the inner-wall-surface dimensionless heat transfer coefficient $Nu_s$ corresponding to each of the shape elements by employing the correspondence relation between the dimensionless coordinate X* and the inner-wall-surface dimensionless heat transfer coefficient $Nu_s$, the relevant correspondence relation being specified on the basis of each shape element contained in the shape information in correspondence to the honeycomb mesh 40 set as the derivation target. Thus, since the shape of the inner wall surface 35a is represented as the combination of the shape elements, the inner-wall-surface heat transfer coefficient $h_s$ can be derived with higher accuracy in consideration of the shape of the inner wall surface 35a. Furthermore, even when the shape of the inner wall surface 35a is complicated, the appropriate inner-wall-surface heat transfer coefficient $h_s$ can be derived by representing the inner wall surface 35a as a combination of simple shape elements.

The shape information is information representing the shape of the inner wall surface 35a in a combination of plural shape elements and respective weights K1 and K2 of the plural shape elements. When deriving the inner-wall-surface dimensionless heat transfer coefficient corresponding to each of the shape elements in the inner-wall-surface heat transfer coefficient deriving process, the CPU 12 derives the inner-wall-surface dimensionless heat transfer coefficients weighted with the weights corresponding to the individual shape elements, and derives the sum of those inner-wall-surface dimensionless heat transfer coefficients as the inner-wall-surface dimensionless heat transfer coefficient $Nu_s$. Accordingly, the shape of the inner wall surface 35a can be more appropriately represented by employing the weights K1 and K2 of the shape elements, and the inner-wall-surface heat transfer coefficient $h_s$ can be derived with higher accuracy.

The object information 20 is information simulating the honeycomb structure 30 in which the inner wall surface 35a of at least one of the plural cells 35 has a polygonal cross-sectional shape, and the shape information contains, as the plural shape elements, the flat portion 36a and the corner portion 36b of the inner wall surface 35a of the polygonal shape. Thus, since the inner wall surface 35a having the polygonal cross-sectional shape is represented by the shape elements including the corner portion and the flat portion, the inner-wall-surface heat transfer coefficient $h_s$ can be derived with higher accuracy in consideration of the shape of the inner wall surface 35a.

The inner-wall-surface dimensionless correspondence information 23 contains the information regarding the correspondence relation, expressed by the above equation (1), as the correspondence relation between the dimensionless coordinate X* and the inner-wall-surface dimensionless heat transfer coefficient $Nu_s$ in the fluid entrance region of the cell 35. In the inner-wall-surface heat transfer coefficient deriving process, when the derived dimensionless coordinate X* is positioned in the fluid entrance region, the CPU 12 derives the inner-wall-surface dimensionless heat transfer coefficient $Nu_s$ on the basis of the information regarding the correspondence relation of the equation (1). Thus, the inner-wall-surface heat transfer coefficient $h_s$ in the entrance region can be derived with higher accuracy by employing the correspondence relation of the equation (1).

The inner-wall-surface dimensionless correspondence information 23 further contains the information regarding the correspondence relation, expressed by the above equation (2), as the correspondence relation between the dimensionless coordinate X* and the inner-wall-surface dimensionless heat transfer coefficient $Nu_s$ in the fluid developed region of the cell 35. In the inner-wall-surface heat transfer coefficient deriving process, when the derived dimensionless coordinate X* is positioned in the fluid developed region, the CPU 12 derives the inner-wall-surface dimensionless heat transfer coefficient $Nu_s$ on the basis of the information regarding the correspondence relation of the equation (2). Thus, the inner-wall-surface heat transfer coefficient $h_s$ in the developed region can be derived with higher accuracy by employing the correspondence relation of the equation (2).

The CPU 12 still further executes, at an arbitrary time t from the analysis start time until the lapse of a predetermined time, an end-surface heat transfer coefficient deriving process (including the front-end-surface heat transfer coefficient deriving process and the rear-end-surface heat transfer coefficient deriving process) of executing a process of setting, from among a plurality of end wall meshes (i.e., the front end meshes 40a or the rear end meshes 40c) that are the wall meshes 41 representing the walls 32 involving the open end surfaces of the cells 35 in the honeycomb structure 30, one end wall mesh as a target for derivation of an end-surface heat transfer coefficient (i.e., the front-end-surface heat transfer coefficient $h_{ef}$ or the rear-end-surface heat transfer coefficient $h_{er}$), namely the heat transfer coefficient between the open end surface of the end wall mesh and the fluid, obtaining the end-surface dimensionless heat transfer coefficient (i.e., the front-end-surface dimensionless heat transfer coefficient $Nu_{ef}$ or the rear-end-surface dimensionless heat transfer coefficient $Nu_{er}$) that is a dimensionless value of an end-surface heat transfer coefficient in the set end wall mesh, and deriving the end-surface heat transfer coefficient in the set end wall mesh on the basis of the derived end-surface dimensionless heat transfer coefficient, and further executing the aforesaid process for the plural end wall meshes while the derivation target is changed from one to another. In the heat transfer analysis process, the CPU 12 executes, at an arbitrary time t from the analysis start time until the lapse of the predetermined time, the heat transfer analysis in consideration of the heat transfer amount $Q_{ef}$ or $Q_{er}$ between the end wall mesh and the fluid, the relevant heat transfer amount being derived on the basis of the derived end-surface heat transfer coefficient. In the temperature distribution deriving process, the CPU 12 repeatedly executes the inner-wall-surface heat transfer coefficient deriving process, the end-surface heat transfer coefficient deriving process, and the heat transfer analysis process, thereby deriving the wall temperature Tr for each of the plural wall meshes 41 after the lapse of the predetermined time. Thus, the end-surface heat transfer coefficient can be appropriately derived by employing the end-surface dimensionless heat transfer coefficient. Accordingly, the heat transfer analysis can be performed with higher accuracy in consideration of the derived end-surface heat transfer coefficient.

The object information 20 still further contains the information (i.e., the cell pitch P and the wall thickness Wt) regarding the opening rate OFA, namely the value representing the ratio of the opening of the cell 35 to the open end surface, in correspondence to each end wall mesh (including the front end mesh 40a and the rear end mesh 40c). In the end-surface heat transfer coefficient deriving process (including the front-end-surface heat transfer coefficient deriving process and the rear-end-surface heat transfer coefficient deriving process), the end-surface dimensionless heat transfer coefficient (i.e., the front-end-surface dimensionless heat transfer coefficient $Nu_{ef}$ or the rear-end-surface dimensionless heat transfer coefficient $Nu_{er}$) is derived on the basis of the opening rate OFA of the end wall mesh (i.e., the front end mesh 40a or the rear end mesh 40c) set as the derivation target. Accordingly, the end-surface dimensionless heat transfer coefficient can be derived with higher accuracy on the basis of the opening rate OFA, and hence the end-surface heat transfer coefficient (each of the front-end-surface heat transfer coefficient $h_{ef}$ and the rear-end-surface heat transfer coefficient $h_{er}$) can be derived with higher accuracy.

In the end-surface heat transfer coefficient deriving process, the CPU 12 derives the end-surface dimensionless heat transfer coefficient (i.e., the front-end-surface dimensionless heat transfer coefficient $Nu_{ef}$ or the rear-end-surface dimensionless heat transfer coefficient $Nu_{er}$) on the basis of the relation of the above equation (9) or (12). Thus, by employing the relation expressed by each of the equations (9) and (12), the end-surface heat transfer coefficient (each of the front-end-surface heat transfer coefficient $h_{ef}$ and the rear-end-surface heat transfer coefficient $h_{er}$) can be derived with higher accuracy.

On the basis of the wall temperature Tr of each wall mesh 41, which has been derived in the temperature distribution deriving process, the CPU 12 further executes the stress analysis process for analyzing a distribution of stress generated within the honeycomb structure 30. Thus, since the stress distribution is analyzed on the basis of the wall temperature Tr that has been accurately derived for each of the plural wall meshes 41, the stress analysis can be accurately performed.

Second Embodiment

Figure 18:
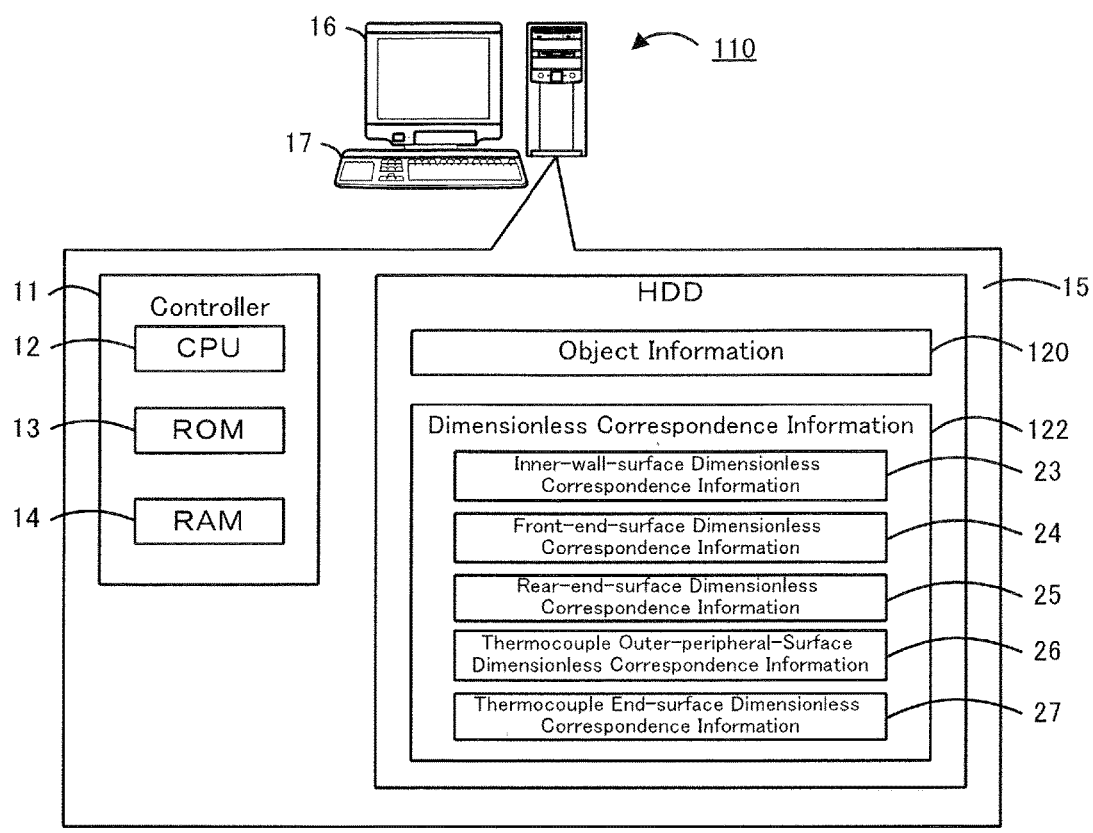
FIG. 18 is a block diagram schematically illustrating an analysis device 110 according to a second embodiment.

A second embodiment will be described below. FIG. 18 is a block diagram schematically illustrating an analysis device 110 according to a second embodiment. Among components in the second embodiment, the same components as those in the first embodiment are denoted by the same reference signs as those in the first embodiment, and descriptions of those components are omitted. The analysis device 110 according to the second embodiment analyzes a state where a thermocouple is inserted in the cell 35 of the honeycomb structure 30 in the first embodiment. The HDD 15 of the analysis device 110 stores object information 120 and dimensionless correspondence information 122 instead of the object information 20 and the dimensionless correspondence information 22 in the first embodiment. The object information 120 is information obtained by adding information regarding the thermocouple to the object information 20. The dimensionless correspondence information 122 contains thermocouple outer-peripheral-surface dimensionless correspondence information 26 and thermocouple end-surface dimensionless correspondence information 27 in addition to the inner-wall-surface dimensionless correspondence information 23, the front-end-surface dimensionless correspondence information 24, and the rear-end-surface dimensionless correspondence information 25.

Figure 20:
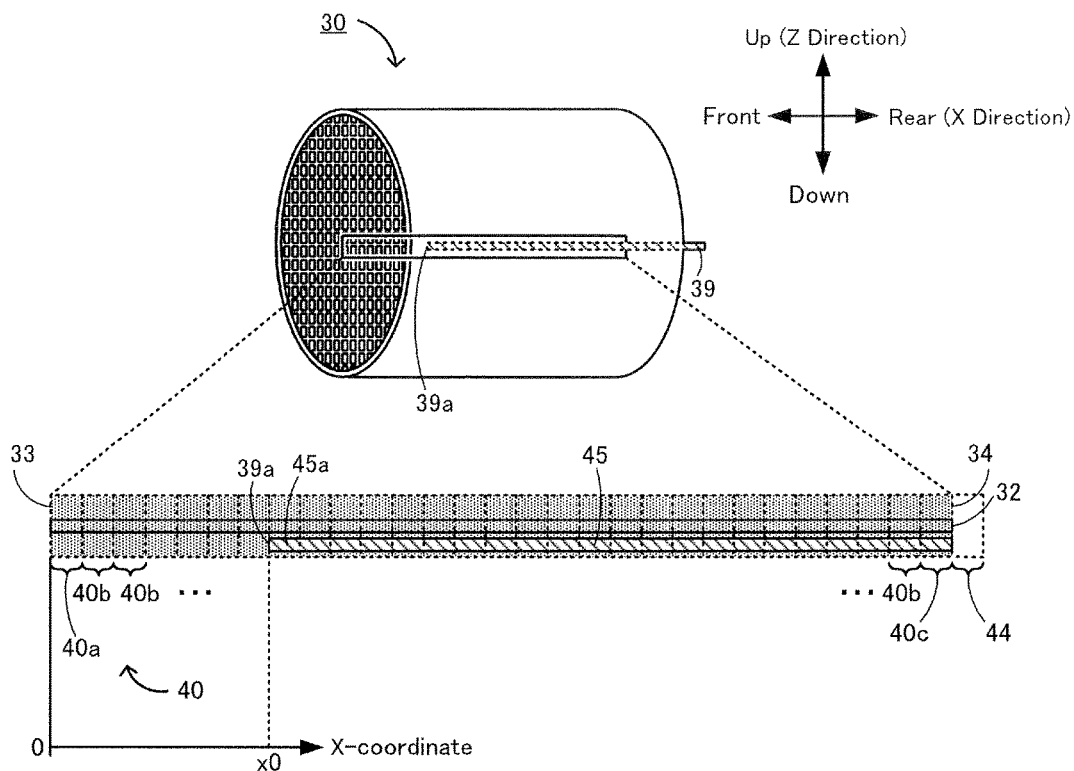
FIG. 20 is an explanatory view of the plural thermocouple meshes 45 arranged in the X-direction.
Figure 21:
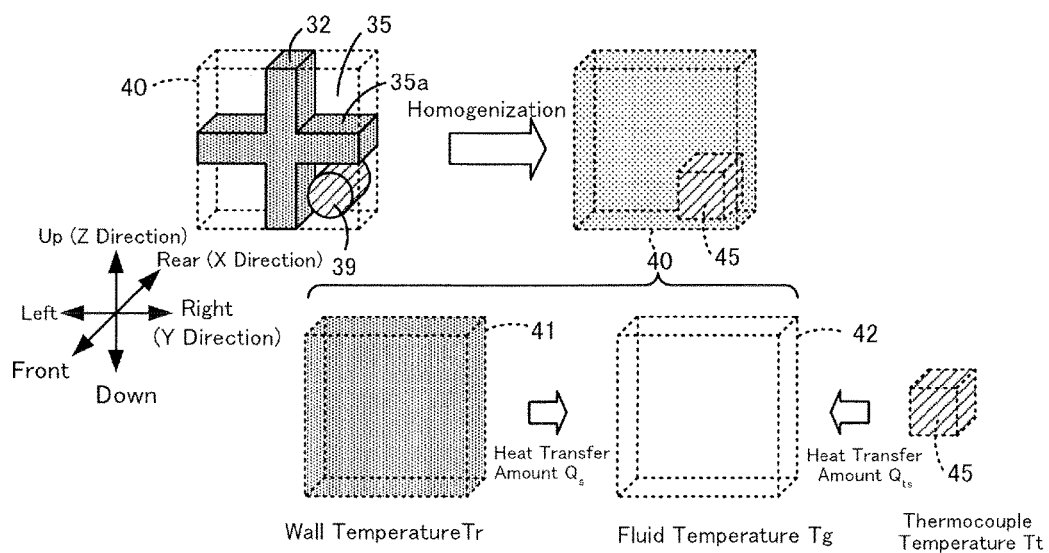
FIG. 21 is a conceptual view of the thermocouple mesh 45.

FIG. 19 is a conceptual view illustrating one example of part of the object information 120, the part regarding a thermocouple mesh 45. FIG. 20 is an explanatory view of the plural thermocouple meshes 45 arranged in the X-direction. FIG. 21 is a conceptual view of the thermocouple mesh 45. The object information 120 stored in the HDD 15 of the analysis device 110 is information simulating a state where a thermocouple 39 is inserted into the cell 35 of the honeycomb structure 30, illustrated in FIGS. 2 and 3, from the outer side of the rear end surface 34 (see an upper column in FIG. 20 and the left side in FIG. 21), with a plurality of meshes including the honeycomb meshes 40 (i.e., the wall meshes 41 and the cell meshes 42) and the thermocouple meshes 45 representing the thermocouple 39.

The object information 120 contains, in addition to the information regarding the plural honeycomb meshes 40 and indicated in FIG. 4, information regarding the thermocouple meshes 45 and indicated in FIG. 19. In the object information 120, as illustrated in FIG. 19, various items of the information regarding the thermocouple meshes 45 are set in correspondence to position information representing respective positions (XYZ-coordinates) of the thermocouple meshes 45. As illustrated in a lower column of FIG. 20, the plural thermocouple meshes 45 are arranged in the X-direction over a region from the X-coordinate x0 until the rear end surface 34, and they simulate the thermocouple 39 inserted into the cell 35.

The plural thermocouple meshes 45 arranged in the X-direction involve an end mesh 45a representing a region that includes an end surface 39a of the thermocouple 39. As illustrated in FIG. 19, which one of the thermocouple meshes 45 is the end mesh 45a is indicated, as position type information, in the object information 120.

The plural thermocouple meshes 45 do not simulate a detailed structural configuration of the thermocouple 39, and each thermocouple mesh 45 simulates a state that the thermocouple 39 is homogenized in a region involved by the thermocouple mesh 45 as illustrated on the right side in FIG. 21. Instead, the object information 120 contains structural information of the thermocouple 39 in correspondence to each of the plural thermocouple meshes 45. In this embodiment, as illustrated in FIG. 19, a diameter R [m] of the thermocouple 39 is set as the structural information in correspondence to each of the plural thermocouple meshes 45. Moreover, in an analysis process described later, a thermocouple temperature Tt [° C.] at each time is set as information for each of the plural thermocouple meshes 45 in correspondence.

In this embodiment, as illustrated on the right side in FIG. 21, one thermocouple mesh 45 is arranged to be involved within one honeycomb mesh 40 (cell mesh 42). Furthermore, a length of one thermocouple mesh 45 in the front-rear direction is the same as the length of the honeycomb mesh 40 in the front-rear direction. Accordingly, for heat transmission through heat transfer between an outer peripheral surface of the thermocouple 39 and the fluid in the cell 35, it is just required to consider a heat transfer amount $Q_{ts}$ [W] (see a lower right area in FIG. 21) between the thermocouple mesh 45 and the fluid in the cell mesh 42 involving the thermocouple mesh 45. For the end mesh 45a, as seen from a lower column in FIG. 20, heat transfer further occurs between the end mesh 45a and the fluid in the honeycomb mesh 40 (cell mesh 42) adjacent to the end mesh 45a on the front side. A heat transfer amount due to the heat transfer between a front end of the end mesh 45a and the fluid is called a heat transfer amount $Q_{te}$ [W].

The object information 120 further contains physical property values of the thermocouple 39 in correspondence to each of the plural thermocouple meshes 45. In this embodiment, as indicated in FIG. 19, a thermocouple density $\rho_t$ [kg/m$^3$], a thermocouple specific heat $Cp_t$ [J/(kg·K)], and a thermocouple thermal conductivity $\lambda_t$ [W/(m·K)], which are respectively a density, a specific heat, and a thermal conductivity of the thermocouple 39, are set in correspondence to each of the thermocouple meshes 45 as the physical property values of the thermocouple 39 in the region involved in the relevant thermocouple mesh 45. It is to be noted that, in this embodiment, the thermocouple mesh 45 represents the state that the thermocouple 39 is homogenized. Accordingly, among the physical property values of the thermocouple 39, the thermocouple density $\rho_t$ and the thermocouple thermal conductivity $\lambda_t$ are given as values obtained by modifying the actual physical property values of the thermocouple 39 corresponding to the homogenization. More specifically, the thermocouple density $\rho_t$=(actual density of the thermocouple 39)×(volume of a portion of the actual thermocouple 39, the portion being represented by one thermocouple mesh 45)/volume of one thermocouple mesh 45) is used. The thermocouple thermal conductivity $\lambda_t$ is given as the thermocouple thermal conductivity $\lambda_t$=(cross-sectional area of a portion of the actual thermocouple 39 in the YZ-plane, the portion being involved in one wall mesh 41)/(cross-sectional area of one thermocouple mesh 45 in the YZ-plane). In this embodiment, the thermocouple density $\rho_t$, the thermocouple specific heat $Cp_t$, and the thermocouple thermal conductivity $\lambda_t$ are set to their respective values that are the same for all the thermocouple meshes 45. Moreover, in this embodiment, since one thermocouple mesh 45 involves an entire cross-section of the thermocouple 39 in the YZ-plane as illustrated in FIG. 21, thermal conduction between the thermocouple meshes 45 occurs only in the X-direction. Therefore, the thermocouple thermal conductivity $\lambda_t$ is given as the thermal conductivity along the X-direction like the wall thermal conductivity $\lambda_{r2}$. In the case where one thermocouple mesh 45 involves only a part of the cross-section of the thermocouple 39 in the YZ-plane, i.e., in the case where the thermocouple meshes 45 are adjacent to each other in the Y-direction or the Z-direction, a thermocouple thermal conductivity in the YZ-direction may be additionally set in correspondence to each thermocouple mesh 45 like the wall thermal conductivity $\lambda_{r1}$.

The object information 120 further contains information regarding, for example, sizes (dimensions in the XYZ-directions) for each of the plural thermocouple meshes 45, and a value of the coordinate x0 that represents a position of the end surface 39a, i.e., a start point of the thermocouple mesh 45 in the X-direction. While FIG. 20 illustrates only one thermocouple 39, the object information 120 may be information simulating a state where plural thermocouples 39 are inserted into the honeycomb structure 30. In such a case, it is just required that the object information 120 contains information representing each of the plural thermocouples 39 by the plural thermocouple meshes 45. In this embodiment, the object information 120 simulates a state where nine thermocouples 39 are inserted in different cells 35, respectively.

The object information 120 contains the information regarding the plural honeycomb meshes 40 and indicated in FIG. 4. However, of the information regarding the plural honeycomb meshes 40, the information regarding the cell meshes 42 involving the thermocouple meshes 45 is modified to information different from that regarding the cell meshes 42 not involving the thermocouple meshes 45 so as to represent the state where the thermocouple 39 is present in the cell 35. More specifically, for each of the cell meshes 42 involving the thermocouple meshes 45, the hydraulic diameter $d_h$ is set to a different value from that for each of the cell meshes 42 not involving the thermocouple meshes 45. Here, the hydraulic diameter $d_h$ is expressed by $d_h$=4× (fluid passage area)/(wet edge length). In correspondence to the cell mesh 42 involving the thermocouple meshes 45, the object information 120 contains the hydraulic diameter $d_h$ derived from the above relational equation on an assumption that a value resulting from subtracting the cross-sectional area of the thermocouple 39 from the cross-sectional area of the cell 35 is given as the fluid passage area, and that a value resulting from adding the inner peripheral wet edge length of the cell 35 and an outer peripheral wet edge length of the thermocouple 39 is given as the wet edge length.

Figure 22:
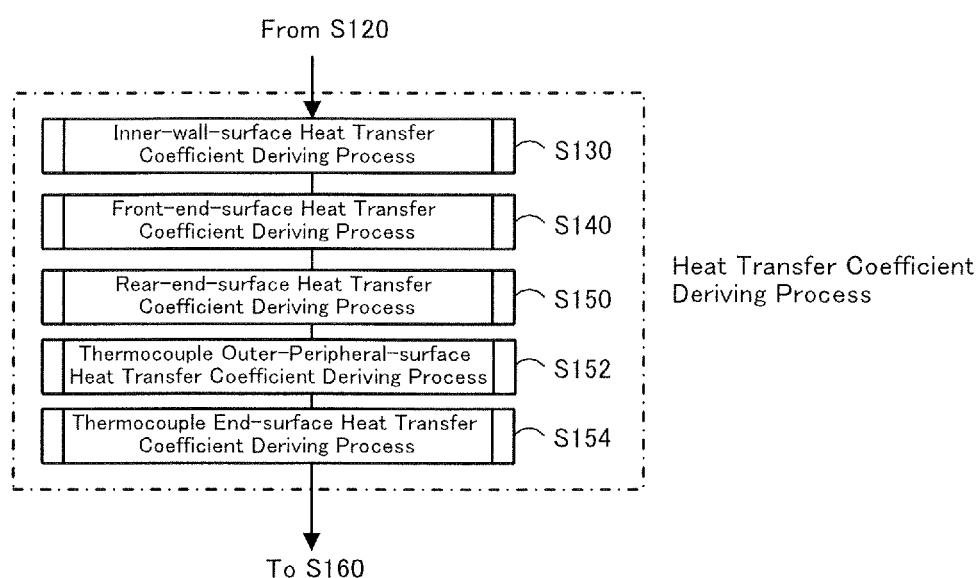
FIG. 22 is a flowchart illustrating one example of an analysis process routine.

An analysis process executed by the analysis device 110 will be described below. FIG. 22 is a flowchart illustrating one example of an analysis process routine. The analysis process in the second embodiment executes similar steps in the first embodiment except for executing, in a heat transfer coefficient deriving process, a thermocouple outer-peripheral-surface heat transfer coefficient deriving process of step S152 and a thermocouple end-surface heat transfer coefficient deriving process of step S154 in addition to the above-described steps S130 to S150. Accordingly, the steps other than the heat transfer coefficient deriving process are omitted in FIG. 22, and different points in the analysis process from the first embodiment are described in the following.

Figure 23:
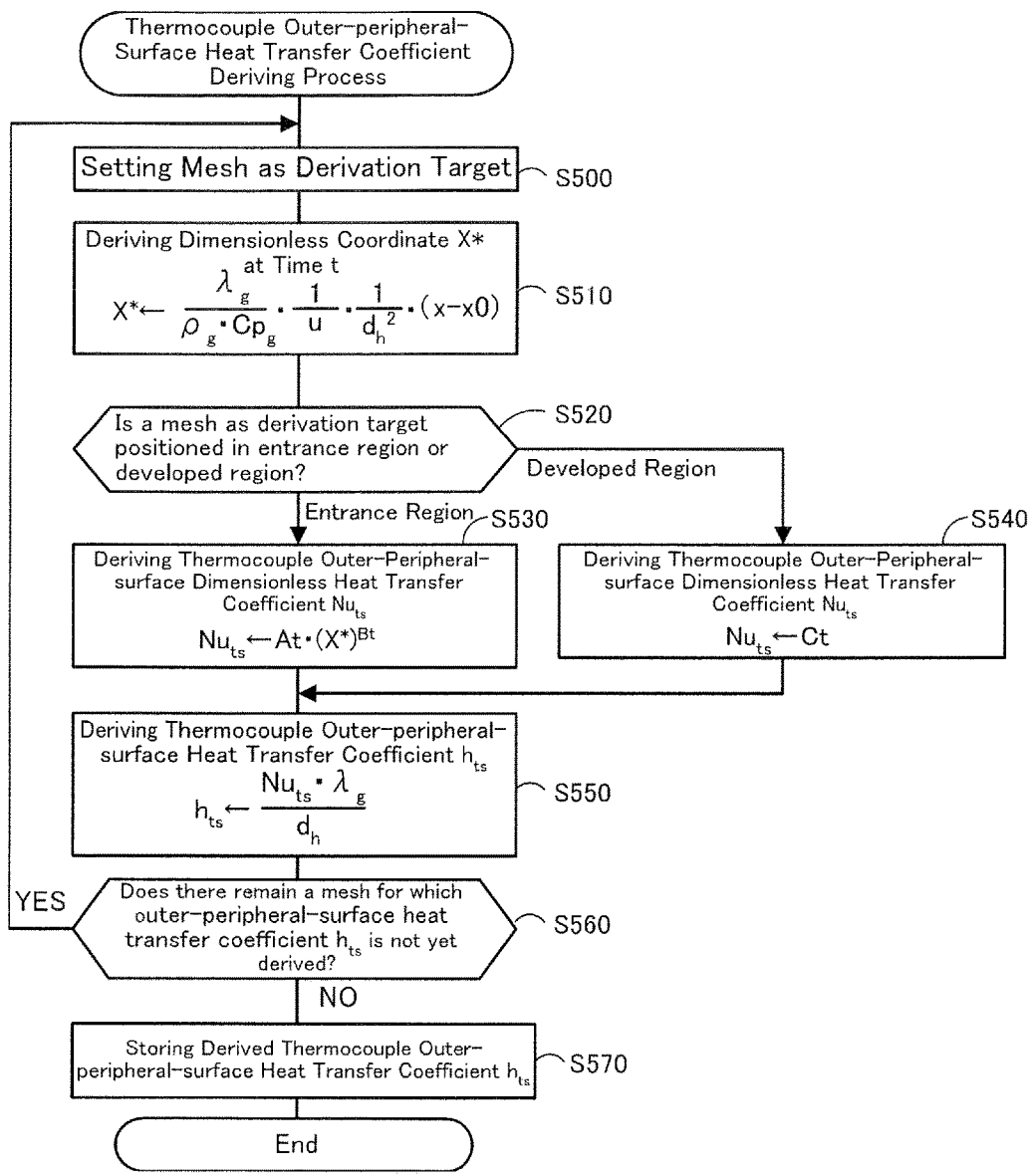
FIG. 23 is a flowchart illustrating one example of the thermocouple outer-peripheral-surface heat transfer coefficient deriving process.

After the rear-end-surface heat transfer coefficient deriving process of step S150, the CPU 12 executes the thermocouple outer-peripheral-surface heat transfer coefficient deriving process for deriving a thermocouple outer-peripheral-surface heat transfer coefficient $h_{ts}$ that is a heat transfer coefficient between the thermocouple mesh 45 and the fluid in the cell mesh 42 involving the thermocouple mesh 45, and that is a heat transfer coefficient between the thermocouple 39 and the fluid in the cell 35 through the outer peripheral surface of the thermocouple 39 (step S152). FIG. 23 is a flowchart illustrating one example of the thermocouple outer-peripheral-surface heat transfer coefficient deriving process. This process can be executed in a similar manner to the inner-wall-surface heat transfer coefficient deriving process illustrated in FIG. 11 except for using the thermocouple outer-peripheral-surface dimensionless correspondence information 26 instead of the inner-wall-surface dimensionless correspondence information 23.

Upon the start of the thermocouple outer-peripheral-surface heat transfer coefficient deriving process, the CPU 12 first sets, from among the plural meshes, the thermocouple mesh 45 and the cell mesh 42 as a derivation target for which the thermocouple outer-peripheral-surface heat transfer coefficient is to be derived (step S500). From among combinations of the thermocouple meshes 45 and the cell meshes 42 causing heat transfer therebetween through the outer peripheral surface of the thermocouple 39, the CPU 12 selects and sets one combination of both the meshes as the target for derivation of thermocouple outer-peripheral-surface heat transfer coefficient. In this embodiment, since the thermocouple mesh 45 is involved in the cell mesh 42 as described above, heat transfer through the outer peripheral surface of the thermocouple 39 generates only between the thermocouple mesh 45 and the cell mesh 42 involving the relevant thermocouple mesh 45. Accordingly, in this embodiment, one of the plural thermocouple meshes 45 and the cell mesh 42 involving the relevant thermocouple mesh 45 are as a target for derivation of the thermocouple outer-peripheral-surface heat transfer coefficient.

Then, on the basis of position information of the meshes (i.e., the thermocouple mesh 45 and the cell mesh 42) set as the derivation target in step S500 and fluid state information regarding the state of the fluid in the cell mesh 42 set as the derivation target at the time t, the CPU 12 derives a dimensionless coordinate X* (Graetz number) of the thermocouple mesh 45 as the derivation target at the time t (step S510). In this embodiment, the dimensionless coordinate X* is derived from a relation of the following equation (18). It is to be noted that the equation (18) represents the same relation as the above-described equation (5) except for using a value (x–x0), which is measured starting from the coordinate x0, as an X-coordinate value of the thermocouple mesh 45.

$$X^* = (\lambda_g/(\rho_g \times Cp_g)) \times (1/u) \times (1/d_h^2) \times (x-x0) \qquad \text{Eq. (18)}$$

After deriving the dimensionless coordinate X*, the CPU 12 executes processing of steps S520 to S540 and derives a thermocouple outer-peripheral-surface dimensionless heat transfer coefficient $Nu_{ts}$, i.e., a dimensionless value of the thermocouple outer-peripheral-surface heat transfer coefficient $h_{ts}$, in the mesh as the derivation target. The CPU 12 executes the processing of steps S520 to S540 while reading and obtaining (referring to) the thermocouple outer-peripheral-surface dimensionless correspondence information 26 stored in the HDD 15. A process of obtaining the thermocouple outer-peripheral-surface dimensionless correspondence information 26 in steps S520 to S540 corresponds to a thermocouple outer-peripheral-surface dimensionless correspondence information obtaining process in the present invention.

Figure 24:
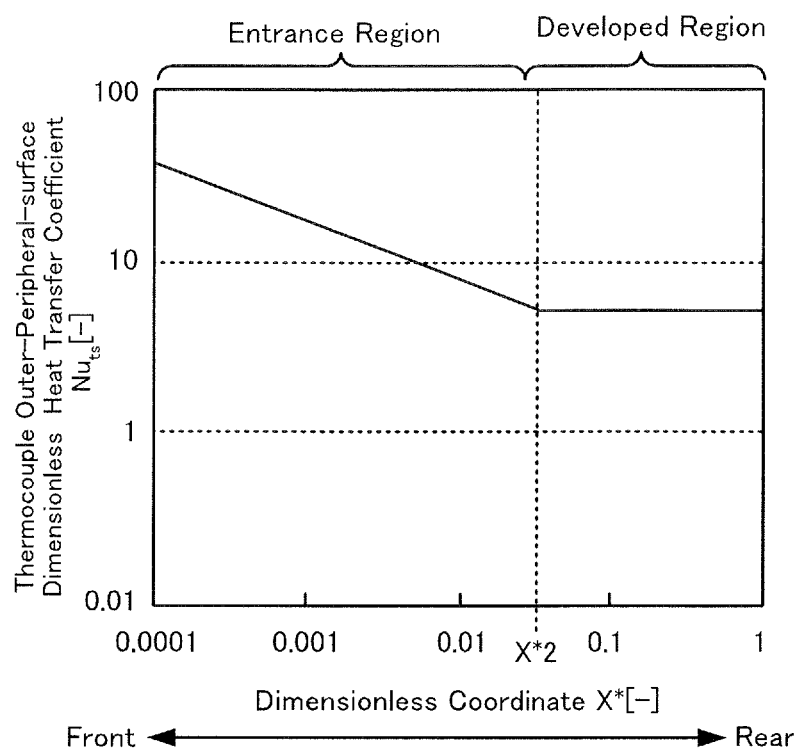
FIG. 24 is a conceptual view of the thermocouple outer-peripheral-surface dimensionless correspondence information 26.

The thermocouple outer-peripheral-surface dimensionless correspondence information 26 is described here. FIG. 24 is a conceptual view of the thermocouple outer-peripheral-surface dimensionless correspondence information 26 stored in the HDD 15. The thermocouple outer-peripheral-surface dimensionless correspondence information 26 is information regarding a correspondence relation between the dimensionless coordinate X* and the thermocouple outer-peripheral-surface dimensionless heat transfer coefficient $Nu_{ts}$. As illustrated in FIG. 24, the thermocouple outer-peripheral-surface dimensionless correspondence information 26 contains, as the correspondence relation between the dimensionless coordinate X* and the thermocouple outer-peripheral-surface dimensionless heat transfer coefficient $Nu_{ts}$ in the entrance region, information regarding the correspondence relation expressed by the following equation (19). The thermocouple outer-peripheral-surface dimensionless correspondence information 26 further contains, as the correspondence relation between the dimensionless coordinate X* and the thermocouple outer-peripheral-surface dimensionless heat transfer coefficient $Nu_{ts}$ in the developed region, information regarding the correspondence relation expressed by the following equation (20). It is to be noted that the equations (19) and (20) are relational equations similar to the above-described equations (1) and (2). As seen from FIG. 24, when the dimensionless coordinate X* is positioned in the entrance region, the thermocouple outer-peripheral-surface dimensionless heat transfer coefficient $Nu_{ts}$ tends to decrease as the dimensionless coordinate X* increases. When the dimensionless coordinate X* is positioned in the developed region, the thermocouple outer-peripheral-surface dimensionless heat transfer coefficient $Nu_{ts}$ corresponding to any value of the dimensionless coordinate X* is a constant value. Assuming the dimensionless coordinate X* at a boundary between the entrance region and the developed region to be a dimensionless coordinate X*2, the dimensionless coordinate X*2=0.35 is given in this embodiment.

$$Nu_{ts} = At \times (X^*)^{Bt} \qquad \text{Eq. (19)}$$

(where $Nu_{ts}$: thermocouple outer-peripheral-surface dimensionless heat transfer coefficient, $X^*$: dimensionless coordinate, and At, Bt: coefficients)

$$Nu_{ts} = Ct \qquad \text{Eq. (20)}$$

(where $Nu_{ts}$: thermocouple outer-peripheral-surface dimensionless heat transfer coefficient, and Ct: coefficient)

Because the coefficients At, Bt and Ct in the above equations (19) and (20) are values relating to the heat transfer between the outer peripheral surface of the thermocouple 39 and the fluid, they may be given as the same respective values regardless of the shape of the inner wall surface 35a of the cell 35. More specifically, the coefficient At=1.6, the coefficient Bt=−0.35, and the coefficient Ct=5.1 are given. The correspondence relation between the dimensionless coordinate $X^*$ and the thermocouple outer-peripheral-surface dimensionless heat transfer coefficient $Nu_{ts}$, illustrated in FIG. 24, can be obtained with experiments or simulations similarly to the correspondence relation contained in the above-described inner-wall-surface dimensionless correspondence information 23. Furthermore, values of the coefficients At, Bt and Ct are not limited to the above-mentioned values. For example, though not being particularly limited to the following, the coefficient At may be set to a value within the range of 1.0 to 2.0, the coefficient Bt may be set to a value within the range of −0.4 to −0.3, and the coefficient Ct may be set to a value within the range of 4.5 to 5.5. In addition, the thermocouple outer-peripheral-surface dimensionless correspondence information 26 may be information representing the correspondence relation in the form of the graph (map) as denoted in the upper column in FIG. 24, or information representing the correspondence relation by the equations and the coefficients as denoted in the lower column in FIG. 24.

After deriving the dimensionless coordinate $X^*$ in step S510, the CPU 12 determines, on the basis of the derived dimensionless coordinate $X^*$ and the thermocouple outer-peripheral-surface dimensionless correspondence information 26, whether the mesh as the derivation target is positioned in the entrance region or the developed region (step S520). Depending on the determination result, the CPU 12 derives the thermocouple outer-peripheral-surface dimensionless heat transfer coefficient $Nu_{ts}$ of the mesh as the derivation target by employing the correspondence relation expressed by the equation (19) or (20) (step S530 or S540). When the thermocouple outer-peripheral-surface dimensionless correspondence information 26 is given as information representing the correspondence relation in the form of the graph (map) as denoted in the upper column in FIG. 24, the determination of step S520 is no longer needed, and the thermocouple outer-peripheral-surface dimensionless heat transfer coefficient $Nu_{ts}$ corresponding to the mesh as the derivation target may be derived directly on the basis of both the dimensionless coordinate $X^*$, which has been derived in step S510, and the correspondence relation contained in the thermocouple outer-peripheral-surface dimensionless correspondence information 26.

After deriving the thermocouple outer-peripheral-surface dimensionless heat transfer coefficient $Nu_{ts}$ in step S530 or S540, the CPU 12 derives the thermocouple outer-peripheral-surface heat transfer coefficient $h_{ts}$ [W/(m²·K)] that is a heat transfer coefficient between the thermocouple mesh 45 and the cell mesh 42 on the basis of the derived thermocouple outer-peripheral-surface dimensionless heat transfer coefficient $Nu_{ts}$ (step S550). This process may be executed in a similar manner to that in above step S250 by employing the following equation (21) that is a similar to the above-described equation (8).

$$h_{ts} = (Nu_{ts} \times \lambda_g)/d_h \qquad \text{Eq. (21)}$$

After, as described above, executing steps S510 to S550 and deriving the thermocouple outer-peripheral-surface heat transfer coefficient $h_{ts}$ corresponding to the mesh as the derivation target, the CPU 12 determines whether there still remains the mesh (i.e., the combination of the thermocouple mesh 45 and the cell mesh 42) for which the thermocouple outer-peripheral-surface heat transfer coefficient $h_{ts}$ is not yet derived (step S560). If there still remains the mesh for which the thermocouple outer-peripheral-surface heat transfer coefficient $h_{ts}$ is not yet derived, the CPU 12 executes the processing of step S500 to set the relevant mesh as the derivation target, and executes the processing subsequent to step S510. If the CPU 12 determines in step S560 that there remains no mesh for which the thermocouple outer-peripheral-surface heat transfer coefficient $h_{ts}$ is not yet derived, the CPU 12 stores the respective thermocouple outer-peripheral-surface heat transfer coefficients $h_{ts}$, which have been derived for the plural meshes, in the HDD 15 in correspondence to the individual meshes (step S570), and brings the thermocouple outer-peripheral-surface heat transfer coefficient deriving process to an end.

Figure 25:
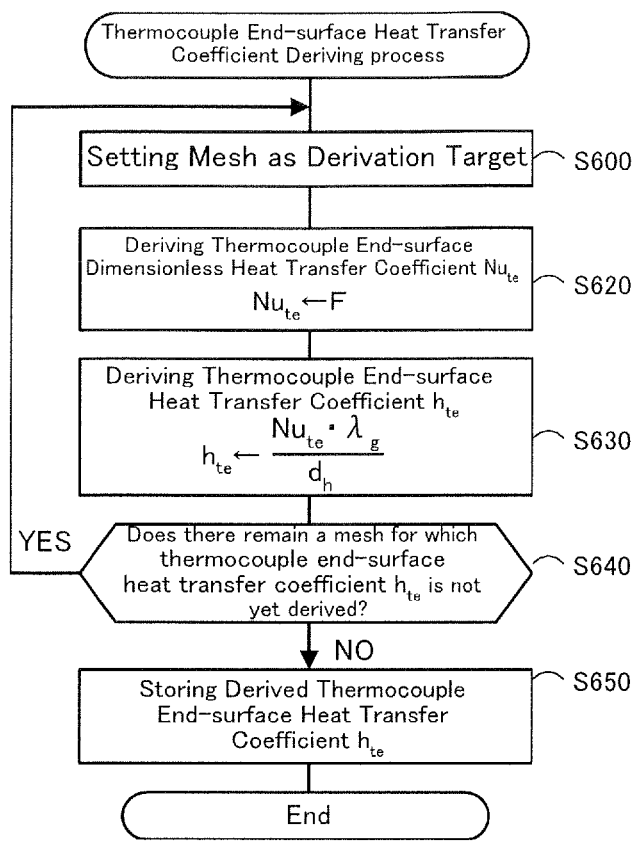
FIG. 25 is a flowchart illustrating one example of the thermocouple end-surface heat transfer coefficient deriving process.

After executing the thermocouple outer-peripheral-surface heat transfer coefficient deriving process of step S152 in FIG. 22 as described above, the CPU 12 executes a thermocouple end-surface heat transfer coefficient deriving process for deriving a thermocouple end-surface heat transfer coefficient $h_{te}$ that is a heat transfer coefficient between an end surface of the end mesh 45a among the thermocouple meshes 45 and the fluid (i.e., a heat transfer coefficient between the end surface 39a of the thermocouple 39 and the fluid) (step S154). FIG. 25 is a flowchart illustrating one example of the thermocouple end-surface heat transfer coefficient deriving process. This process can be executed in a similar manner to the front-end-surface heat transfer coefficient deriving process or the rear-end-surface heat transfer coefficient deriving process illustrated in FIG. 13 or 15 except for using the thermocouple end-surface dimensionless correspondence information 27 instead of the front-end-surface dimensionless correspondence information 24 or the rear-end-surface dimensionless correspondence information 25.

Upon the start of the thermocouple end-surface heat transfer coefficient deriving process, the CPU 12 first sets, from among the plural end meshes 45a (nine in this embodiment), one end mesh 45a as a target for derivation of the thermocouple end-surface heat transfer coefficient $h_{te}$ (step S600). Then, the CPU 12 reads and obtains (refers to) the thermocouple end-surface dimensionless correspondence information 27 stored in the HDD 15, and derives a thermocouple end-surface dimensionless heat transfer coefficient $Nu_{ts}$ of the end mesh 45a as the derivation target on the basis of a correspondence relation contained in the thermocouple end-surface dimensionless correspondence information 27 (step S620). In this embodiment, the thermocouple end-surface dimensionless heat transfer coefficient $Nu_{ts}$ is given from the correspondence relation expressed by the following equation (22). As with the correspondence relation between the dimensionless coordinate $X^*$ and the thermocouple outer-peripheral-surface dimensionless heat transfer coefficient $Nu_{ts}$, the thermocouple end-surface dimensionless heat transfer coefficient $Nu_{ts}$ is also a value not depending on the shape of the inner wall surface 35a of the cell 35. A coefficient F in the equation (22) is set to a value within the range of 36 to 40, for example. In this embodiment, the value of the coefficient F is set to 38.9. The value of the coefficient F can be obtained with experiments or simulations as with the correspondence relations in the front-end-surface dimensionless correspondence information 24 and the rear-end-surface dimensionless correspondence information 25 described above.

$$Nu_{te} = F \qquad \text{Eq. (22)}$$

(where $Nu_{te}$: thermocouple end-surface dimensionless heat transfer coefficient, and F: coefficient)

After step S620, the CPU 12 derives, on the basis of the thermocouple end-surface dimensionless heat transfer coefficient $Nu_t$, having been derived above, the thermocouple end-surface heat transfer coefficient $h_{te}$ between the open end surface of the end mesh 45a as the derivation target and the fluid (step S630). In this embodiment, the CPU 12 derives the thermocouple end-surface heat transfer coefficient $h_{te}$ [W/(m²·K)] from a relation of the following equation (23) on the basis of the thermocouple end-surface dimensionless heat transfer coefficient $Nu_{te}$, the fluid thermal conductivity $\lambda_g$ [W/(m·K)] of the fluid contacting the open end surface of the end mesh 45a as the derivation target, and the hydraulic diameter $d_h$ [m] of the cell 35 through which the fluid passes. It is to be noted that the equation (23) is similar to the equation (14) used in above step S430. The fluid thermal conductivity $\lambda_g$ is given as a value of the fluid thermal conductivity of the fluid contacting the end surface of the end mesh 45a as the derivation target, i.e., a value of the fluid thermal conductivity of the fluid in the cell mesh 42 adjacent to the end mesh 45a as the derivation target on the front side. Thus, the CPU 12 uses the fluid thermal conductivity $\lambda_g$ that is derived on the basis of both the fluid temperature Tg set in correspondence to the relevant cell mesh 42 at the current time t and the conditions for the fluid physical property values set in above step S110. Similarly, the hydraulic diameter $d_h$ is given as a value set in the object information 120 in correspondence to the cell mesh 42 that is adjacent to the end mesh 45a as the derivation target on the front side.

$$h_{te} = (Nu_{te} \times \lambda_g)/d_h \qquad \text{Eq. (23)}$$

After, as described above, executing steps S620 to S630 and deriving the thermocouple end-surface heat transfer coefficient $h_{te}$ corresponding to the end mesh 45a as the derivation target, the CPU 12 determines whether there still remains the end mesh 45a for which the thermocouple end-surface heat transfer coefficient $h_{te}$ is not yet derived (step S640). If there still remains the end mesh 45a for which the thermocouple end-surface heat transfer coefficient $h_{te}$ is not yet derived, the CPU 12 executes the processing of step S600 to set the relevant end mesh 45a as the derivation target, and executes the processing subsequent to step S620. If the CPU 12 determines in step S640 that there remains no end mesh 45a for which the thermocouple end-surface heat transfer coefficient $h_{te}$ is not yet derived, the CPU 12 stores the respective thermocouple end-surface heat transfer coefficients $h_{te}$, which have been derived for the plural end meshes 45a, in the HDD 15 in correspondence to the individual end meshes 45a (step S650), and brings the thermocouple end-surface heat transfer coefficient deriving process to an end.

After executing the processing of steps S152 to S154 in FIG. 22 as described above, the CPU 12 executes a heat transfer analysis process of step S160. In the heat transfer analysis process, the thermocouple meshes 45 are also each regarded as a small element in the finite volume method. The heat transfer analysis is executed in a similar manner to that in the first embodiment except for taking into account heat transmission in relation to the thermocouple meshes 45. As the thermal transmission in relation to the thermocouple meshes 45, there are, e.g., heat conduction between two thermocouple meshes 45 adjacent to each other in the X-direction, and heat transfer between the thermocouple mesh 45 and the fluid in the cell mesh 42. In the case of taking into account the heat conduction between the two adjacent thermocouple meshes 45, the above-described thermocouple thermal conductivity $\lambda_t$ is used. In the case of taking into account the heat transfer between the thermocouple mesh 45 and the cell mesh 42, the thermocouple outer-peripheral-surface heat transfer coefficient $h_{ts}$ and the thermocouple end-surface heat transfer coefficient $h_{te}$ at the time t, which have been derived in the above-described heat transfer coefficient deriving process of steps S152 to S154, are used. More specifically, the CPU 12 derives a heat transfer amount $Q_{ts}$ [W] between the thermocouple mesh 45 and the cell mesh 42 involving the thermocouple mesh 45 from a relation of the following equation (24). Furthermore, the CPU 12 derives a heat transfer amount $Q_{te}$ [W] between the end mesh 45a and the cell mesh 42 adjacent to the relevant end mesh 45a on the front side from a relation of the following equation (25). Then, the CPU 12 puts those heat transfer amounts $Q_{ts}$ and $Q_{te}$ into the heat transmission equation. The CPU 12 derives the heat transfer amount $Q_{ts}$ for each of the plural thermocouple meshes 45 and the heat transfer amount $Q_{te}$ for each of the plural end meshes 45a. Respective values of the thermocouple outer-peripheral-surface heat transfer coefficient $h_{ts}$, the thermocouple end-surface heat transfer coefficient $h_{te}$, the thermocouple temperature Tt, and the fluid temperature Tg in the equations (24) and (25) are given by the values in the corresponding meshes as targets for derivation of the heat transfer amounts at the time t (in the case of the time t=0, values set in the initial conditions are given). A heat transmission area $A_{ts}$ [m²] in the equation (24) is a surface area of the outer peripheral surface in a portion of the thermocouple 39, the portion being represented by the thermocouple mesh 45. The CPU 12 derives the heat transmission area $A_{ts}$ by employing the structural information (diameter R in this embodiment), the length of the thermocouple mesh 45 in the X-direction, etc., which are set in the object information 120 in correspondence to each thermocouple mesh 45 as a target for derivation of the heat transfer amount. A heat transmission area $A_{te}$ [m²] in the equation (25) is a surface area of the end surface 39a of the thermocouple 39. The CPU 12 derives the heat transmission area $A_{te}$ by employing the structural information (diameter R in this embodiment) that is set in the object information 120 in correspondence to each end mesh 45a as the target for derivation of the heat transfer amount.

$$Q_{ts} = h_{ts} \times (Tt - Tg) \times \text{heat transmission area } A_{ts} \qquad \text{Eq. (24)}$$

$$Q_{te} = h_{te} \times (Tt - Tg) \times \text{heat transmission area } A_{te} \qquad \text{Eq. (25)}$$

The heat transfer analysis may be executed in consideration of, as the heat transmission in relation to the thermocouple mesh 45, heat transfer and heat radiation between the thermocouple mesh 45 and the wall mesh 41 involving the thermocouple mesh 45 as well. However, that heat transfer is negligible because a heat transmission area between the thermocouple 39 and the wall 32 is small. When the heat radiation between the thermocouple mesh 45 and the wall mesh 41 is taken into consideration, for example, respective radiation rates of the wall 32 and the thermocouple 39 may be contained in the object information 120 as parts of the physical property values of the wall mesh 41 and the thermocouple mesh 45.

By thus executing the heat transfer analysis of step S160 in consideration of the heat transmission in relation to the thermocouple mesh 45, the CPU 12 derives, as values regarding the state of each small element after the lapse of the short time Δt from the time t, the wall temperature Tr of each wall mesh 41, the fluid temperature Tg of the fluid in each of the cell mesh 42 and the space mesh 44, and the thermocouple temperature Tt of each thermocouple mesh 45. Then, the CPU 12 derives respective values of the wall temperature Tr, the fluid temperature Tg, and the thermocouple temperature Tt for each mesh at each time from the time t=Δt to the time t=$t_{end}$ by repeatedly executing the heat transfer coefficient deriving process of steps S130 to S154 and the heat transfer analysis of step S160, and stores those values in the HDD 15. Alternatively, the wall temperature Tr, the fluid temperature Tg, and the thermocouple temperature Tt for each mesh at the time t=0, which are given as the initial conditions, may be added, and the values of the wall temperature Tr, the fluid temperature Tg, and the thermocouple temperature Tt for each mesh at each time from the time t=0 to the time t=$t_{end}$ may be stored in the HDD 15.

According to the analysis device 110 of this embodiment described above in detail, while executing the process of obtaining the object information 120 and the process of obtaining the thermocouple outer-peripheral-surface dimensionless correspondence information 26 from the HDD 15, the CPU 12 derives the thermocouple outer-peripheral-surface heat transfer coefficient $h_{ts}$ at an arbitrary time t from the analysis start time until the lapse of a predetermined time as follows. First, the CPU 12 sets, from among the plural meshes, the thermocouple mesh 45 and the cell mesh 42 as the target for derivation of the thermocouple outer-peripheral-surface heat transfer coefficient $h_{ts}$, and derives the dimensionless coordinate X* on the basis of the position information of the set mesh and the fluid state information regarding the state of the fluid in the set cell mesh 42 at the time t. Then, the CPU 12 derives, on the basis of the thermocouple outer-peripheral-surface dimensionless correspondence information 26, the thermocouple outer-peripheral-surface dimensionless heat transfer coefficient $Nu_{ts}$ corresponding to the derived dimensionless coordinate X*. Then, the CPU 12 derives, on the basis of the derived thermocouple outer-peripheral-surface dimensionless heat transfer coefficient $Nu_{ts}$, the thermocouple outer-peripheral-surface heat transfer coefficient $h_{ts}$ between the thermocouple mesh 45 and the cell mesh 42, which have been set as the derivation target. Thereafter, the CPU 12 executes the above-mentioned processes on the plural thermocouple meshes 45 and the plural cell meshes 42 while the derivation target is changed from one to another. In the heat transfer analysis, the CPU 12 executes the heat transfer analysis in consideration of the heat transfer amount $Q_{ts}$ between the thermocouple mesh 45 and the cell mesh 42 on the basis of the derived thermocouple outer-peripheral-surface heat transfer coefficients $h_{ts}$ at an arbitrary time from the analysis start time until the lapse of the predetermined time, thereby deriving the thermocouple temperature Tt of the thermocouple mesh 45 after the lapse of the short time Δt from the time t. In the temperature distribution deriving process, the CPU 12 repeatedly executes the inner-wall-surface heat transfer coefficient deriving process, the thermocouple outer-peripheral-surface heat transfer coefficient deriving process, and the heat transfer analysis process, thereby driving the respective wall temperatures Tr of the plural wall meshes 41 and the respective temperatures Tt of the plural thermocouple meshes 45 after the lapse of the predetermined time. As a result, the honeycomb structure 30 in the state including the thermocouples 39 inserted in the cells 35 can be analyzed. In addition, not only the temperatures of the walls 32, but also the temperatures of the thermocouples 39 can be analyzed.

In trying to evaluate thermal shock resistance when the honeycomb structure 30 is exposed to a high-temperature fluid, it is conceivable to make the honeycomb structure 30 exposed to the fluid in the state where the thermocouple 39 are actually inserted into the honeycomb structure 30, and to analyze a temperature distribution in the honeycomb structure 30 by employing temperatures detected by the thermocouples 39. However, a time lag (delay in temperature response) and an error may occur between the temperature of the wall 32 of the honeycomb structure 30 and the temperature detected by corresponding one of the thermocouples 39. In particular, as the wall thickness Wt of the wall 32 decreases, a difference (ratio) in thermal capacity between the wall 32 and the thermocouple 39 increases, and the influence of the response delay increases. Accordingly, evaluation accuracy reduces in the case of evaluating the thermal shock resistance with the use of a value actually measured by the thermocouple 39. In the above-described first and second embodiments, since the wall temperature Tr of the wall 32 can be derived instead of the temperature of the thermocouple 39 at each time for each wall mesh 41, the thermal shock resistance can be evaluated with high accuracy. In the second embodiment, since the thermocouple temperature Tt are further derived, respective values of the coefficients used in the dimensionless correspondence information 22 can be adjusted so as to increase the accuracy by employing a comparison result between the value actually measured by the thermocouple 39 and the derived thermocouple temperature Tt (in particular the thermocouple temperature Tt of the end mesh 45a in a temperature measurement portion). Moreover, by employing the comparison result between the value actually measured by the thermocouple 39 and the derived thermocouple temperature Tt, it is also possible to check the reason of causing a difference between the actually measured value and the thermocouple temperature Tt, and the extent of the difference. For example, when the honeycomb structure 30 is loaded with a catalyst, reaction heat due to purification of exhaust gas generates, and the value actually measured by the thermocouple 39 rises above the thermocouple temperature Tt. A distribution of the reaction heat at various locations inside the honeycomb structure 30 can also be examined from the resultant difference between the actually measured value and the derived thermocouple temperature Tt.

It is to be noted that the present invention is not limited to the above-described embodiments, and the present invention can be carried out in various forms insofar as not departing from the technical scope of the present invention.

For example, while, in the above first and second embodiments, the analysis is performed in connection with the case where the fluid flows into the honeycomb structure 30, the present invention is not limited to that case. As an alternative, the analysis may be performed in connection with the case where the front-rear direction (X-direction) of the honeycomb structure 30 is oriented in a vertical direction, and where the flow rate V and the flow velocity u within the cell 35 are determined depending on natural convection of the fluid in the cell 35. In that case, in above step S210 in FIG. 11, the flow velocity u of the fluid in the cell mesh 42 as the derivation target at the time t may be derived, by way of example, as follows. First, coefficients α and β in a relation between a pressure loss ΔP and the flow velocity u in the cell 35 (i.e., ΔP=α×u²+β×u) are determined in advance, and those coefficients are stored in the HDD 15 in correspondence to each cell mesh 42 in the object information 20. Then, in step S210, buoyancy of the fluid is calculated on the basis of both the fluid temperature of the cell 35 represented by the cell mesh 42 as the derivation target at the time t and an external temperature of the honeycomb structure 30. On that occasion, the fluid temperature of the cell 35 may be given as the fluid temperature Tg in the cell mesh 42 as the derivation target, but a maximum value among or an average value of the fluid temperatures Tg in the plural cell meshes 42 from the front end surface 33 to the rear end surface 34 of the cell 35 represented by the cell mesh 42 as the derivation target is preferably used. The external temperature of the honeycomb structure 30 is previously set as one of the analysis conditions in step S110 (namely, it is previously obtained and set in the HDD 15). Then, the flow velocity u is derived from the equation of buoyancy=pressure loss ΔP (=α×u²+β×u) by employing the calculated buoyancy and the determined coefficients α and β in correspondence to the cell mesh 42 as the derivation target. Even when the flow velocity u is derived as described above, the analysis can be performed in a similar manner to that in the above first and second embodiments.

While, in the above first and second embodiments, the physical property values of the fluid (i.e., the fluid density $\rho_g$, the fluid specific heat $Cp_g$, and the fluid thermal conductivity $\lambda_g$) are each assumed to be a value variable depending on the fluid temperature Tg (namely, variable depending on the time t), one or more of those values may be set to fixed values not variable depending on the time t. Even such a case can also provide the advantageous effect that the inner-wall-surface heat transfer coefficient $h_s$ and the thermocouple outer-peripheral-surface heat transfer coefficient $h_{ts}$, which reflect the fluid state information in an arbitrary mesh at an arbitrary time, can be derived appropriately.

While, in the above first and second embodiments, the flow rate V of the fluid at each time is set as the fluid inflow condition and the CPU 12 derives the flow velocity u from the flow rate V, the present invention is not limited to that case. For example, the flow velocity u of the fluid in each cell mesh 42 at each time may be set as the fluid flow condition (namely, the flow velocity u may be obtained and stored in the HDD 15). While the flow rate V of the fluid is assumed to be variable with the lapse of time from the analysis start time, the flow rate V may be constant. In other words, the flow velocity u may be constant instead of being variable depending on time. Furthermore, the flow velocity u may be the same value among the plural cells 35. The flow velocity u may be the same for the fluids in all the cells 35, or the flow velocity u may be constant regardless of the time t. Even those cases can also provide the advantageous effect that the inner-wall-surface heat transfer coefficient $h_s$ and the thermocouple outer-peripheral-surface heat transfer coefficient $h_{ts}$, which reflect the fluid state information in an arbitrary mesh at an arbitrary time, can be derived appropriately. It is to be noted that, even when the flow velocity u and the physical property values of the fluid (i.e., the fluid density $\rho_g$, the fluid specific heat $Cp_g$, and the fluid thermal conductivity $\lambda_g$) are all fixed values, the advantageous effect of being able to appropriately derive the inner-wall-surface heat transfer coefficient $h_s$ and the thermocouple outer-peripheral-surface heat transfer coefficient $h_{ts}$, which reflect the fluid state information at an arbitrary time in an arbitrary mesh, can be obtained.

While, in the above first and second embodiments, the front-end-surface heat transfer coefficient $h_{ef}$ and the rear-end-surface heat transfer coefficient $h_{er}$ are derived at each time t in the front-end-surface heat transfer coefficient deriving process and the rear-end-surface heat transfer coefficient deriving process, respectively, the present invention is not limited to that case, and those heat transfer coefficients may be set to fixed values not variable depending on time. For example, when the fluid thermal conductivity $\lambda_g$ is set to a fixed value not variable depending on the time t, the front-end-surface heat transfer coefficient $h_{ef}$ and the rear-end-surface heat transfer coefficient $h_{er}$ can be provided as values not variable depending on the time t. In that case, the front-end-surface heat transfer coefficient $h_{ef}$ and the rear-end-surface heat transfer coefficient $h_{er}$ may be each derived once for each mesh, and the derived value may be used as it is thereafter. As an alternative, respective values of the front-end-surface heat transfer coefficient $h_{ef}$ and the rear-end-surface heat transfer coefficient $h_{er}$ may be contained in the object information 20 from the beginning. The above description is similarly applied to the thermocouple end-surface heat transfer coefficient $h_{te}$ in the second embodiment.

In the above first and second embodiments, the weighted sum after the weighting with the weights assigned to the individual shape elements is derived, as the inner-wall-surface dimensionless heat transfer coefficient $Nu_s$ of the honeycomb mesh 40 as the derivation target, in step S230 of FIG. 11, as expressed by the equation (6) or (7). However, the inner-wall-surface dimensionless heat transfer coefficient $Nu_s$ for each shape element may be derived from the equation (1) or (2) without performing the weighting. In that case, the inner-wall-surface heat transfer coefficient $h_s$ may also be derived for each shape element by employing the equation (8), and the weighting for each shape element may be performed when the heat transfer amount $Q_s$ is derived from the equation (15). More specifically, the heat transfer amount $Q_s$ may be derived using the following equation (26) that is obtained by modifying the equation (15). As an alternative, a heat transmission area of the flat portion (i.e., a value corresponding to $K1 \times A_s$) and a heat transmission area of the corner portion (i.e., a value corresponding to $K2 \times A_s$) may be previously set, instead of the heat transmission area $A_s$, in the object information 20 of FIG. 4 in correspondence to the cell mesh 42, and the heat transfer amount $Q_s$ may be derived in a similar way to the equation (15) or (26) by employing the corresponding heat transmission area and the inner-wall-surface heat transfer coefficient $h_s$ for each shape element. The above description is similarly applied to the front-end-surface dimensionless heat transfer coefficient $Nu_{ef}$ and the rear-end-surface dimensionless heat transfer coefficient $Nu_{er}$.

$Q_s = \{K1 \times (\text{inner-wall-surface heat transfer coefficient } h_s \text{ of the flat portion}) + K2 \times (\text{inner-wall-surface heat transfer coefficient } h_s \text{ of the corner portion})\} \times (Tr - Tg) \times \text{heat transmission area } A_s$   Eq. (26)

While, in the above first and second embodiments, the physical property values of the wall 32 (i.e., the wall density $\rho_r$, the wall specific heat $Cp_r$, and the wall thermal conductivity $\lambda_{r1}$ or $\lambda_{r2}$) are assumed to be value not variable depending on the time t, at least one of those physical property values may be set to a value variable depending on, e.g., the wall temperature Tr. In such a case, for example, as with the conditions for the fluid physical properties, information (e.g., a relational equation or a map) enabling the relevant physical property value to be derived on the basis of the wall temperature Tr may be stored in the HDD 15, and the relevant physical property value at each time t may be derived on the basis of the wall temperature Tr at each time t.

While, in the above first and second embodiments, the honeycomb mesh 40 (the wall mesh 41) represents the state that a region involving at least a part of the walls 32 of the honeycomb structure 30 and at least a part of the cells 35 thereof together is homogenized, the present invention is not limited to that case, the wall meshes 41 and the cell meshes 42 may be arranged as illustrated in FIG. 8. However, the mesh preferably represents the homogenized state for the reason that the number of meshes can be reduced and the computing time can be shortened.

While, in the above first and second embodiments, each of the honeycomb meshes 40 serves as the wall mesh 41 and the cell mesh 42 (namely, one of the wall mesh 41 and the cell mesh 42 doubles as the other), the present invention is not limited to that case. For example, the wall mesh 41 and the cell mesh 42 may be arranged in a partly overlapping relation, or in a relation adjoining to each other with interposition of the inner wall surface 35*a* (i.e., a surface through which heat transfer occurs). In such a case, for example, a combination of the wall mesh 41 and the cell mesh 42 causing heat transfer through the inner wall surface 35*a* may be selected as the derivation target in step S200 of FIG. 11. Furthermore, the X-coordinate value x used in step S210 in the above case may be given as an X-coordinate value of one of the wall mesh 41 and the cell mesh 42 as the derivation target, or a value on the basis of the X-coordinates of those meshes (e.g., an intermediate value of the X-coordinates of both the meshes). The above description is similarly applied to steps S500 and S510 in FIG. 23 in relation to the second embodiment. When the wall mesh 41 and the cell mesh 42 are partly overlapped or adjacent to each other, the heat transfer amount $Q_s$ between the wall mesh 41 and the cell mesh 42 may be derived by modifying the heat transmission area $A_s$ in the equation (15) depending on, e.g., an extent of overlap between both the meshes or an area of adjacent surfaces of both the meshes.

While, in the above first and second embodiments, the cell shape is described as being a rectangular or hexagonal, for example, the present invention is not limited to that case, and the cell may have another polygonal shape, or a shape (e.g., circular) other than the polygonal shape. Moreover, while the shape elements are described as being the flat portion and the corner portion, the present invention is not limited to that case, and other shape elements may also be used. When a different cell shape or shape element from that used in the above embodiments is employed, a relational equation for deriving the dimensionless heat transfer coefficient may be the same as that used in the above embodiments, whereas only the coefficient(s) may be changed. Alternatively, another relational equation may be used. Correspondence relations other than the correspondence relations with respect to the dimensionless heat transfer coefficients, which are illustrated in FIGS. 12, 14, 16 and 24, and other than the correspondence relation with respect to the thermocouple end-surface dimensionless heat transfer coefficient, which is expressed by the equation (22), may also be used in the above embodiments. Required correspondence relations, relational equations, coefficients, and so on may be determined depending on cell shapes and shape elements with experiments or simulations.

While, in the above first and second embodiments, the inner-wall-surface dimensionless correspondence information 23 contains the correspondence relations that are different for each shape and each shape element of the inner wall surface 35*a* of the cell 35 in the honeycomb mesh 40 as the derivation target, the present invention is not limited to that case. For example, correspondence relations that are different only for each cell shape may be used without using correspondence relations different for each shape element. Alternatively, the same correspondence relation may be used for different cell shapes without using correspondence relations different for each cell shape. The above description is similarly applied to the front-end-surface dimensionless correspondence information 24 and the rear-end-surface dimensionless correspondence information 25.

While, in the above first and second embodiments, the heat transfer analysis process is executed in accordance with the finite volume method, the present invention is not limited to that case, and another analysis method may be used. For example, the finite element method or the difference method may be used instead.

Figure 26:
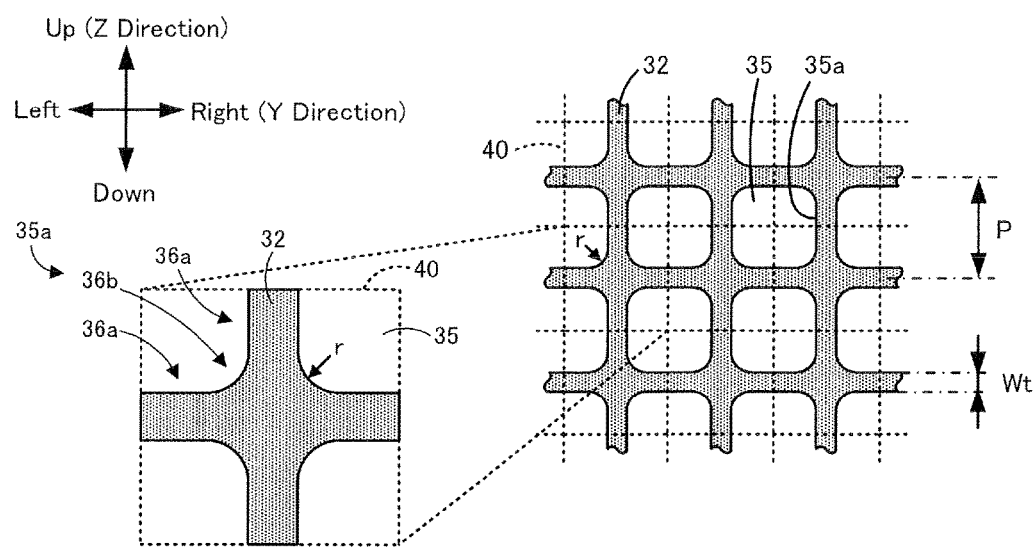
FIG. 26 is an explanatory view of the walls 32, the cells 35, and the honeycomb meshes 40 when the corner portion 36b has the curved surface.

In the above first embodiment, it is suggested that the corner portion 36*b* of the inner wall surface 35*a* of the cell 35 may have the curved surface. FIG. 26 is an explanatory view of the walls 32, the cells 35, and the honeycomb meshes 40 when the corner portion 36*b* has the curved surface. When the corner portion 36*b* has the curved surface as illustrated in FIG. 26, a curvature radius r of the corner portion 36*b* may be set as the structural information in correspondence to the honeycomb mesh 40 (the wall mesh 41 or the cell mesh 42).

Figure 27:
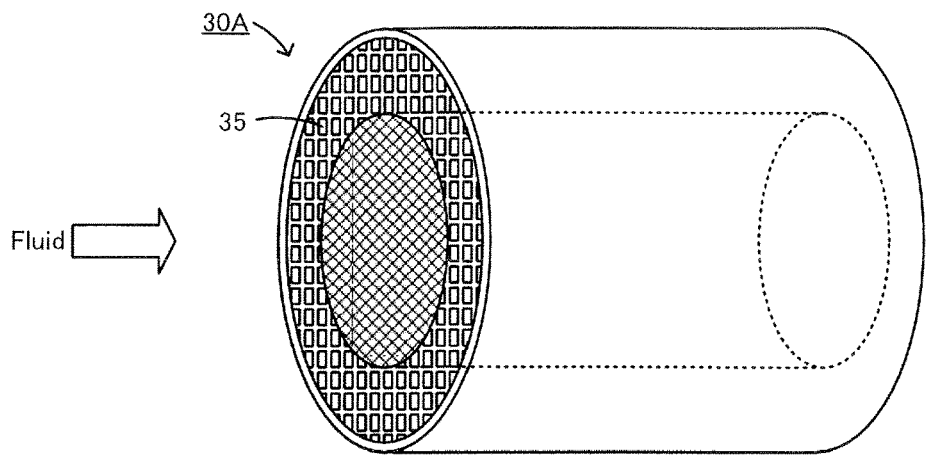
FIG. 27 is an explanatory view of honeycomb structures 30A which is an example of honeycomb structures having locally different structural configurations.
Figure 28:
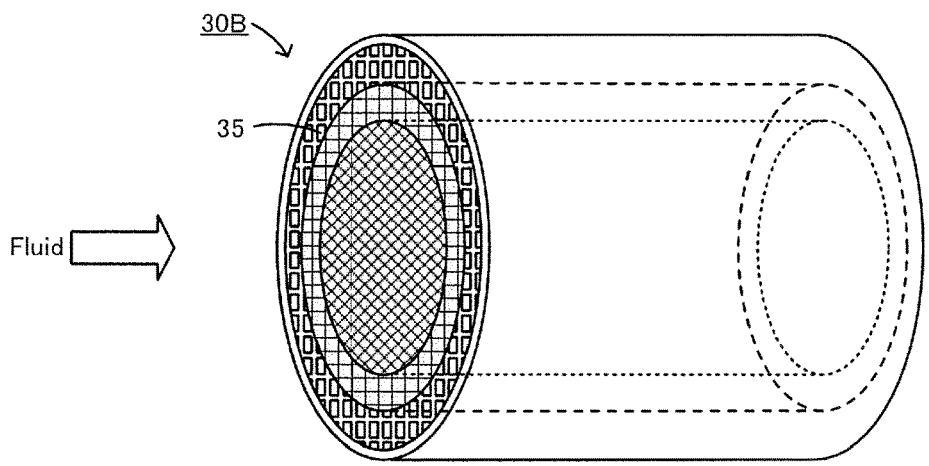
FIG. 28 is an explanatory view of honeycomb structures 30B which is an example of honeycomb structures having locally different structural configurations.
Figure 29:
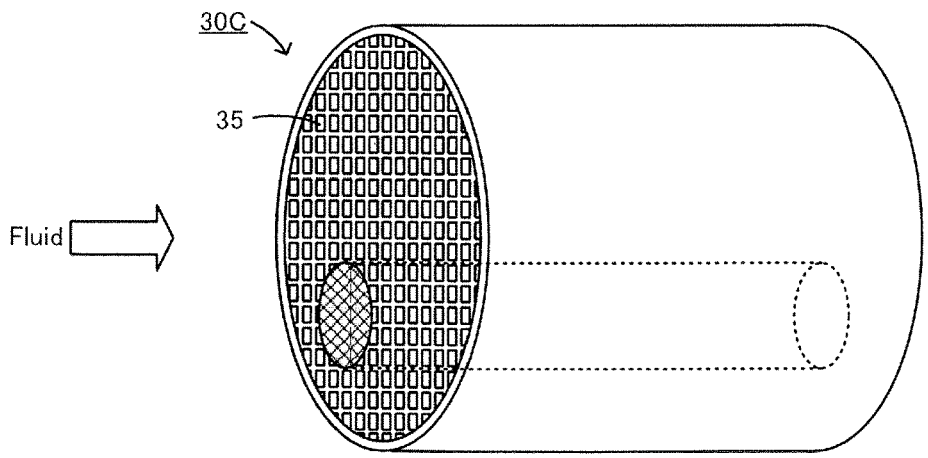
FIG. 29 is an explanatory view of honeycomb structures 30C which is an example of honeycomb structures having locally different structural configurations.

In the above first and second embodiments, it is suggested that the structural information and the physical property values may be set to the same values for all the wall meshes 41, and that the structural information and the shape information may be set to the same values for all the cell meshes 42. It is also suggested that, in correspondence to each of the honeycomb meshes 40 positioned at locations including the outer peripheral surface of the honeycomb structure 30, a different value may be set depending on the shape of a portion of the honeycomb structure 30, the portion being included in the relevant honeycomb mesh 40. The present invention is not limited to such a modification. The information set in the object information 20 in correspondence to the honeycomb mesh 40 may be different depending on the position information (XYZ-coordinates) to be able to simulate the shape of each of individual portions of the honeycomb structure 30, the portions being expressed by the position information (XYZ-coordinates). For example, when the honeycomb structure includes portions, which are locally different in structural configurations, in addition to the locations involving the outer peripheral surface of the honeycomb structure, the information (e.g., the structural information, the physical property values, and shape information) in correspondence to the honeycomb mesh 40 may be set for each of the portions having different structural configurations. FIGS. 27 to 29 are explanatory views of honeycomb structures 30A to 30C that are examples of honeycomb structures having locally different structural configurations. The honeycomb structure 30A of FIG. 27 has a columnar center region and a cylindrical outer peripheral region, which are arranged in a concentric relation. The structural configuration (e.g., at least one of the shape and the size) of the cell 35 is different between the center region and the outer peripheral region. The honeycomb structure 30B of FIG. 28 has three concentric regions, and the structural configuration of the cell 35 is different among those three regions. In the honeycomb structure 30C of FIG. 29, a columnar region present at a position offset from a center axis has a different structural configuration of the cell 35 from that of the other region. Even for structures like the honeycomb structures 30A to 30C, the structural configuration in each of the different regions can be simulated by employing the object information 20 in which the information of the honeycomb mesh 40 corresponding to each of the different regions is set depending on the position information (XYZ-coordinates). By employing the thus-prepared object information 20, the state of the honeycomb structure when the honeycomb structure is exposed to the fluid can be analyzed with higher accuracy even for honeycomb structures, which are partly different in the structural configuration of the cell, as in the above first and second embodiments. Regardless of honeycomb structures having what types of structural configurations, the state of the honeycomb structure when the honeycomb structure is exposed to the fluid can be analyzed with higher accuracy by preparing the object information that simulates the relevant structural configuration, and by executing the analysis process in a similar manner to that in the above first or second embodiment. Examples of honeycomb structures other than the above-described ones are as follows. While, in the honeycomb structures 30A to 30C of FIGS. 27 to 29, a boundary between two regions having different structural configurations has a circular shape in cross-section, the present invention is not limited to that case, and the boundary therebetween may have an elliptic shape. The honeycomb structures 30A and 30C of FIGS. 27 and 29 each include two regions having different structural configurations, and the honeycomb structure 30B of FIG. 28 includes three regions having different structural configurations. However, the present invention is not limited to those cases, and the honeycomb structure may include four or more regions having different structural configurations. Furthermore, the boundary between the regions having different structural configurations is not always needed to be clear like a honeycomb structure including a region where the structural configuration is changed continuously. While, in the honeycomb structures 30A and 30B of FIGS. 27 and 28, the regions having the different structural configurations are concentrically positioned, they are not always needed to be concentric. While, in the honeycomb structure 30C of FIG. 29, the region having the different structural configuration from that of the other region is columnar, it may have another shape without being limited to the columnar shape. As an alternative, the honeycomb structure may have a shape in a proper combination of the structural features of the honeycomb structures 30A to 30C illustrated in FIGS. 27 to 29.

The present application claims priority from Japanese Patent Application No. 2015-070757, filed on Mar. 31, 2015, and Japanese Patent Application No. 2016-058968, filed on Mar. 23, 2016, the entire contents of which are incorporated herein by reference.

What is claimed is:

1. A method for analyzing a honeycomb structure that analyzes a state of the honeycomb structure, including walls forming a plurality of cells that serve as flow paths for a fluid, after lapse of a predetermined time from an analysis start time when the honeycomb structure is exposed to the fluid using an analysis device comprising: a computing apparatus, which includes an object information obtaining module; an inner-wall-surface dimensionless correspondence information obtaining module; an inner-wall-surface heat transfer coefficient deriving module, a heat transfer analysis module; and a temperature distribution deriving module, the method comprising:

an object information obtaining step, in the object information obtaining module, of obtaining object information that simulates the honeycomb structure with a plurality of meshes involving wall meshes representing the walls and cell meshes representing the cells, the object information containing position information for each of the meshes;

an inner-wall-surface dimensionless correspondence information obtaining step, in the inner-wall-surface dimensionless correspondence information obtaining module, of obtaining inner-wall-surface dimensionless correspondence information that is information regarding a correspondence relation between a dimensionless coordinate, which is a dimensionless value indicating a position of the mesh, and an inner-wall-surface dimensionless heat transfer coefficient, which is a dimensionless value of an inner-wall-surface heat transfer coefficient representing a heat transfer coefficient between an inner wall surface of the cell and the fluid;

an inner-wall-surface heat transfer coefficient deriving step, in the inner-wall-surface heat transfer coefficient deriving module, of executing, at an arbitrary time from the analysis start time until lapse of the predetermined time, a process of setting, from among the plurality of meshes, the wall mesh and the cell mesh as a derivation target for which the inner-wall-surface heat transfer coefficient is to be derived, deriving the dimensionless coordinate on basis of both the position information of the set mesh and fluid state information regarding a state of the fluid in the set cell mesh at the relevant time, deriving the inner-wall-surface dimensionless heat transfer coefficient corresponding to the derived dimensionless coordinate on basis of the inner-wall-surface dimensionless correspondence information, and deriving the inner-wall-surface heat transfer coefficient between the set wall mesh and the set cell mesh on basis of the derived inner-wall-surface dimensionless heat transfer coefficient, and further executing the aforesaid process for the plural wall meshes and the plural cell meshes while the derivation target is changed from one to another;

a heat transfer analysis step, in the heat transfer analysis module, of executing, at an arbitrary time from the analysis start time until the lapse of the predetermined time, a heat transfer analysis including a process of deriving a heat transfer amount between the wall mesh and the cell mesh on basis of the inner-wall-surface heat transfer coefficient derived in the inner-wall-surface heat transfer coefficient deriving step, and deriving temperatures of the plural wall meshes and temperatures of the fluids in the plural cell meshes after lapse of a short time from the relevant time; and a temperature distribution deriving step, in the temperature distribution deriving module, of repeatedly executing the inner-wall-surface heat transfer coefficient deriving step and the heat transfer analysis step, and deriving respective temperatures of the plural wall meshes after the lapse of the predetermined time.

2. The method for analyzing a honeycomb structure according to claim 1, wherein, in the object information, one or more of the plural wall meshes each represent a region of the honeycomb structure, the region involving at least a part of the walls and at least a part of the cells together, in a homogenized state.

3. The method for analyzing a honeycomb structure according to claim 1, wherein the object information contains, in correspondence to at least one of the wall mesh and the cell mesh, shape information regarding a shape of the inner wall surface of the cell, the inner-wall-surface dimensionless correspondence information contains the correspondence relation between the dimensionless coordinate and the inner-wall-surface dimensionless heat transfer coefficient, the relevant correspondence relation being different for each shape of the inner wall surface, and in the inner-wall-surface heat transfer coefficient deriving step, derivation of the inner-wall-surface dimensionless heat transfer coefficient on basis of the inner-wall-surface dimensionless correspondence information is executed by employing the correspondence relation between the dimensionless coordinate and the inner-wall-surface dimensionless heat transfer coefficient, the relevant correspondence relation being specified on basis of the shape information in correspondence to the mesh set as the derivation target.

4. The method for analyzing a honeycomb structure according to claim 1, wherein the object information contains, in correspondence to at least one of the wall mesh and the cell mesh, shape information that is information representing a shape of the inner wall surface of the cell as a combination of plural shape elements, the inner-wall-surface dimensionless correspondence information contains the correspondence relation between the dimensionless coordinate and the inner-wall-surface dimensionless heat transfer coefficient, the relevant correspondence relation being different for each of the shape elements of the combination of plural shape elements, and in the inner-wall-surface heat transfer coefficient deriving step, the derivation of the inner-wall-surface dimensionless heat transfer coefficient corresponding to each of the shape elements is executed by employing the correspondence relation between the dimensionless coordinate and the inner-wall-surface dimensionless heat transfer coefficient, the relevant correspondence relation being specified on basis of each of the shape elements of the combination of plural shape elements contained in the shape information in correspondence to the mesh set as the derivation target.

5. The method for analyzing a honeycomb structure according to claim 4, wherein the object information is information simulating the honeycomb structure in which the inner wall surface of at least one of the plural cells has a polygonal cross-section, and the shape information contains, as the plural shape elements, a corner portion and a flat portion of an inner wall surface of the polygonal cross-section.

6. The method for analyzing a honeycomb structure according to claim 1, wherein the inner-wall-surface dimensionless correspondence information contains, as the correspondence relation between the dimensionless coordinate and the inner-wall-surface dimensionless heat transfer coefficient in a fluid entrance region of the cell, information regarding a correspondence relation expressed by following equation (1), and in the inner-wall-surface heat transfer coefficient deriving step, the inner-wall-surface dimensionless heat transfer coefficient is derived on basis of the information regarding the correspondence relation expressed by the equation (1) when the derived dimensionless coordinate is positioned in the fluid entrance region:

$$Nu_s = A \times (X^*)^B \qquad \text{Eq. (1),}$$

where $Nu_s$: inner-wall-surface dimensionless heat transfer coefficient, $X^*$: dimensionless coordinate, and A, B: coefficients.

7. The method for analyzing a honeycomb structure according to claim 1, wherein the inner-wall-surface dimensionless correspondence information contains, as the correspondence relation between the dimensionless coordinate and the inner-wall-surface dimensionless heat transfer coefficient in a fluid developed region of the cell, information regarding a correspondence relation expressed by following equation (2), and in the inner-wall-surface heat transfer coefficient deriving step, the inner-wall-surface dimensionless heat transfer coefficient is derived on basis of the information regarding the correspondence relation expressed by the equation (2) when the derived dimensionless coordinate is positioned in the fluid developed region:

$$Nu_s = C \qquad \text{Eq. (2),}$$

where $Nu_s$: inner-wall-surface dimensionless heat transfer coefficient and C: coefficient.

8. The method for analyzing a honeycomb structure according to claim 1, further comprising an end-surface heat transfer coefficient deriving step of executing, at an arbitrary time from the analysis start time until lapse of the predetermined time, a process of setting, from among a plurality of end wall meshes belonging to the wall meshes and representing the walls that involve open end surfaces of the cells in the honeycomb structure, one end wall mesh as a target for derivation of an end-surface heat transfer coefficient representing a heat transfer coefficient between the open end surface of the relevant end wall mesh and the fluid, obtaining an end-surface dimensionless heat transfer coefficient that is a dimensionless value of the end-surface heat transfer coefficient in the set end wall mesh, and deriving the end-surface heat transfer coefficient in the set end wall mesh on basis of the derived end-surface dimensionless heat transfer coefficient, and further executing the aforesaid process for the plural end wall meshes while the derivation target is changed from one to another, wherein, in the heat transfer analysis step, the heat transfer analysis is executed at an arbitrary time from the analysis start time until the lapse of the predetermined time in consideration of a heat transfer amount between the end wall mesh and the fluid, the heat transfer amount being derived on basis of the derived end-surface heat transfer coefficient, and the inner-wall-surface heat transfer coefficient deriving step, the end-surface heat transfer coefficient deriving step, and the heat transfer analysis step are repeatedly executed in the temperature distribution deriving step to derive respective temperatures of the plural wall meshes after the lapse of the predetermined time.

9. The method for analyzing a honeycomb structure according to claim 8, wherein the object information contains, in correspondence to the end wall mesh, information regarding an opening rate that is a value representing a rate of an opening of the cell in the open end surface, and in the end-surface heat transfer coefficient deriving step, the end-surface dimensionless heat transfer coefficient is derived and obtained on basis of the opening rate of the end wall mesh set as the derivation target.

10. The method for analyzing a honeycomb structure according to claim 9, wherein, in the end-surface heat transfer coefficient deriving step, the end-surface dimensionless heat transfer coefficient is derived from a relation of following equation (3):

$$Nu_e = D \times \exp(E \times OFA) \qquad \text{Eq. (3)},$$

where $Nu_e$: end-surface dimensionless heat transfer coefficient, D, E: coefficients, and OFA: opening rate.

11. The method for analyzing a honeycomb structure according to claim 1, wherein the object information is information simulating the honeycomb structure, which is in a state including a thermocouple inserted in the cell, with a plurality of meshes involving the wall meshes, the cell meshes, and a plurality of thermocouple meshes representing the thermocouple, the method further comprises a thermocouple outer-peripheral-surface dimensionless correspondence information obtaining step of obtaining thermocouple outer-peripheral-surface dimensionless correspondence information that is information regarding a correspondence relation between a dimensionless coordinate, which is a dimensionless value indicating a position of the mesh, and a thermocouple outer-peripheral-surface dimensionless heat transfer coefficient, which is a dimensionless value of a thermocouple outer-peripheral-surface heat transfer coefficient representing a heat transfer coefficient between an outer peripheral surface of the thermocouple and the fluid; and a thermocouple outer-peripheral-surface heat transfer coefficient deriving step of executing, at an arbitrary time from the analysis start time until the lapse of the predetermined time, a process of setting, from among the plurality of meshes, the thermocouple mesh and the cell mesh as a derivation target for which the thermocouple outer-peripheral-surface heat transfer coefficient is to be derived, deriving the dimensionless coordinate on basis of both the position information of the set mesh and the fluid state information regarding the fluid in the set cell mesh at the relevant time, deriving the thermocouple outer-peripheral-surface dimensionless heat transfer coefficient corresponding to the derived dimensionless coordinate on basis of the thermocouple outer-peripheral-surface dimensionless correspondence information, and deriving the thermocouple outer-peripheral-surface heat transfer coefficient between the set thermocouple mesh and the set cell mesh on basis of the derived thermocouple outer-peripheral-surface dimensionless heat transfer coefficient, and further executing the aforesaid process for the plural thermocouple meshes and the plural cell meshes while the derivation target is changed from one to another, in the heat transfer analysis step, the heat transfer analysis is executed at an arbitrary time from the analysis start time until the lapse of the predetermined time in consideration of a heat transfer amount between the thermocouple mesh and the cell mesh, the heat transfer amount being derived on basis of the derived thermocouple outer-peripheral-surface heat transfer coefficient, thus deriving a temperature of the thermocouple mesh after the lapse of a short time from the relevant time, and the inner-wall-surface heat transfer coefficient deriving step, the thermocouple outer-peripheral-surface heat transfer coefficient deriving step, and the heat transfer analysis step are repeatedly executed in the temperature distribution deriving step to derive respective temperatures of the plural wall meshes and respective temperatures of the thermocouple meshes after the lapse of the predetermined time.

12. The method for analyzing a honeycomb structure according to claim 1, further comprising a stress analysis step of analyzing a distribution of stress, which is generated inside the honeycomb structure, on basis of the respective temperatures of the wall meshes derived in the temperature distribution deriving step.

13. A non-transitory computer readable recording medium storing a program that, upon execution of which by one or more computers operate and execute the steps of the method for analyzing a honeycomb structure according to claim 1.

14. An analysis device for analyzing a honeycomb structure that analyzes a state of the honeycomb structure, including walls forming a plurality of cells that serve as flow paths for a fluid, after lapse of a predetermined time from an analysis start time when the honeycomb structure is exposed to the fluid, the analysis device comprising:

a CPU and memory comprising software instructions executed by the CPU implementing the following modules:

an object information obtaining module for obtaining object information that simulates the honeycomb structure with a plurality of meshes involving wall meshes representing the walls and cell meshes representing the cells, the object information containing position information for each of the meshes;

an inner-wall-surface dimensionless correspondence information obtaining module for obtaining inner-wall-surface dimensionless correspondence information that is information regarding a correspondence relation between a dimensionless coordinate, which is a dimensionless value indicating a position of the mesh, and an inner-wall-surface dimensionless heat transfer coefficient, which is a dimensionless value of an inner-wall-surface heat transfer coefficient representing a heat transfer coefficient between an inner wall surface of the cell and the fluid;

an inner-wall-surface heat transfer coefficient deriving module for executing an inner-wall-surface heat transfer coefficient deriving process, that is, executing, at an arbitrary time from the analysis start time until lapse of the predetermined time, a process of setting, from among the plurality of meshes, the wall mesh and the cell mesh as a derivation target for which the inner-wall-surface heat transfer coefficient is to be derived, deriving the dimensionless coordinate on basis of both the position information of the set mesh and fluid state information regarding a state of the fluid in the set cell mesh at the relevant time, deriving the inner-wall-surface dimensionless heat transfer coefficient corresponding to the derived dimensionless coordinate on basis of the inner-wall-surface dimensionless correspondence information, and deriving the inner-wall-surface heat transfer coefficient between the set wall mesh and the set cell mesh on basis of the derived inner-wall-surface dimensionless heat transfer coefficient, and further executing the aforesaid process for the plural wall meshes and the plural cell meshes while the derivation target is changed from one to another;

a heat transfer analysis module for executing a heat transfer analysis process, that is, executing, at an arbitrary time from the analysis start time until the lapse of the predetermined time, a heat transfer analysis including a process of deriving a heat transfer amount between the wall mesh and the cell mesh on basis of the inner-wall-surface heat transfer coefficient derived in the inner-wall-surface heat transfer coefficient deriving process, and deriving temperatures of the plural wall meshes and temperatures of the fluids in the plural cell meshes after lapse of a short time from the relevant time; and a temperature distribution deriving module for repeatedly executing the inner-wall-surface heat transfer coefficient deriving process and the heat transfer analysis process by the inner-wall-surface heat transfer coefficient deriving module and the heat transfer analysis module, and deriving respective temperatures of the plural wall meshes after the lapse of the predetermined time.

* * * * *